(12) United States Patent
Harrison et al.

(10) Patent No.: US 11,701,073 B2
(45) Date of Patent: *Jul. 18, 2023

(54) FILTRATION METHODS FOR DUAL-ENERGY X-RAY CT

(71) Applicant: Rensselaer Polytechnic Institute, Troy, NY (US)

(72) Inventors: Daniel David Harrison, Delanson, NY (US); Ge Wang, Loudonville, NY (US)

(73) Assignee: Rensselaer Polytechnic Institute, Troy, NY (US)

(*) Notice: Subject to any disclaimer, the term of this patent is extended or adjusted under 35 U.S.C. 154(b) by 53 days.

This patent is subject to a terminal disclaimer.

(21) Appl. No.: 17/354,286

(22) Filed: Jun. 22, 2021

(65) Prior Publication Data
US 2021/0321961 A1 Oct. 21, 2021

Related U.S. Application Data

(63) Continuation of application No. 16/294,438, filed on Mar. 6, 2019, now Pat. No. 11,051,772, which is a (Continued)

(51) Int. Cl.
*A61B 6/00* (2006.01)
*A61B 6/03* (2006.01)

(52) U.S. Cl.
CPC ............ *A61B 6/4035* (2013.01); *A61B 6/032* (2013.01); *A61B 6/4085* (2013.01);
(Continued)

(58) Field of Classification Search
CPC ..... A61B 6/5258; A61B 6/4035; A61B 6/032; A61B 6/4085; A61B 6/4007; A61B 6/482; A61B 6/542; A61B 6/4021; A61B 6/405; A61B 6/54; A61B 6/4042; A61B 6/035; A61B 6/4291; A61B 6/587; A61B 6/502;
(Continued)

(56) References Cited

U.S. PATENT DOCUMENTS 6,633,627 B2 * 10/2003 Horiuchi .............. A61B 6/4035
378/4
7,082,189 B2 * 7/2006 Yahata ..................... A61B 6/06
378/158

(Continued)

*Primary Examiner* — Irakli Kiknadze
(74) *Attorney, Agent, or Firm* — Murtha Cullina LLP; Anthony P. Gangemi

(57) ABSTRACT

Systems and method for performing X-ray computed tomography (CT) that can improve spectral separation and decrease motion artifacts without increasing radiation dose are provided. The systems and method can be used with either a kVp-switching source or a single-kVp source. When used with a kVp-switching source, an absorption grating and a filter grating can be disposed between the X-ray source and the sample to be imaged. Relative motion of the filter and absorption gratings can by synchronized to the kVp switching frequency of the X-ray source. When used with a single-kVp source, a combination of absorption and filter gratings can be used and can be driven in an oscillation movement that is optimized for a single-kVp X-ray source. With a single-kVp source, the absorption grating can also be omitted and the filter grating can remain stationary.

20 Claims, 40 Drawing Sheets

Related U.S. Application Data continuation of application No. 16/092,393, filed as application No. PCT/US2017/026322 on Apr. 6, 2017, now Pat. No. 11,337,663.

(60) Provisional application No. 62/638,984, filed on Mar. 6, 2018, provisional application No. 62/333,882, filed on May 10, 2016, provisional application No. 62/319,881, filed on Apr. 8, 2016.

(52) U.S. Cl.
CPC .......... *A61B 6/5258* (2013.01); *A61B 6/4007* (2013.01); *A61B 6/482* (2013.01)

(58) Field of Classification Search
CPC ......... A61B 6/4241; A61B 6/484; A61B 6/06; A61B 6/4078; A61B 6/107; A61B 6/583; A61B 6/488; A61B 6/027; A61B 6/507; A61B 6/469; A61B 6/481; A61B 6/5205; G21K 1/10; G21K 1/06; G21K 2207/005; G21K 1/025
USPC ..................................................... 378/16, 19
See application file for complete search history.

(56) References Cited

U.S. PATENT DOCUMENTS

| | | | |
|---|---|---|---|
| 9,101,272 B2* | 8/2015 | O'Loughlin | A61B 6/4035 |
| 11,051,772 B2* | 7/2021 | Harrison | A61B 6/5258 |
| 2014/0112441 A1* | 4/2014 | Becker | A61B 6/545 |
| | | | 378/62 |
| 2014/0185746 A1* | 7/2014 | Baturin | G21K 1/06 |
| | | | 378/36 |
| 2017/0273642 A1* | 9/2017 | Engel | A61B 6/4035 |

* cited by examiner

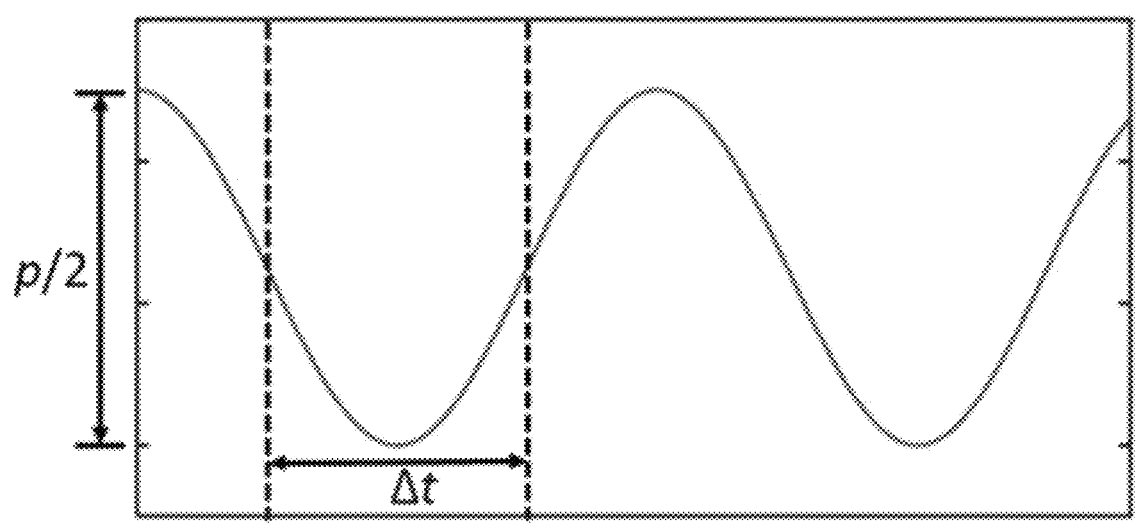
FIG. 3A
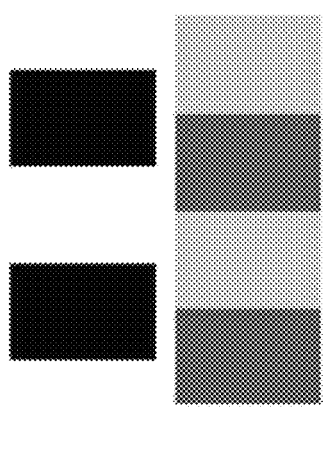     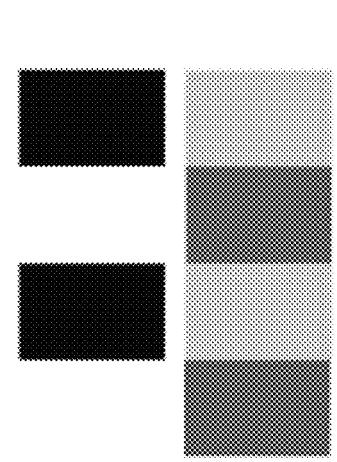     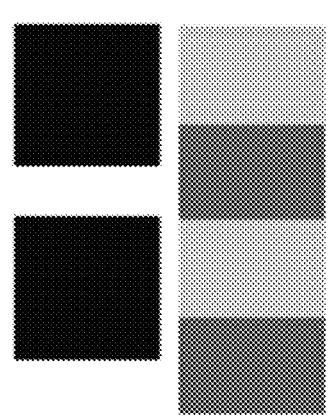
FIG. 3B          FIG. 3C          FIG. 3D

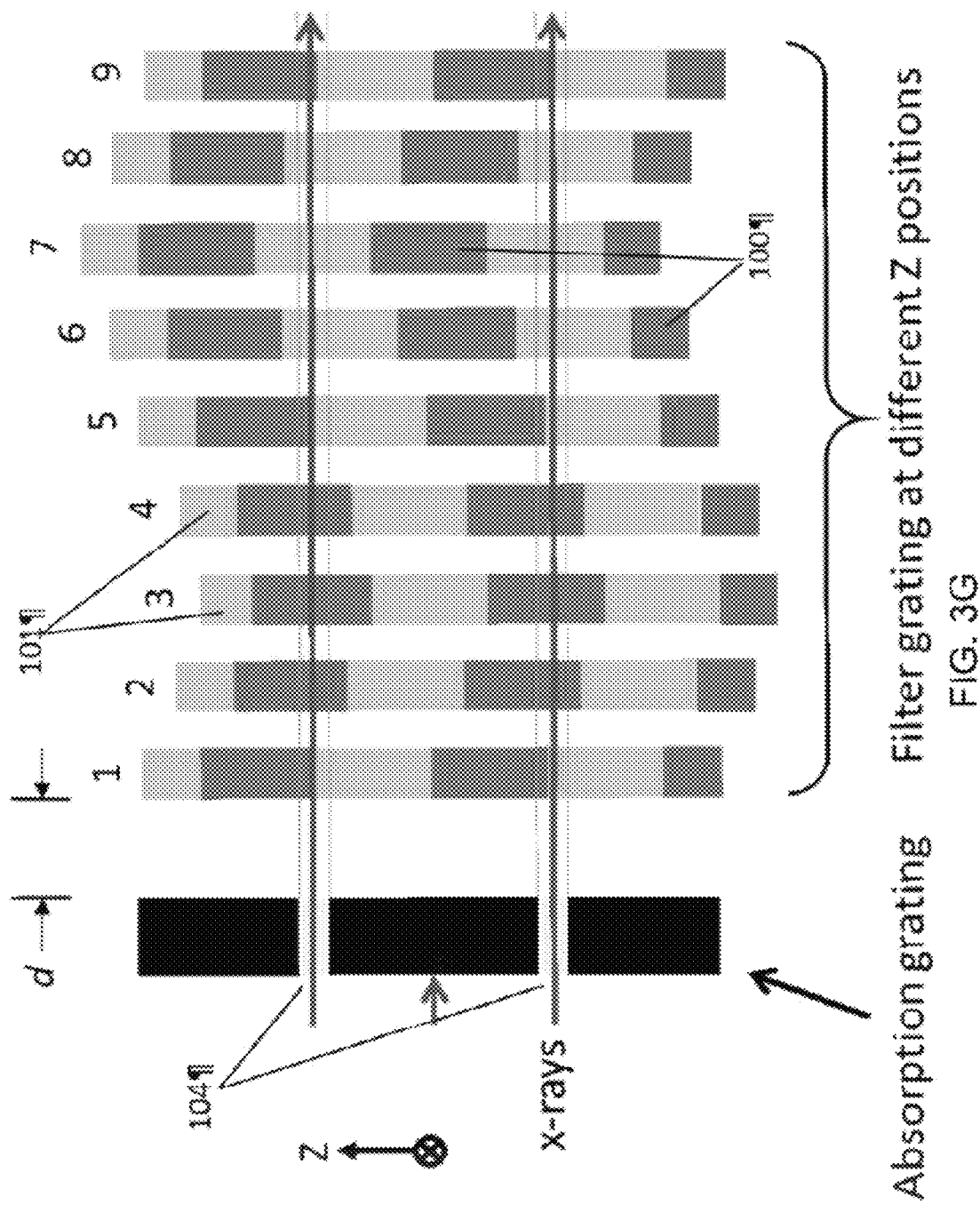

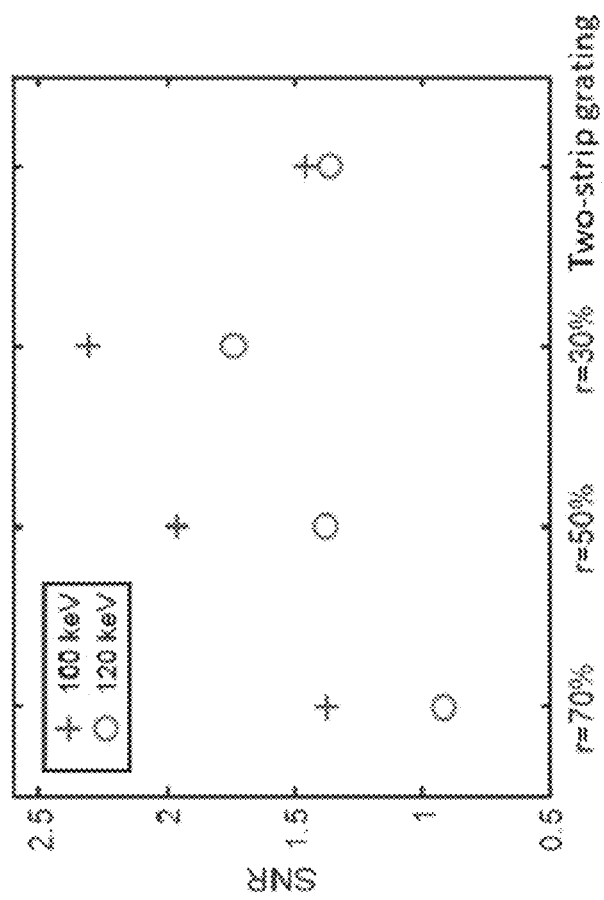
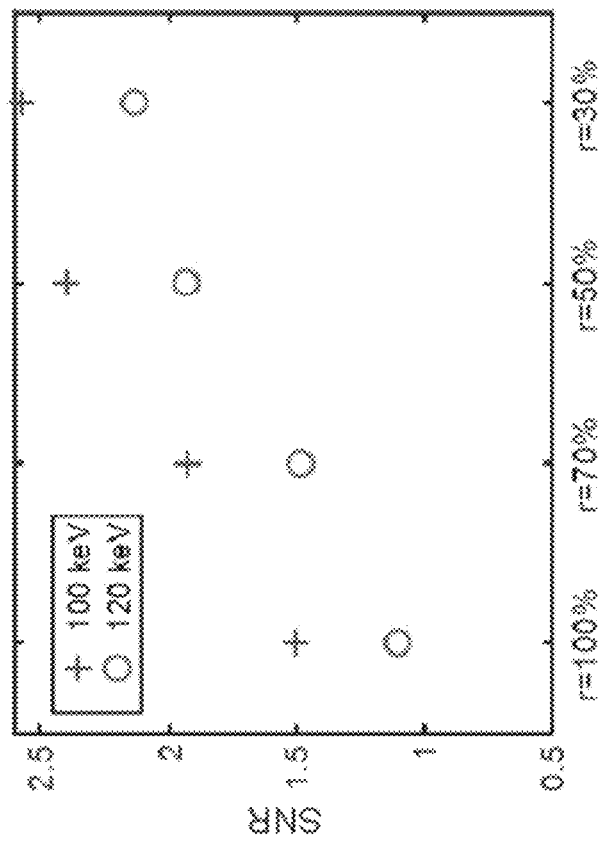
FIG. 13B
FIG. 13A

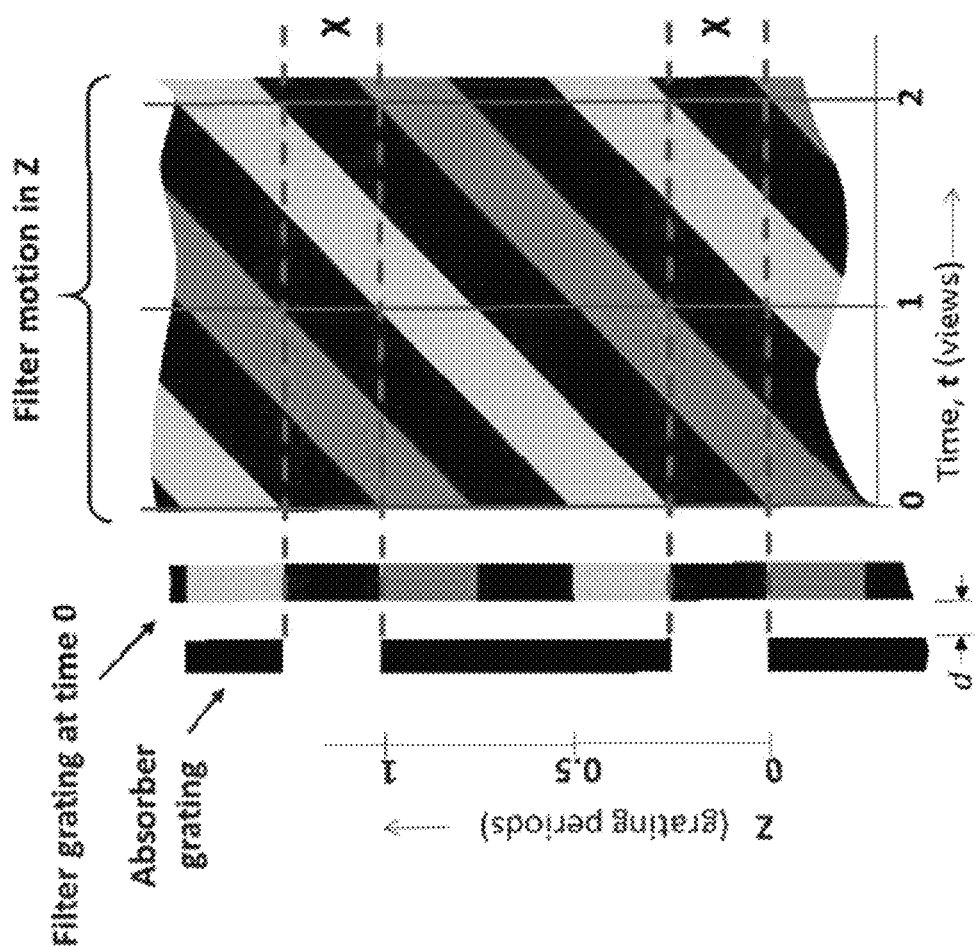
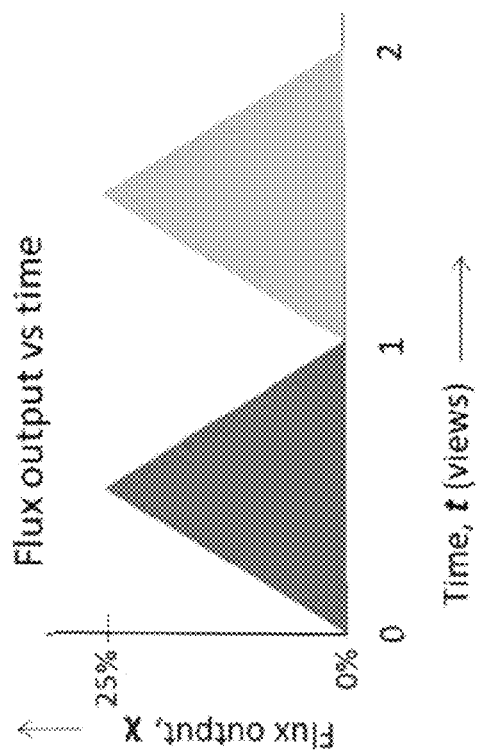
FIG. 22B
FIG. 22A

FILTRATION METHODS FOR DUAL-ENERGY X-RAY CT

CROSS REFERENCE TO RELATED APPLICATIONS

This application claims the benefit of U.S. Provisional Patent Application Ser. No. 62/319,881, filed Apr. 8, 2016, U.S. Provisional Patent Application Ser. No. 62/333,882, filed May 10, 2016, International Application No. PCT/US2017/026322, filed Apr. 6, 2017, U.S. Utility patent application Ser. No. 16/092,393, filed Oct. 9, 2018, U.S. Provisional Patent Application Ser. No. 62/638,984, filed Mar. 6, 2018, and U.S. Utility patent application Ser. No. 16/294,438, filed Mar. 6, 2019, the disclosures of which are hereby incorporated by reference in their entirety, including any figures, tables, and drawings.

GOVERNMENT LICENSE RIGHTS

This invention was made with government support under Prime Award No. 1U01EB017140-01A1 Subaward No. 60807421-108947 awarded by the National Institutes of Health. The government has certain rights in the invention.

BACKGROUND

Since the invention of X-ray computed tomography (CT) in 1971, it has gone through many improvements, including fanbeam, multi-slice and cone-beam spiral CT methods, which add longitudinal dimension to CT images. Also, dual-energy/multi-energy CT technologies add spectral dimension to CT images. Even though dual-energy CT has some advantages, monochromatic imaging and material decomposition can be performed, which reduces X-ray radiation dose and facilitates a number of important applications. Multi-energy CT is an emerging field, but it still needs time to become mature and enter the clinical world.

Currently, dual-energy CT technologies can be classified into three categories: kVp-switching; dual-layer detection; and dual-source scanning. The kVp-switching method is an X-ray source technology in which low- and high-energy X-ray beams are alternatingly emitted during a scan. The dual-layer detector method is based on a detector innovation so that low- and high-energy data are collected in two sensor layers respectively. These two methods both use a single X-ray source to generate dual-energy datasets. Thus, the resultant low- and high-energy datasets share the same X-ray filter placed in front of the X-ray source. Different from the single-source-based dual-energy CT systems, a dual-source system includes two imaging subsystems. The dual-source CT system is more expensive, and there is a temporal discrepancy between low- and high-energy data acquisitions. Breathing, heart beating, and patient motion causes artifacts in reconstructed images, compromising material decomposition and monochromatic imaging.

BRIEF SUMMARY

Embodiments of the subject invention include systems and method for performing X-ray computed tomography (CT) that can improve spectral separation and decrease motion artifacts without increasing radiation dose to which a patient is exposed during imaging. Systems and methods of embodiments of the subject invention can be used with either a kVp-switching source or a single-kVp source. When used with a kVp-switching source, an absorption grating and a filter grating can be disposed between the X-ray source and where a sample/patient to be imaged would be (or is) located (e.g., in front of the X-ray source). Relative motion of the filter and absorption gratings can by synchronized to the kVp switching frequency of the X-ray source. Different filter regions can be exposed to X-rays at various time instants, thereby producing low- and high-energy X-rays accordingly. When used with a single-kVp source, a combination of absorption and filter gratings can be used and can be driven in an oscillation movement that is optimized for a single-kVp X-ray source. In certain embodiments, only a filter grating alone is required, and the filter grating can be stationary with respect to the X-ray source. In a specific embodiment, the filter grating can be just a two-strip filter.

In an embodiment, a system for performing X-ray CT imaging can comprise: an X-ray source; a detector for detecting X-ray radiation from the source; a filter grating disposed between the source and the detector; and an absorption grating disposed between the filter grating and the source. At least one of the absorption grating and the filter grating can be configured to move relative to the other during operation of the source. The filter grating can be positioned closer to the source than it is to the detector (for example, in front of the source). The source can be either a kVp-switching source or a non-kVp-switching source, and the oscillation (relative movement) between the gratings can be optimized depending on what type of source is used.

In another embodiment, a system for performing X-ray CT imaging can comprise: a single-kVp X-ray source (non-kVp-switching X-ray source); a detector for detecting X-ray radiation from the source; and a filter grating disposed between the source and the detector. The filter grating can be positioned closer to the source than it is to the detector (for example, in front of the source), and the system can specifically exclude an absorption grating. The filter grating can be configured to be stationary during operation of the source. Image reconstruction for such a system can be based on a non-linear X-ray data generation model. The image reconstruction can include non-linear data modeling and compressed sensing.

In some embodiments, therefore, the present technology combines an absorption grating and a filter grating in front of an x-ray source, and moves one grating with respect to the other for a nearly instantaneous filter change. In some embodiments, the relative motion is small and is synchronized with source kVp-switching and/or detector-view sampling for collection of well-aligned dual-energy datasets. In some embodiments, one of the gratings is moved by a high-precision manipulator such as a piezo-electrical motor for rapid oscillation. Some embodiments in which rapid grating motion (sometimes referred to as vibrational grating oriented line-wise filtration or "GOLF") is utilized are integrated with or retrofitted with current CT scanners.

In other embodiments, the filter or absorption grating is moved in only a single direction relative to the other grating. This movement can be either in a linear direction or a rotational direction, depending on the embodiment. In some embodiments, the filter and/or absorption gratings are curved. In some embodiments, the gratings are concentrically curved, and the moving grating is moved along a correspondingly curved path. In some embodiments, the gratings are substantially cylindrically shaped. In some embodiments, the gratings are substantially spherically shaped.

In some embodiments, the filter grating includes, in addition to more than one type of filtering region, regions of absorber material interleaved between each filtering region.

BRIEF DESCRIPTION OF DRAWINGS

FIG. 3A shows an oscillation curve of a filter grating.

FIG. 3B shows a top view of an absorption grating (left) and a filter grating (right) including two different types of filter (different shadings) according to an embodiment of the subject invention.

FIG. 3C shows a top view of an absorption grating (left) and a filter grating (right) including two different types of filter (different shadings) according to an embodiment of the subject invention.

FIG. 3D shows a top view of an absorption grating (left) and a filter grating (right) including two different types of filter (different shadings) according to an embodiment of the subject invention.

FIG. 3G shows a schematic view similar to FIG. 3F, but with a reduced absorption-grating duty cycle, achieved at least in part through use of a narrower slit.

FIG. 13A shows a plot of signal-to-noise ratio (SNR) for the images of FIG. 9.

FIG. 13B shows a plot of SNR for the images of FIG. 11.

FIG. 22A shows a plot of the flux output and filter type vs time for the arrangement shown in FIG. 22B.

FIG. 22B shows a schematic view of a filter grating with constant-velocity movement along the Z-axis and source that is constantly on.

DETAILED DESCRIPTION

Embodiments of the subject invention include systems and method for performing X-ray computed tomography (CT) that can improve spectral separation and decrease motion artifacts without increasing radiation dose to which a patient (e.g., a mammal patient such as a human) or sample is exposed during imaging. Systems and methods of embodiments of the subject invention can be used with either a kVp-switching (kilovolt-peak-switching (voltage-alternating)) X-ray source or a single-kVp (non-kVp-switching) X-ray source (e.g., X-ray tube). When used with a kVp-switching X-ray source, an absorption grating and a filter grating can be disposed between the X-ray source and where a sample/patient to be imaged would be (or is) located (e.g., in front of the X-ray source). Relative motion of the filter and absorption gratings can by synchronized to the kVp switching frequency of the X-ray source (e.g., X-ray tube). Different filter regions can be exposed to X-rays at various time instants, thereby producing low- and high-energy X-rays accordingly. When used with a single-kVp (non-kVp-switching) X-ray source, a combination of absorption and filter gratings can be used and can be driven in an oscillation movement (relative to each other) that is optimized for a single-kVp X-ray source. With X-rays of the same energy spectrum, different filtration materials can be used to generate X-rays in two (or more) energy spectra (one of them at any given time instant). In certain embodiments, only a filter grating alone is required, and the filter grating can be stationary with respect to the X-ray source (e.g., X-ray tube). This stationary approach presents a minimum demand for CT hardware enhancement. In a specific embodiment, the filter grating can be just a two-strip filter.

Figure 1A:
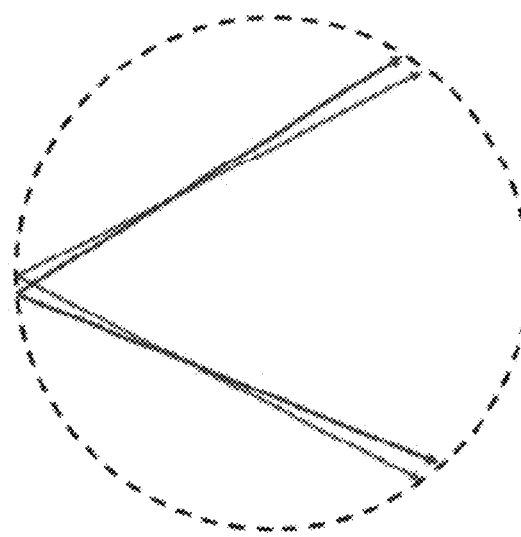
FIG. 1A shows a depiction of kVp-switching X-ray computed tomography (CT).
Figure 1B:
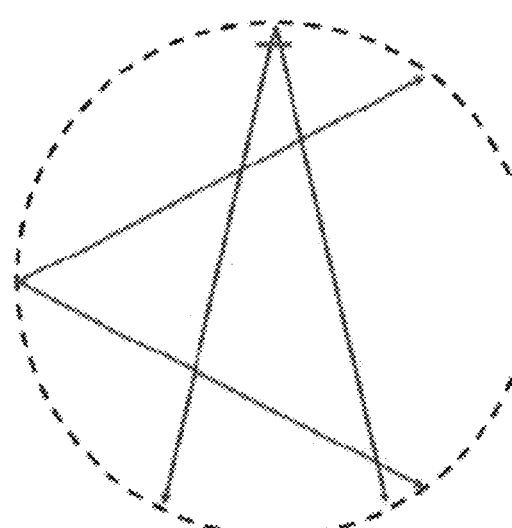
FIG. 1B shows a depiction of dual-source detection X-ray CT.
Figure 1C:
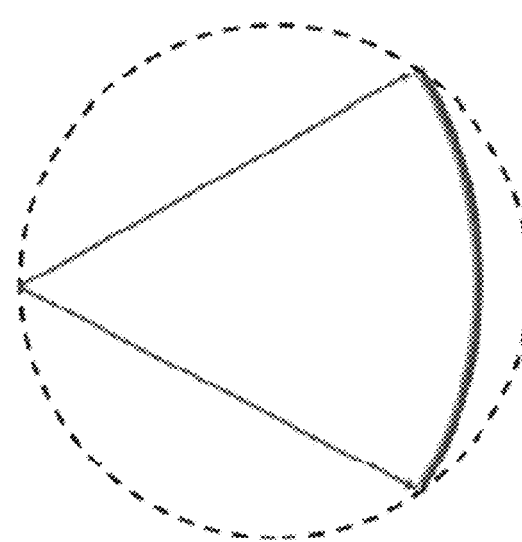
FIG. 1C shows a depiction of dual-layer scanning X-ray CT.
Figure 1D:
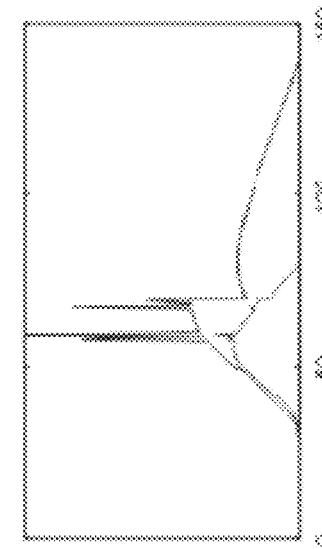
FIG. 1D shows a plot of low- and high-energy spectra for kVp-switching X-ray CT.
Figure 1E:
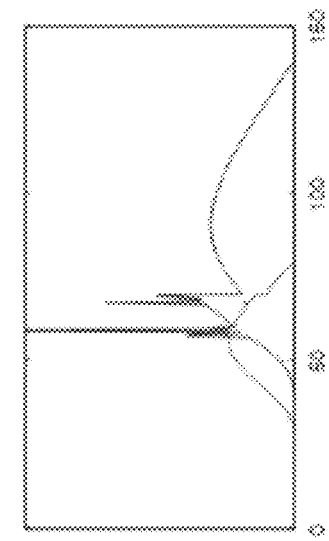
FIG. 1E shows a plot of low- and high-energy spectra for dual-source detection X-ray CT.
Figure 1F:
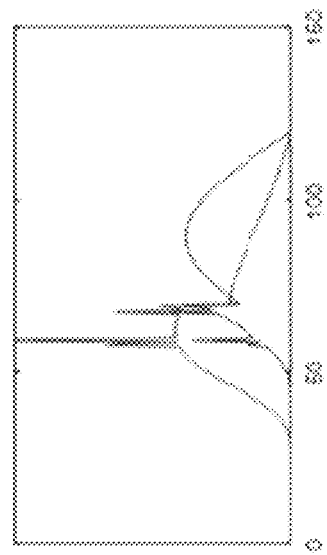
FIG. 1F shows a plot of low- and high-energy spectra for dual-layer scanning X-ray CT.

Dual-energy CT technologies can be classified into the three categories: kVp-switching; dual-layer detection; and dual-source scanning. FIGS. 1A-1C are depictions of beams for kVp-switching, dual-source detection, and dual-layer scanning, respectively. The kVp-switching method is an X-ray source technology in which low- and high-energy x-ray beams are alternatingly emitted during a scan. The dual-layer detector method is based on a detector innovation so that low- and high-energy data are collected in two sensor layers respectively. These two methods both use a single X-ray source to generate dual-energy datasets. Generally, the resultant low- and high-energy datasets share the same X-ray filter placed in front of the X-ray source, and as a result, the low- and high-energy X-rays are not well separated, as shown in FIGS. 1D and 1E, which are plots for conventional kVp-switching and dual-layer detection, respectively, of low- and high-energy spectra. In a dual-source system, there are two imaging subsystems. Because the X-ray sources are independent, different X-ray filters can be customized for more flexible X-ray filtration, and the low- and high energy X-ray entrance spectra can be individually shaped, yielding a better spectral separation, as shown in FIG. 1F. However, dual-source CT systems are more expensive and result in a temporal discrepancy between low- and high-energy data acquisitions. Breathing, heart beating, and patient motion cause artifacts in reconstructed images for related art dual-source systems, compromising material decomposition and monochromatic imaging.

Embodiments of the subject invention can simultaneously address the spectral overlapping problem with kVp-switching and dual-layer detection systems, as well as the motion artifact problem with a dual-source scanner. Grating oriented line-wise filtration (GOLF) systems and methods can enable interlaced filtration patterns for superior energy separation. An X-ray filtration device can be easily integrated into a CT scanner and its scanning procedure. Depending on the X-ray source type, three main filtration systems/methods can be used, which can be referred to as $GOLF_k$, $GOLF_c$, and $GOLF_s$.

$GOLF_k$ can be used for a kVp-switching X-ray source. $GOLF_k$ can combine an absorption grating and a filter grating disposed between the X-ray source and where a sample/patient to be imaged would be (or is) located (e.g., in front of the X-ray source). $GOLF_k$ can synchronize relative motion of the filter and absorption gratings to the kVp switching frequency of the X-ray source (e.g., X-ray tube). For example, the filter grating can be driven by a high-precision manipulator, such as a piezo-electrical motor for rapid oscillation of one grating relative to the other. Different filter regions can be exposed to X-rays at various time instants, thereby producing low- and high-energy X-rays accordingly.

$GOLF_c$ and $GOLF_s$ can work with a conventional (e.g., non-kVp-switching) X-ray source. $GOLF_c$ can use a combination of absorption and filter gratings optimized for an X-ray source (e.g., X-ray tube) without kVp-switching. The X-ray filter grating and/or the X-ray absorption grating can be driven in an oscillation movement relative to each other. $GOLF_s$ only requires a filter grating alone that is stationary with respect to the X-ray source (e.g., X-ray tube). This stationary approach presents a minimum demand for CT hardware enhancement. In a specific embodiment of $GOLF_s$, the filter grating can be just a two-strip filter.

Figure 2B:
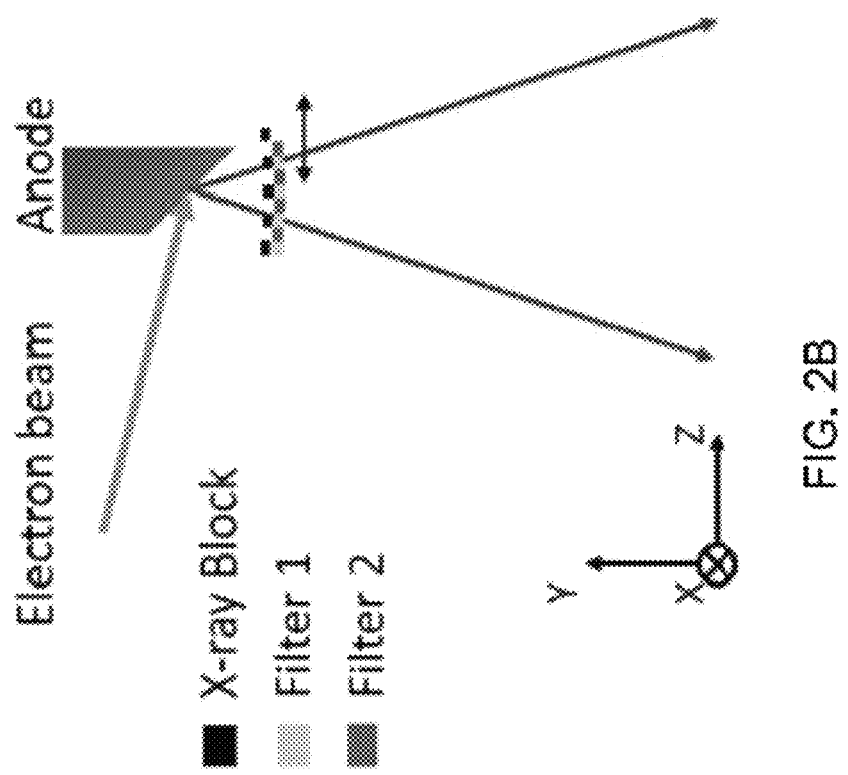
FIG. 2B shows a layout of gratings disposed in front of an X-ray source according to an embodiment of the subject invention.
Figure 2A:
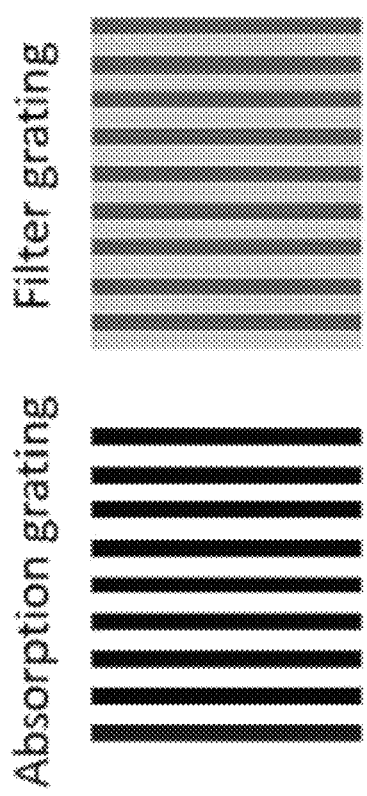
FIG. 2A shows example filter and absorption gratings that can be used in a system or method according to an embodiment of the subject invention.

FIG. 2A shows example filter and absorption gratings that can be used in a $GOLF_k$ system or method according to an embodiment of the subject invention, and FIG. 2B shows a layout of gratings disposed in front of the X-ray source. Although FIG. 2A shows an X-ray tube with electron beam and anode as the X-ray source, along with two filters making up the filter grating, these are for exemplary purposes only and should not be construed as limiting. Referring to FIGS. 2A and 2B, the absorption grating can be disposed between the X-ray source and the filter grating, and the gratings can be moved relative to each other during operation of the X-ray source. The movement of the gratings can be in a direction parallel to the front face of the grating (i.e., in the z-direction as depicted in FIG. 2B). In addition, the filter grating can include one filter or a plurality of filters. The absorption grating can comprise or be entirely composed of an X-ray absorption material (e.g., gold) to let X-rays go through its open slits only. In this way, the X-rays allowed to go through can be controlled by choosing the width of each slit, the number of slits, the width between slits, and the number of solid portions (non-slits). The width of slits and/or solid portions can be uniform across the grating, individually or in total, or such widths can vary. The filter grating can spectrally modify the X-ray beam through grating materials. For example, the filter grating can include thin metal strips interlacing one or more filtering materials (e.g., two filtering materials). The duty cycle of the filter grating can be, for example, 50%, though embodiments are not limited thereto. Through relative displacement of the two gratings, incident X-rays are filtered at different time instants by different kinds of filtering strips. Also, in further embodiments, a plurality of absorption gratings and/or filter gratings can be used.

The two gratings can be overlaid in front of the X-ray source, as shown in FIG. 2B. In the kVp-switching based dual-energy CT system, the entrance X-rays can alternate at low- and high-energy levels. Synchronously, the filter grating can be driven at the same high-frequency relative to the absorption grating. For low-energy X-ray imaging, the filter grating can oscillate in such a way that the first set of filtering strips happen to be in the X-ray path. Then, for high-energy X-ray imaging, the second set of filtering strips can be exposed to the X-ray source.

Figure 2D:
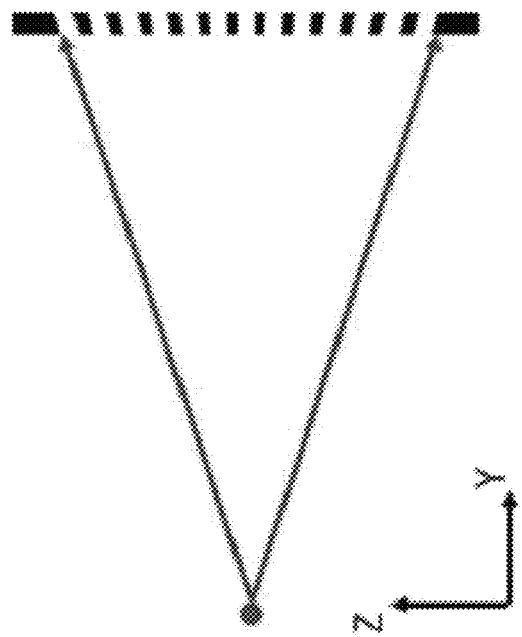
FIG. 2D shows a cross-sectional view of a curved grating having slits designed for a curved geometry according to an embodiment of the subject invention.
Figure 2C:
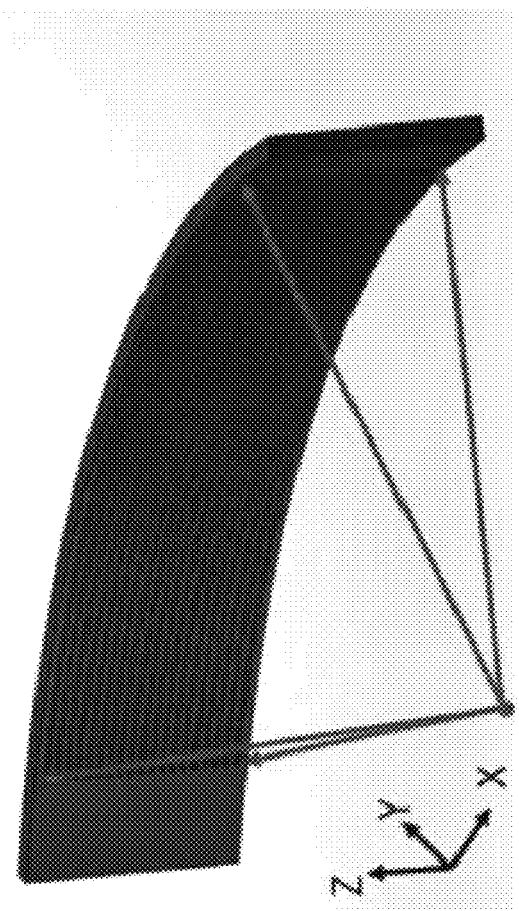
FIG. 2C shows a stationary curved absorption grating that can be used according to an embodiment of the subject invention.
Figures 2E, 2F:
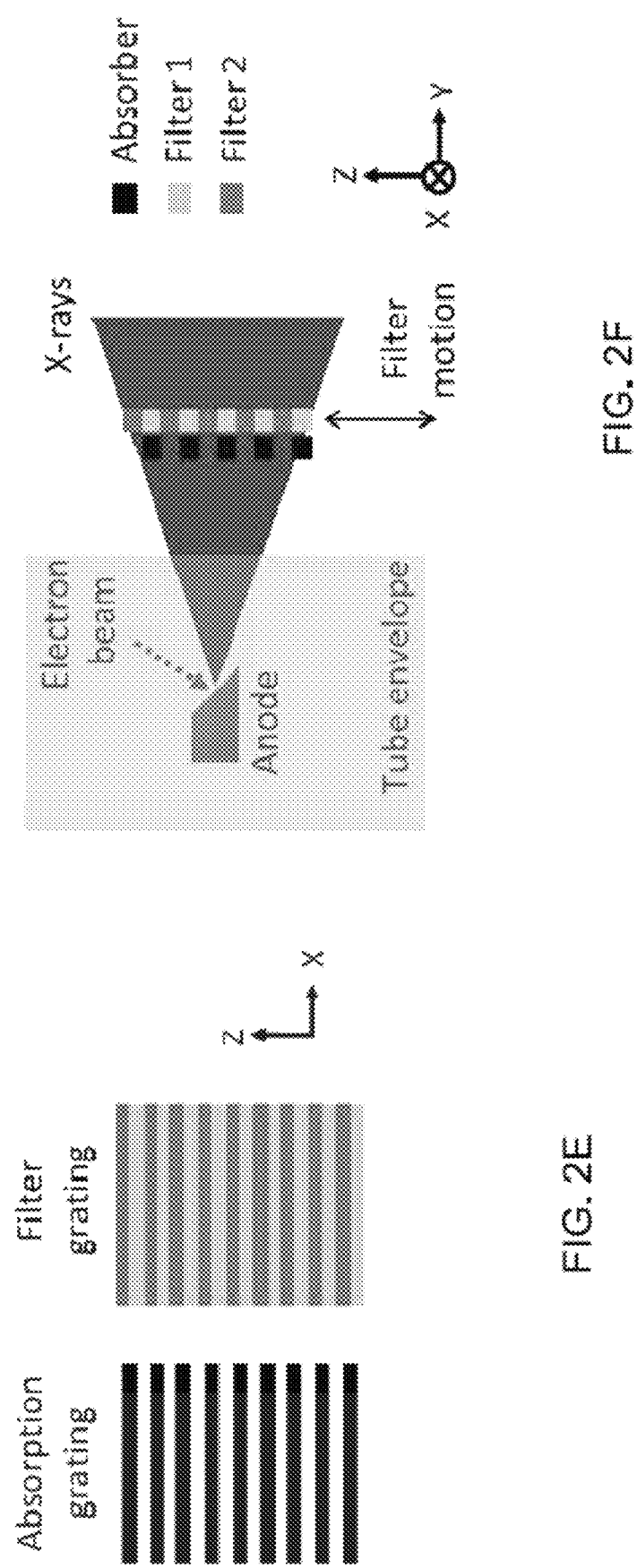
FIG. 2E shows an example filter and absorption gratings according to an embodiment of the invention.
FIG. 2F shows an example of grating placements relative to an X-ray tube in an exemplary embodiment of the invention.

In some embodiments, a vibrational GOLF system uses a thin-sheet absorption grating and a thin-sheet filter grating, as shown in FIG. 2E. The gratings are overlaid and placed in the x-ray beam at the tube output, as shown in FIG. 2F. In some embodiments, the absorption grating consists of interlaced bars and open slits, with the bars made of x-ray absorbing material such as Gold so that incident x-rays pass only through the open slits. In some embodiments, the filter grating consists of interlaced type-1 and type-2 filtering strips with the two types chosen to yield significantly different filtered x-ray spectra. In some embodiments, the absorption and filter gratings are periodic and matched so that either of the two interlaced filters can be imposed on the entire x-ray beam by shifting the filter grating only one-half period relative to the absorption grating. In some embodiments, the grating period is smaller than the x-ray source spot size. The purpose of the absorption grating is to provide a place for one of the interlaced filters to hide (out of the x-ray beam), while the other filter intersects the x-ray beam. FIG. 2F shows the filter grating as the moved grating and places it after the absorption grating on the x-ray path. In other embodiments, however, either grating or both of them can be moved. In some embodiments it is most practical to move the one with the least mass. Furthermore, there will be some scatter from the GOLF assembly and scatter at the detector may be less with one grating arrangement instead of another. In some embodiments, the absorption grating is between the anode and the filter grating, while in other embodiments, the filter grating is between the anode and the absorption grating.

In certain embodiments, the gratings can be configured to fit a curved geometry. FIG. 2C shows a stationary curved absorption grating, and FIG. 2D shows a cross-sectional view of a grating having slits designed for a curved geometry. Referring to FIGS. 2C and 2D, one or more gratings can be configured to fit a curved geometry, such as for a third generation CT implementation. The strips in a curved absorption grating can be aligned according to X-ray emitting angles in a cone geometry, as shown in FIG. 2C. In a specific embodiment, the period of the filter grating can be 0.5 mm with a duty cycle of 50%, the strips in the flat absorption grating can be made of 1 mm gold strips with high X-ray absorption, and the materials of the filter grating are air and 1 mm tin corresponding to low- and high-energy X-ray filtrations, respectively.

In embodiments of a $GOLF_k$ system or method, the motion direction of the filter grating can be perpendicular to the longitudinal direction of the filter strips. Thus, half (or about half) of the original X-rays can be blocked by the absorption grating, and the other half (or about half) can get filtered by the corresponding strips of the filter grating. With kVp-switching based dual-energy CT, the low- and high-energy X-rays are emitted in turn.

In many embodiments of a $GOLF_k$ system or method, the filter grating vibration frequency can be matched to the X-ray kVp-switching frequency. Also, the vibration amplitude can be optimized according to the duty cycle of the absorption grating. With the duty cycle being ½r, the optimized vibration amplitude is $$(1-r)\frac{p}{2}.$$

FIG. 3A shows an oscillation curve of a filter grating according to an embodiment. Referring to FIG. 3A, the oscillation period is equal to half the time interval between two adjacent X-ray projections in the kVp-switching CT scan. FIGS. 3B-3D show top views of an absorption grating (left) and a filter grating (right) including two different types of filter (different shadings). An ideal X-ray filtration setting is shown in FIG. 3C, in which the absorption grating and the filter grating are in a perfect alignment, without filter materials mixed in the x-ray beam. Referring to FIG. 3C, the filter grating can be aligned such that one of its filter materials matches up with each slit of the absorption grating. However, during the exposure period t, the absorption grating and the filter grating are in relative motion, and the X-rays are filtered by two filters with a changing material mixture, for example leading to the orientation shown in FIG. 3B at certain times. FIG. 3D shows an example absorption grating with a narrower grating opening. Referring to FIG. 3D, the configuration with a narrower opening minimizes the problems that may be caused by mixed filtration, but this can come at a cost of reduced photon efficiency.

Figures 3E, 3F:
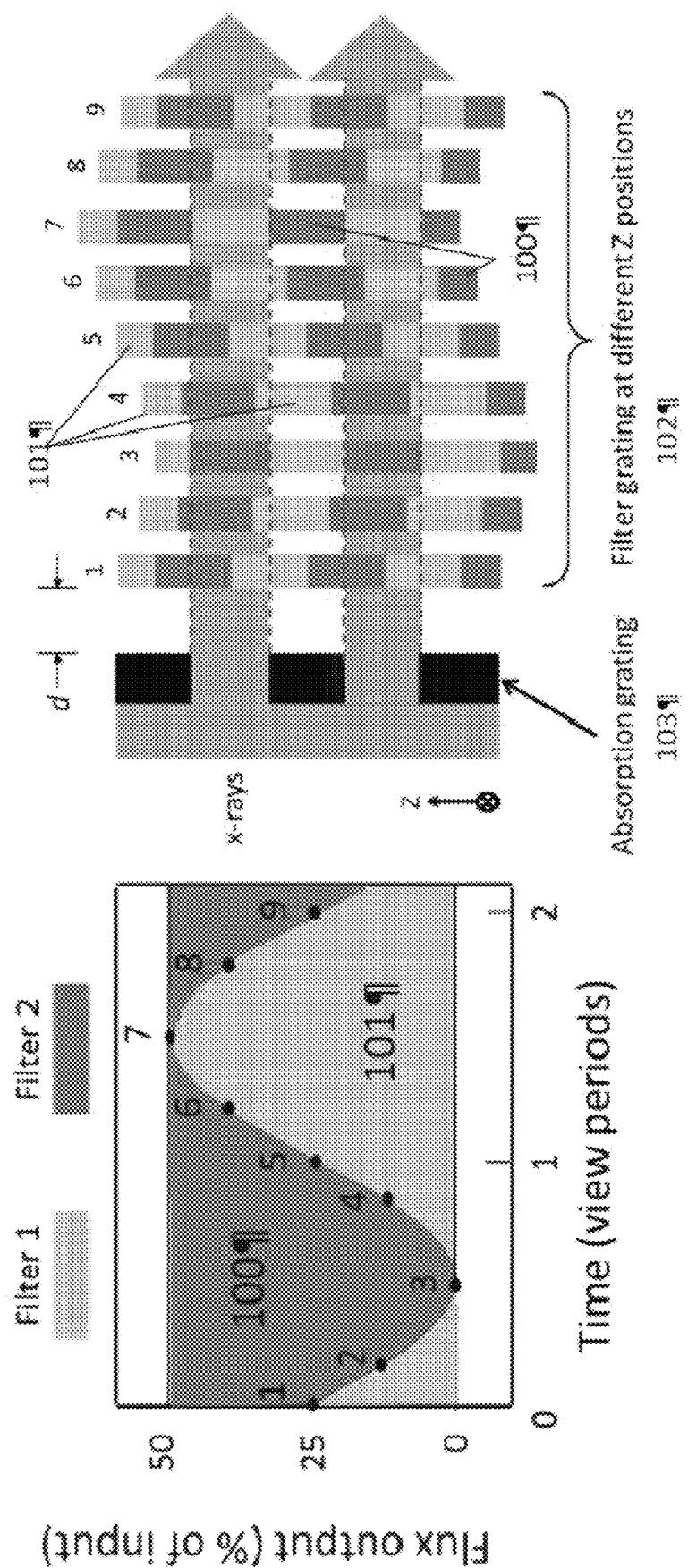
FIG. 3E shows a plot of filter output flux and filter composition vs time for an embodiment of the invention including a stationary absorption grating and a moving filter grating with sinusoidal filter motion.
FIG. 3F shows a schematic view of a sequence of filter Z-axis positions associated with numbered times in FIG. 3(E). The x-rays flow from left to right with a constant absorption-filter separation, d.

When used with kVp-switching, embodiments of GOLF systems improve the spectral separation by placing a high-pass filter in the beam when the tube voltage is high, and a low-pass filter in the beam when the tube voltage is low. Contemporary kVp-switching toggles the tube voltage at the end of every detector view period. FIGS. 3E and F show how some embodiments of the present technology operate when the absorption grating 103 is stationary and the filter grating 102 is moved. FIG. 3E shows a plot of the flux output and filter composition vs time, where sinusoidal displacement of the filter grating is used. The filter grating has two sets of filter regions 100 and 101. This displacement waveform arises in embodiments that include detector view rate of approximately 1 kHz or more. FIG. 3F shows relative Z-dimension (vertical) positions of the absorption and filter gratings associated with numbered times in FIG. 3E (points 1-9). In this embodiment, the filter moves only in the Z direction, while the distance between the absorption and filter gratings, d, is held constant as in position 1. The first filter 100 is x-rays low-pass, and the second filter 101 is high-pass. At position 3, all x-rays that pass the absorption grating are low-pass filtered, while at position 7, all x-rays are high-pass filtered. At all other filter positions, the output x-ray spectrum is a mix of respectively low- and high-passed low and high kVp spectra. Integration of the x-ray flux occurs over the detector view period, and the changing spectra yields spectral blur and reduced high and low spectral separation. In some embodiments, maximum separation of the two GOLF output spectra is achieved by setting the filter displacement frequency to one-half of the detector view rate and aligning filter positions 1 and 5 with the start of low-kVp and high-kVp views, respectively.

In the embodiment of FIG. 3F, the absorption and filter gratings have the same spatial period, their duty cycles are both 50%, and the peak-to-peak filter displacement is ½ period. However, other duty cycles and peak-to-peak displacements are employed in other embodiments. Some kVp-switching systems may use longer view periods for the low-energy spectra and shorter ones for the high-energy spectra because x-ray tubes generate much less x-ray flux at low voltage than they do at high voltage for the same anode current. For such a system, some embodiments of the present invention include lengthened low-pass filter exposure and shortened high-pass exposure. View asymmetry in such embodiments can be accommodated by increasing the filter low-pass duty cycle from 50% and decreasing the absorption-grating duty cycle.

FIG. 3G further shows that, in some embodiments of the invention, spectral blur resulting from a sinusoidal filter motion can be reduced by decreasing the absorption-grating duty cycle. FIG. 3G shows an embodiment similar to that in FIGS. 3E-3F, but with a significantly reduced absorption-grating duty cycle. The filter grating and its sinusoidal peak-to-peak motion are unchanged in this embodiment. With a narrower absorption slit 104, the filter edges spend less time traversing the slits, meaning that each detector view period gets more time with correctly filtered x-ray flux. However, the absorption-grating output flux is directly proportional to the absorption grating duty cycle. Therefore, reducing the absorption grating duty cycle improves spectral separation at the cost of the total output flux.

Figure 4B:
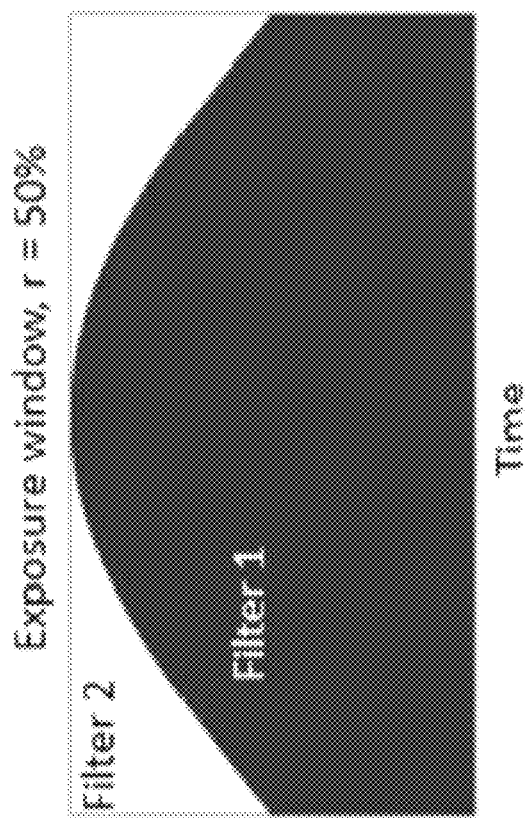
FIG. 4B shows the exposure window for two different types of filters of the same filter grating at a duty cycle of 50%, with the vibration amplitude being half of the filter grating period, according to an embodiment of the subject invention.
Figure 4A:
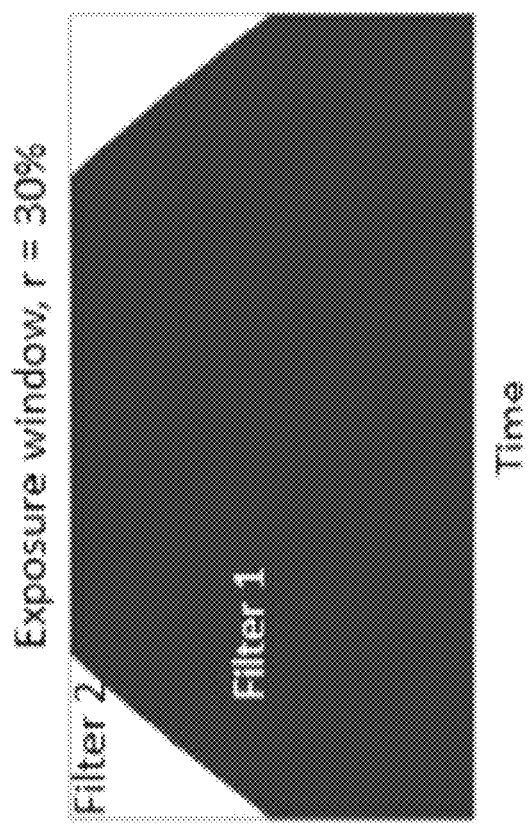
FIG. 4A shows the exposure window for two different types of filters of the same filter grating at a duty cycle of 30%, with the vibration amplitude being half of the filter grating period, according to an embodiment of the subject invention.
Figure 4C:
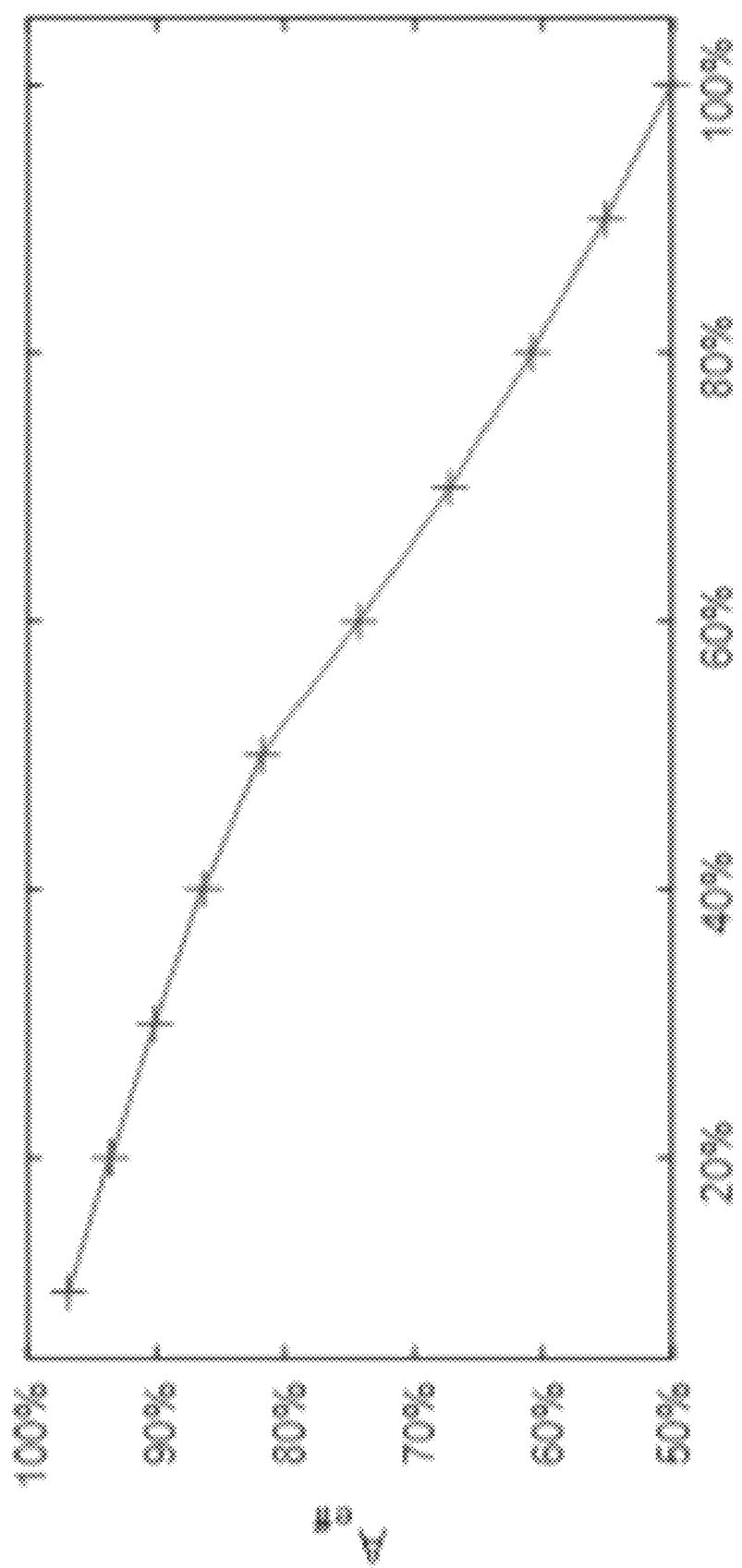
FIG. 4C shows a plot of effective filtration area (filter purity) for a two filter system as a function of absorption grating duty cycle (r).

FIGS. 4A-4B show the exposure window for two different types of filters of the same filter grating at duty cycles of 30% and 50%, respectively, for the vibration amplitude being half of the filter grating period. FIG. 4C shows a plot of effective filtration area as a function of absorption grating duty cycle (r). FIGS. 4A-4C are all for a $GOLF_k$ system/method according to an embodiment of the subject invention. Referring to FIGS. 4A and 4B, within the exposure window $\Delta t$, Filters 1 and 2 are gradually exposed through the absorption grating opening, in which Filter 1 offers the correct filtration, while Filter 2 introduces a contamination. Referring to FIG. 4C, by increasing the open ratio to 1, the filtration method is degraded to the conventional kVp-switching method.

Figures 4D, 4E:
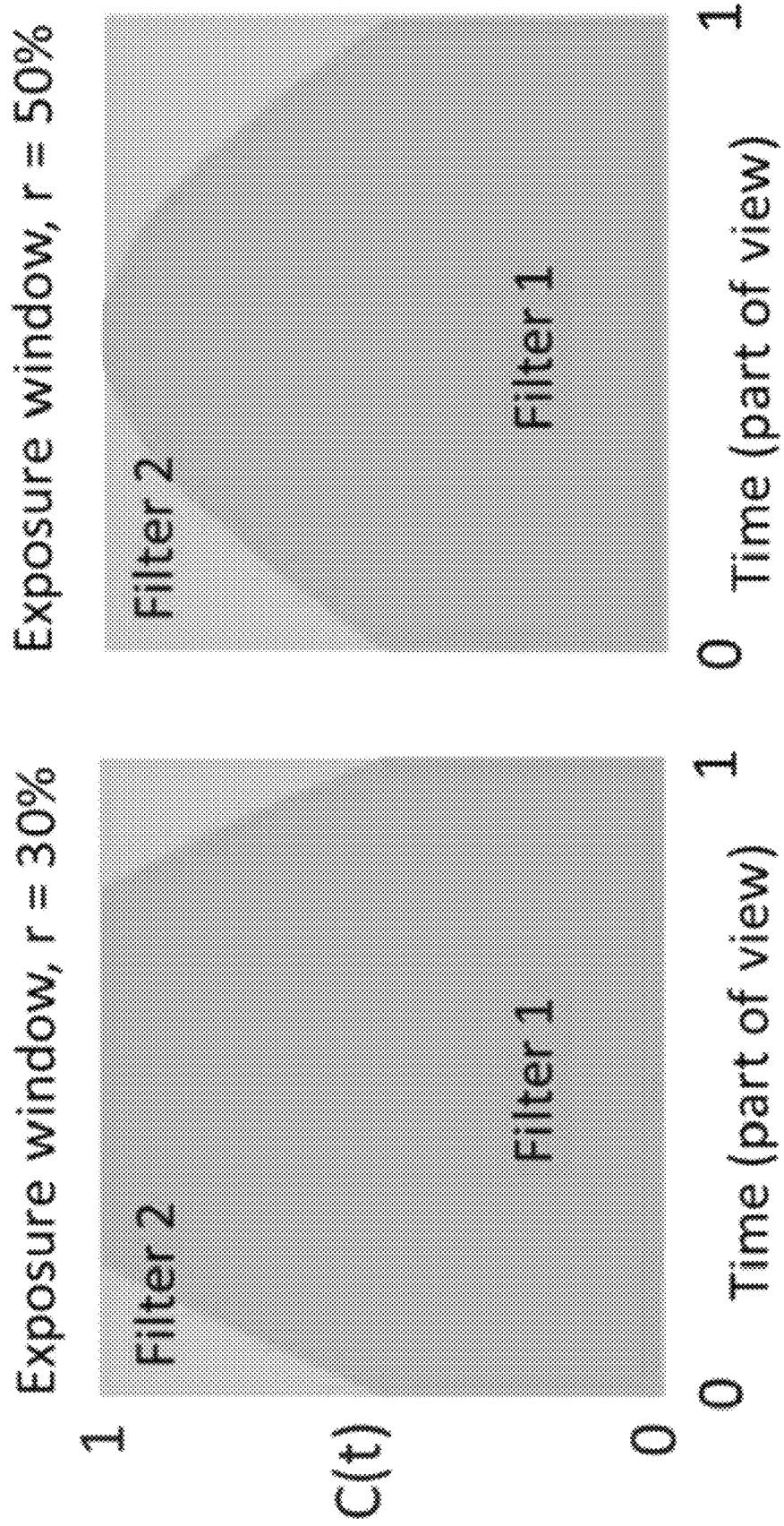
FIG. 4D shows an exposure window for absorption-grating duty cycle r=30% for the embodiment of FIG. 3G and sinusoidal filter motion.
FIG. 4E shows an exposure window for absorption-grating duty cycle r=50%, for the embodiment of FIG. 3G and sinusoidal filter motion
Figure 4F:
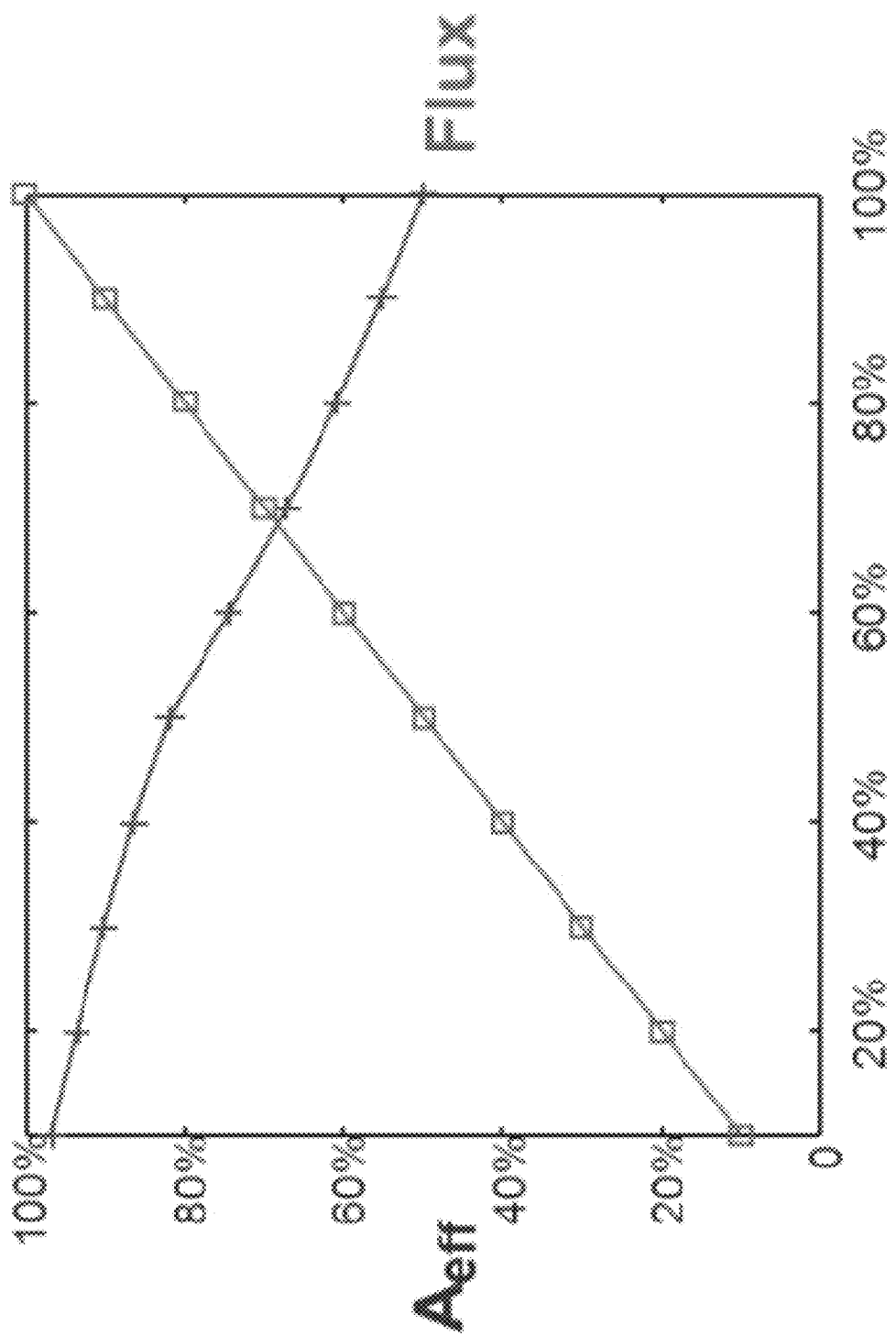
FIG. 4F shows a plot of the percentage of the desired filtration (cross-hatched) and flux efficiency (squares) as a function of the absorption-grating duty cycle, r.

FIGS. 4C-4E show how the absorption-grating duty cycle, r, affects the amount of spectral mixing during a view-period for the embodiment represented in FIG. 3G. FIGS. 4C and 4D show the "exposure window" for absorption-grating duty cycles of r=30% and r=50% respectively, where the exposure window plots the % correct filtering vs time, over one view period, and where filter 1 is the desired filter and filter 2 is the undesired filter . Let C(t) and W(t)=1−C(t) be the time dependent % slit coverage by the desired and undesired filters respectively. Also, let $S_T(E)$ be the energy-dependent (E) tube output spectrum during the view, $F_c(E)$ be the desired filter energy function, and $F_w(E)$ the undesired filter energy function. Note that C(t) depends only on the filter-motion as a function of time, which in this case is sinusoidal. The average spectrum over a view period, $\Delta T$, is then given by $$S_a(E)=S_T(E)[F_c(E)A_{eff}+F_w(E)(1-A_{eff})] \quad (1)$$

where $A_{eff}$ is the effective correct-filter time-slit area given by $$A_{eff} = \frac{1}{\Delta T}\int_0^{\Delta T} C(t)dt. \quad (2)$$

FIG. 4E shows how $A_{eff}$ (in %) depends on r when the motion is sinusoidal, and at the same time shows the flux efficiency. See that when r=50%, the output spectrum is the sum of 81% correctly filtered and 19% incorrectly filtered input spectra, and one half of the input flux is lost (absorbed). As r approaches 0, spectral filtering becomes perfect (no blurring), but the output flux goes to zero.

Figure 5A:
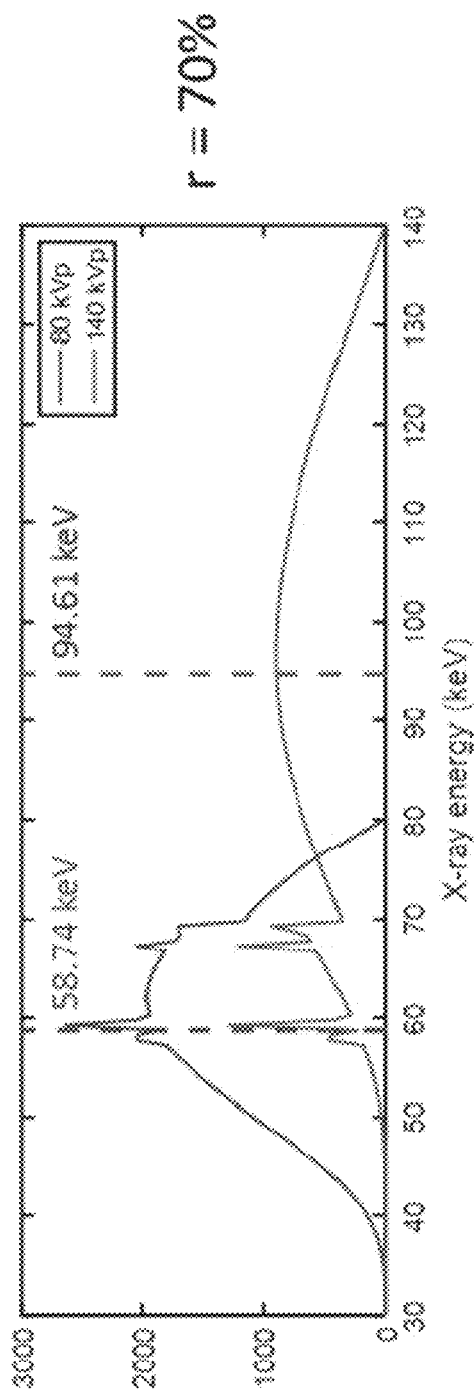
FIG. 5A shows a plot of dual-kVp spectral distributions after grating filtration using an absorption-grating duty cycle of 70%.
Figure 5B:
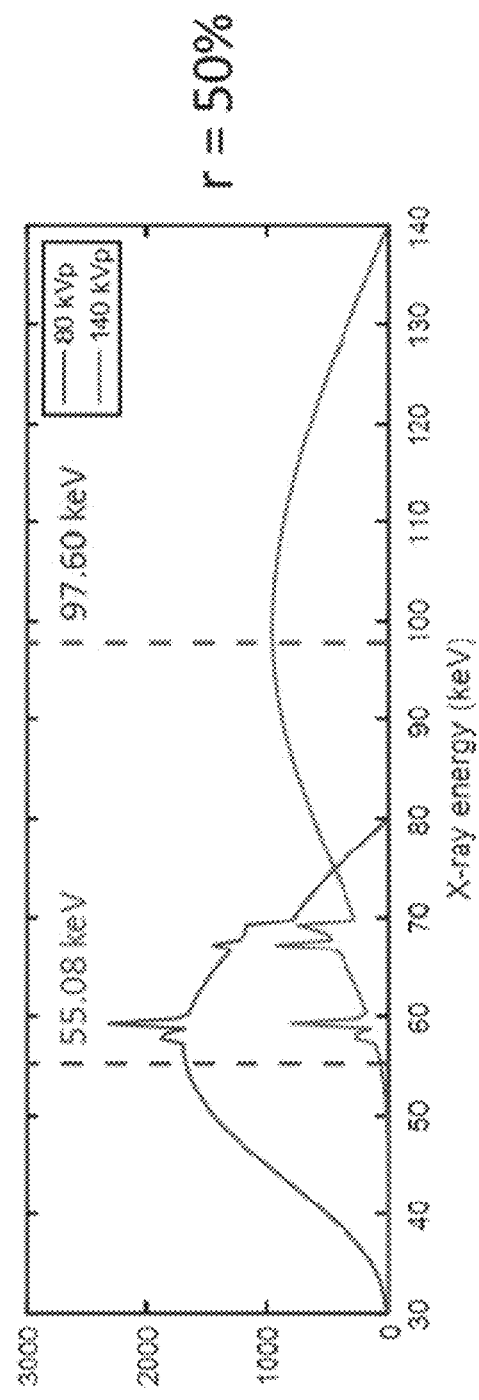
FIG. 5B shows a plot of dual-kVp spectral distributions after grating filtration using an absorption grating duty cycle of 50%.
Figure 5C:
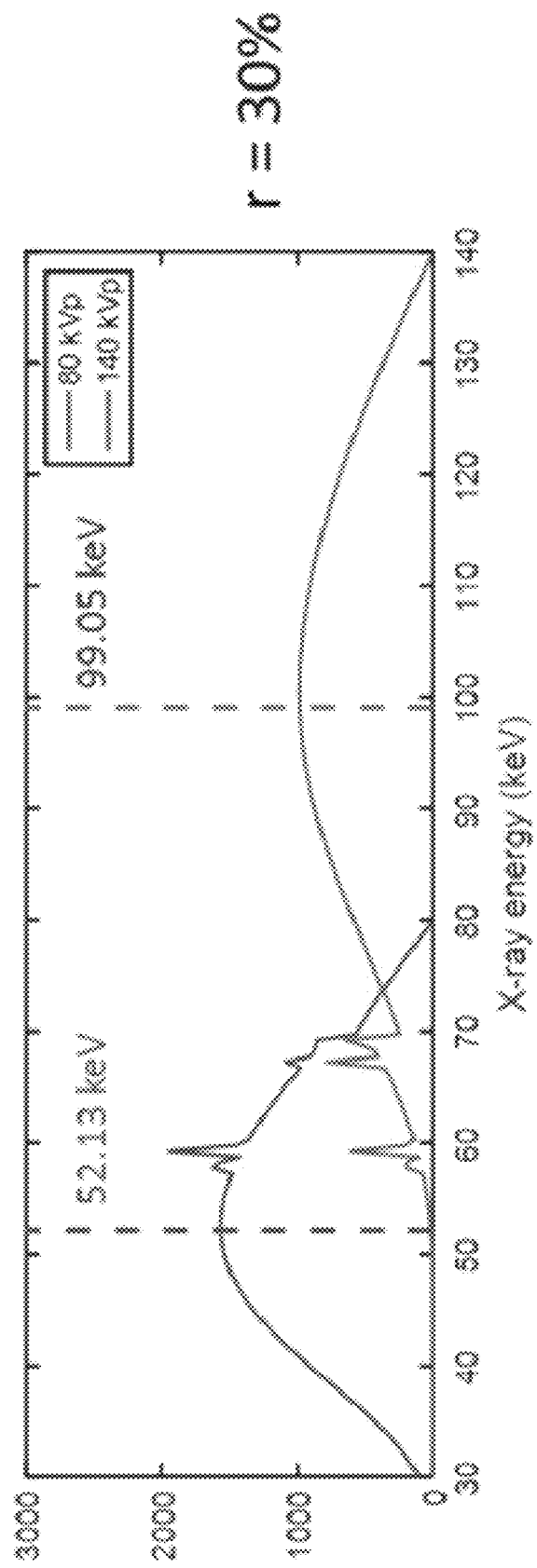
FIG. 5C shows a plot of dual-kVp spectral distributions after grating filtration using an absorption grating duty cycle of 30%.

FIGS. 5A-5C show plots of spectral distributions for a $GOLF_k$ system/method according to an embodiment of the subject invention, at absorption grating duty cycles of 70%, 50%, and 30%, respectively. In FIGS. 5A-5C, vertical dotted lines indicate corresponding mean energies (also labeled on the plots), and in each of these plots, the left-most plotted line is for an energy of 80 kVp and the right-most plotted line is for an energy of 140 kVp. The plots in FIGS. 5A-5C assume air and 1 mm tin as two filtering materials in the filter grating. Referring to FIGS. 5A-5C, a narrower absorption grating opening results in better separation of the spectra; though, a narrow absorption grating opening can decrease the X-ray efficiency. The output spectra (pre-patient) are calculated using Eqs. (1) and (2) above. In other embodiments, the low and high-pass filter materials are Air and 0.5 mm of Tin, respectively. In the embodiment shown in the Figures, the narrower absorption-grating slit (r=30%) yields largest mean-energy separation.

It is important to note that if grating vibration can be made more like a square wave, then, in some embodiments, the filter blurring can be avoided without having to reduce the absorption grating duty cycle. Also, in some embodiments, the x-ray source is rapidly pulsed during any view period. By properly phasing the source pulses with the filter positions, both the spectral separation and the flux efficiency of such embodiments can be improved. For example, staying with the 50% absorption grating in FIG. 3E, the source can be turned on at times 2 and 6, and turned off at times 4 and 8. This generates x-rays and illuminates the absorber slits only when the filter is mostly of one type.

In some embodiments of a vibrational GOLF system, the gratings are each a single continuous grating (not segmented), and the moved grating is planar and moved only in the plane. Gratings used in embodiments of the technology are designed to work with the large fan and cone angles of a CT system and, because the gratings have a significant thickness, they are "focused" on the source spot to avoid flux loss and spectral error. Although in some embodiments the stationary grating is curved, in other embodiments both gratings are planar and very close together to minimize alignment issues.

Figure 19:
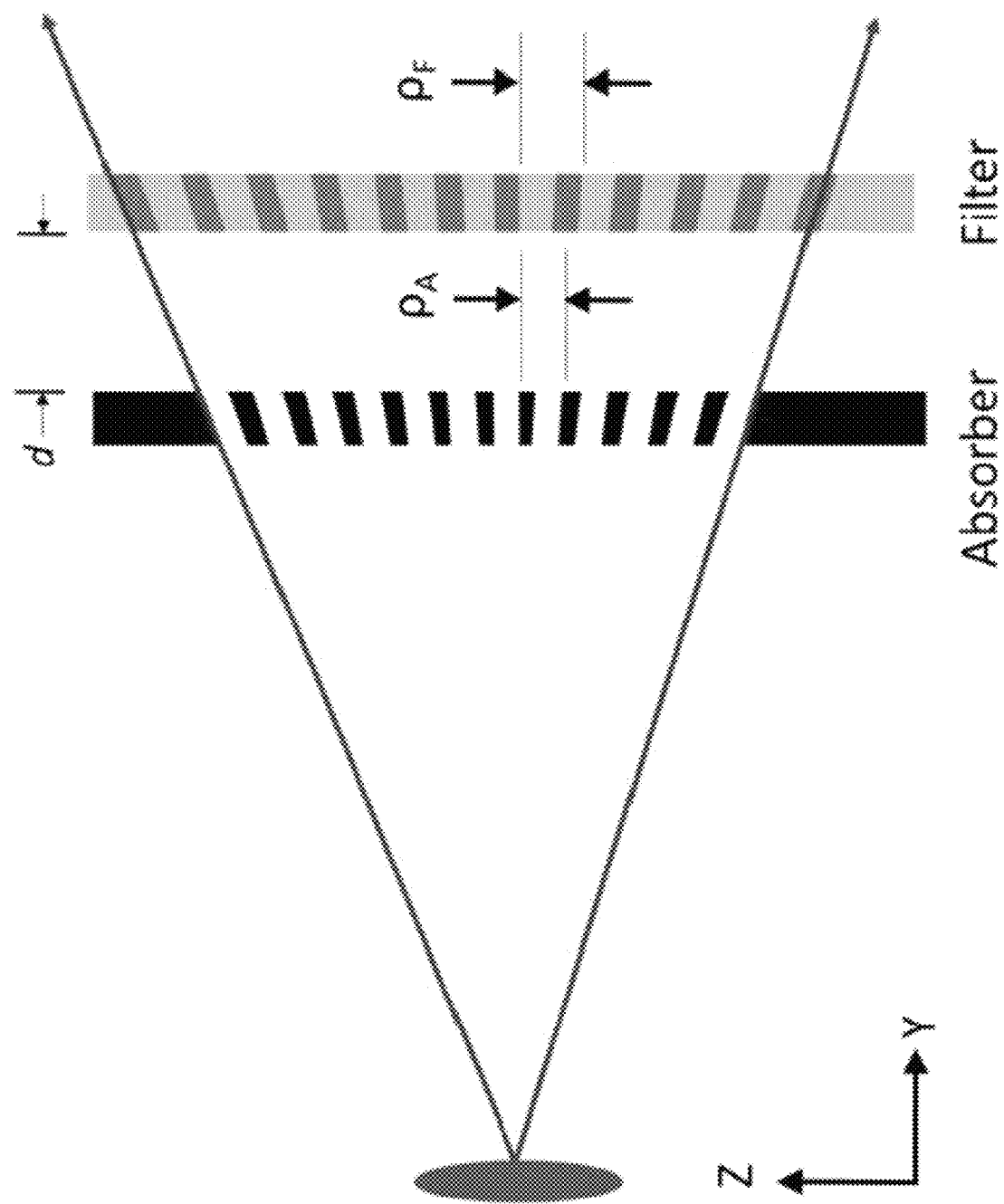
FIG. 19 shows an embodiment of planar absorption and filter gratings focused on a source of X-ray radiation.

FIG. 19 illustrates an embodiment of planar absorption and filter gratings focused on a focal spot. For good operation of some embodiments, the absorber and filter grating periods must be properly related for the given grating separation, d. For embodiments with small separation, the periods are nearly equal. Furthermore, for embodiments with small grating periods, the filter grating will remain in focus when it is shifted (vibrated) by only the required ½ period.

One exemplary embodiment includes the following design parameters: For a vibrational GOLF embodiment where r=50% as in FIG. 3E-3F, the key parameters are (1) absorption and filter grating materials and thicknesses, (2) grating period, and (3) distance of the gratings from the x-ray source spot. The absorber and filter materials and thicknesses are chosen to provide the required absorption and spectral filtration for the given source spectra. In an embodiment with a gold absorber for 80 and 140 kVp source spectra, a gold thickness of 0.5 mm would be sufficient to block at least 98% at all energy below 140 keV. In an embodiment with Air and Tin as filters, a filter-grating thickness of 0.5 mm will provide good spectral separation improvement.

Figure 20:
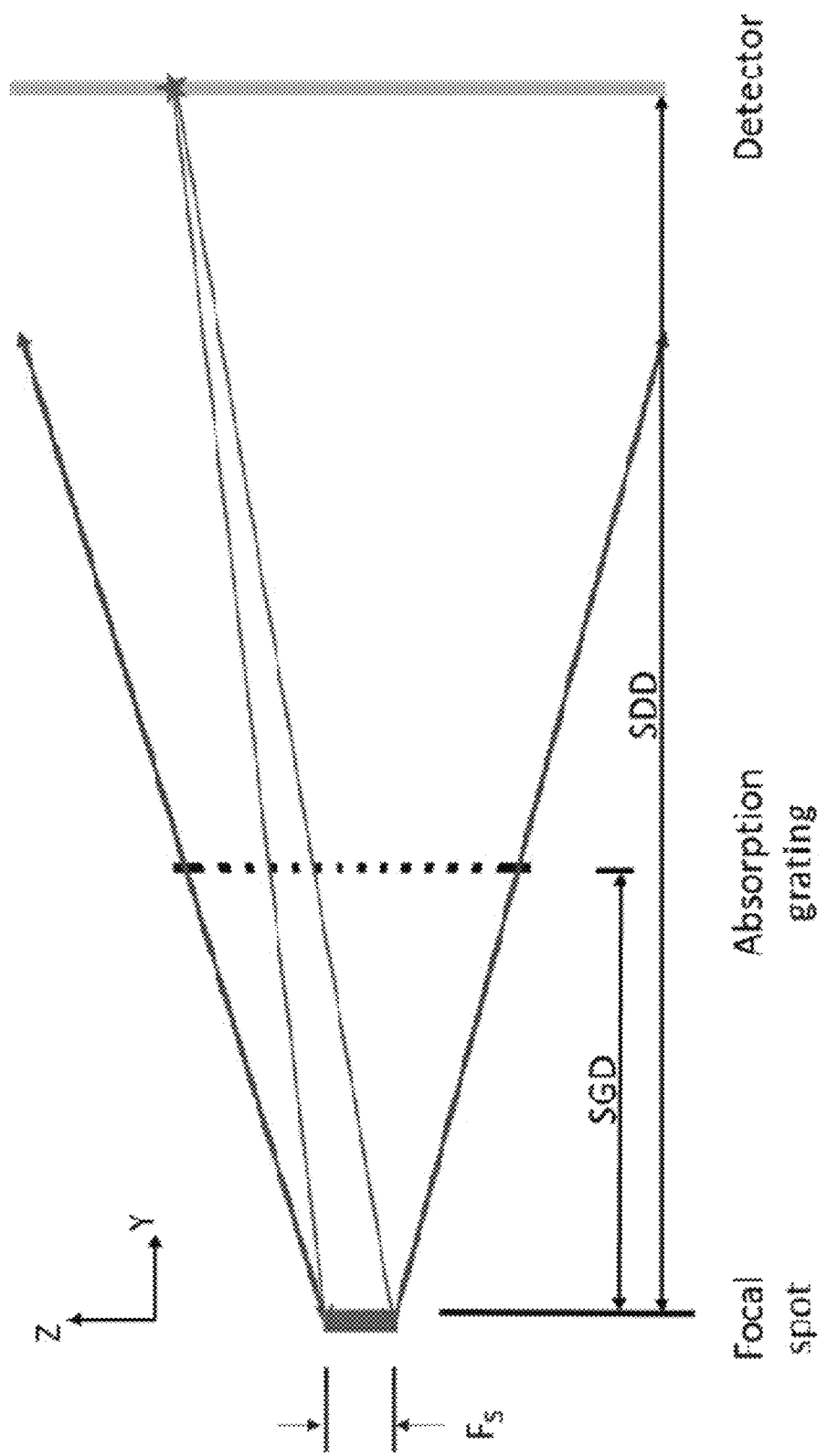
FIG. 20 shows the geometric optics for source focal spot blurring of the absorption-grating image at a detector.

For some embodiments of vibrational GOLF, the grating period must be small enough to allow the rapid filter displacement but not so small that the grating cannot be fabricated or mechanically stabilized. Furthermore, it must not be too large relative to the source-spot size because the absorption grating bars would cast undesirable non-uniform (pixel-location-dependent) shadows on the detector (although they can be corrected), or for very large bars, completely block some detector pixels. FIG. 20 shows the source spot, absorption grating and detector relevant geometry. The extended spot size will beneficially blur the image of the grating on the detector in some embodiments, and the grating period can be chosen to insure little or no grating visibility in the detector image. Grating-induced flux variation across the detector is avoided if the focal-spot size Fs, the source-to-grating distance SGD, the source-to-detector distance SDD, and the absorber grating period $\rho_A$ are related by $$\rho_A = \frac{1}{n} F_S \left(1 - \frac{SGD}{SDD}\right) \quad (3)$$

where n is a positive integer. With planar gratings and a planar detector array, every detector pixel has the same ratio SGD/SDD. When Eq. (3) is satisfied, every detector pixel gets the same percentage of flux blocked by the grating. That is, if Eq. (3) is satisfied and the grating duty cycle of 50% is used, then exactly ½ of the focal spot is blocked by the absorption grating for every point on the detector. When Eq. (3) is not satisfied, there is grating-induced flux variation across the detector array. As the integer n grows larger, the grating-induced variations diminish even when Eq. (3) is not satisfied. If necessary, this variation could be allowed to remain and be accounted in the common CT air and spectral calibrations.

From the perspective of diffractive optics, there is virtually no x-ray diffraction from the gratings. The diffraction for an x-ray of wavelength $\lambda$ from an open slit of width L (L>>$\lambda$) is a sinc$^2$ function with maximum at $\theta$=0 (straight through, no bending) and first zeros at the positive and negative angles where $$|\text{Sin}\,\theta| = \frac{\lambda}{L} \quad (4)$$

For 30 keV x-rays, $\lambda$=4.13E-10. With an open slit width of 50 um, Eq. (4) gives the diffraction as bounded between +/−8.26E-6 radians. Thus, all x-ray energies above 30 keV stays within +/−8.26E-6 radians on leaving any slit larger than 50 um. Therefore, x-rays continue straight through the slit and, with an SDD of only ~1 meter, there is little interaction with radiation from other slits.

Exemplary approximate parameter values for a typical CT machine are: SDD=0.9 meter, FS=0.8 mm and a spot-to-tube-window distance of ~65 mm. According to some embodiments, the GOLF gratings are to be placed close to the source but outside of the x-ray tube (in other embodiments, they are in the x-ray tube), and an additional 10 mm to get SGD ~75 mm. With these values, Eq. (3) says that grating periods of 0.733, 0.367, 0.244, 0.183, 0.147, and 0.122 mm (for n=1 through 6, respectively) will yield no visible grating shadows on the detector. With thicknesses of 0.5 mm for a Gold absorption grating, and 0.5 mm for a Tin filter grating, it is feasible to choose the n=3 result above and use a grating period of 0.244 mm. This choice yields an absorption-grating thickness/width ratio of ~4 for the slits for an exemplary embodiment. As shown in FIGS. 3E-3F, the filter grating would then need to be vibrated with a peak-to-peak amplitude of 0.122 mm.

Figures 21A, 21B:
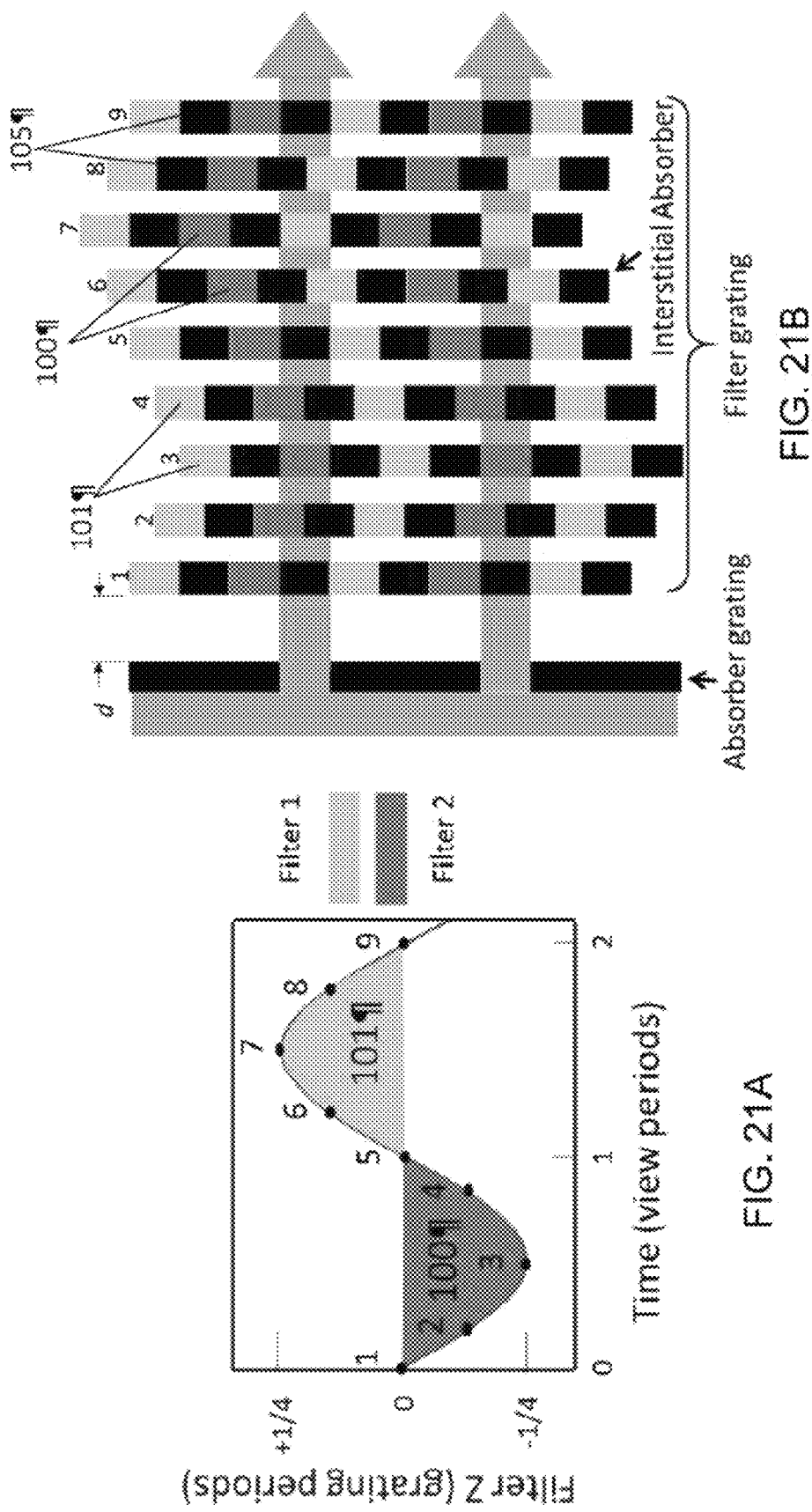
FIG. 21A shows a plot of the flux output and filter type vs time for the arrangement shown in FIG. 21B.
FIG. 21B shows a schematic view of a sequence of filter Z-axis positions of a vibrating filter grating with interstitial absorbers for the labeled times in FIG. 21A.

In an alternative embodiment of a vibrational GOLF system, interstitial absorbers 105 added to the filter grating reduce the mixing of the filter types 100, 101 during each view period. FIG. 21A shows a plot of the filter Z position and filter type vs time for the filter grating movement and relationship to the X-ray beam shown schematically in FIG. 21B. FIG. 21B shows the numbered grating positions that correspond to the numbered points along the curve plotted in FIG. 21A. In this embodiment, the absorbers placed between the different filter stripes allow only one filter type to be active in any absorber-grating slit at a time. In embodiments with improved spectral purity, the slits in the absorber grating must not be larger than the absorbers in the filter grating. In embodiments using sinusoidal vibration without pulsing the x-ray source, flux efficiency of 15.9% when the absorber-grating duty cycle is 25% is achieved in some embodiments.

In some embodiments that include "interstitial" absorbers, a set of absorbing regions 105 are positioned between each neighboring, alternating filter region 100, 101. In such arrangements, the set of filter regions 100 of the first type (e.g., low-pass filter regions) are positioned so that each alternates with each filter region of the set of filter regions 101 of the second type (e.g. high-pass filters), and the absorbers 105 are positioned between each individual filter region. As described herein, each of the two sets of filter regions produce different X-ray spectra from the X-ray radiation.

An embodiment of a "vibrational" GOLF module according to the present technology that includes PZT actuators and power amplifiers will now be described. This embodiment also includes a Tin filter grating that is 0.5 mm thick, has a 50% duty cycle and 0.244 mm period, and is located 75 mm from the source spot. The filter grating is vibrated with a peak-to-peak (p-p) amplitude of one half of the grating period, or ~120 um at a 1 kHz rate. This embodiment includes a Kinetic Ceramics A050120 PZT actuator, which provides a maximum displacement of 120 um when 1000 V is applied. It has a self-resonant frequency of 12.3 kHz and, with light loading, it supports 1 kHz sinusoidal operation with 120 um p-p displacement.

The forces required to vibrate the filter grating are calculated as follows. If the filter is placed 75 mm from the source in a 64-slice CT machine with a fan angle of 57 degrees and a cone angle of 4 degrees, then the filter grating must be approximately 82 mm in X and 6 mm in Z to filter the entire beam. The filter volume is then 246 mm$^3$, half Air and half Tin. With the density of Tin at 7.31 g/cm$^3$, the resulting mass is only 0.9 grams. Providing another ~10× mass for filter stiffening/stability, the mass to be vibrated is ~10 grams. With sinusoidal vibration, the filter position, velocity, and acceleration are given by $$d(t) = D_{peak} \sin(2\pi f t) \quad (5)$$

$$v(t) = 2\pi f D_{peak} \cos(2\pi f t) \quad (6)$$

$$a(t) = -(2\pi f)^2 D_{peak} \sin(2\pi f t) \quad (7)$$

where $D_{peak}$=60 um so that the peak acceleration is 2.4E+03 m/s$^2$. The peak force required for this acceleration of ~10 grams is 24 Newtons. This is very small compared to the actuator blocking force of 4500 N (Newtons) such that the actuator can achieve the desired 120 um of displacement at ~1000 V.

Figure 29A:
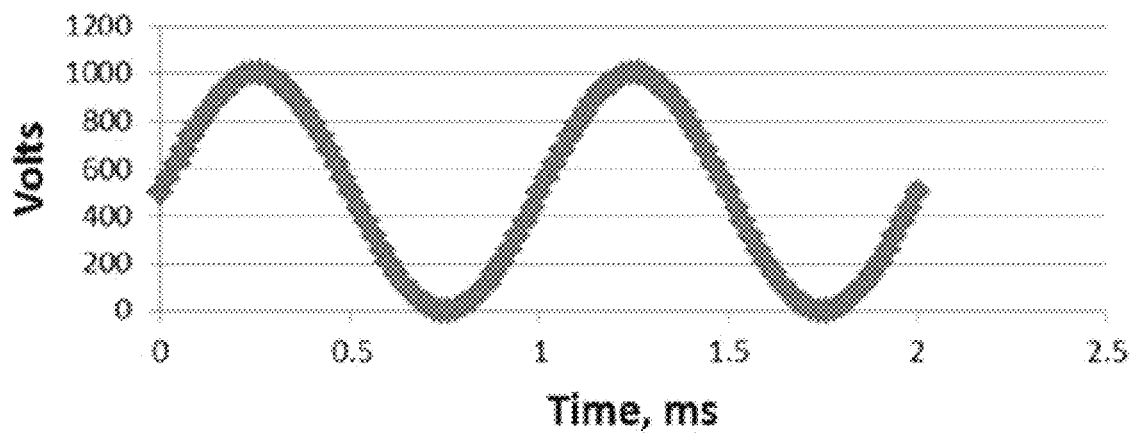
FIG. 29A shows the voltage waveform for driving the Kinetic Ceramics A050120 PZT actuator in an embodiment of the invention.
Figure 29B:
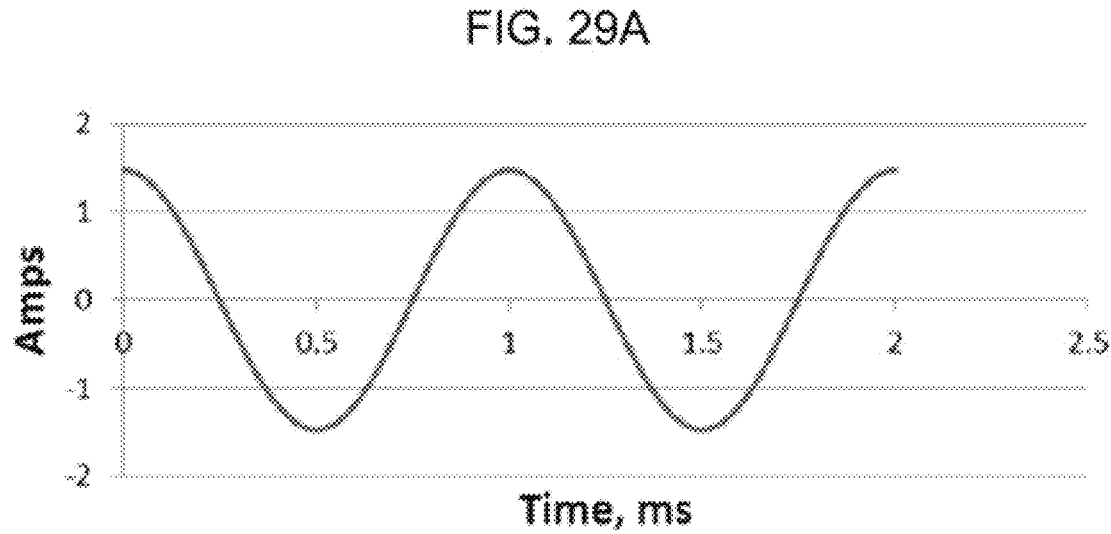
FIG. 29B shows the current waveform for driving the Kinetic Ceramics A050120 PZT actuator in an embodiment of the invention.
Figure 29C:
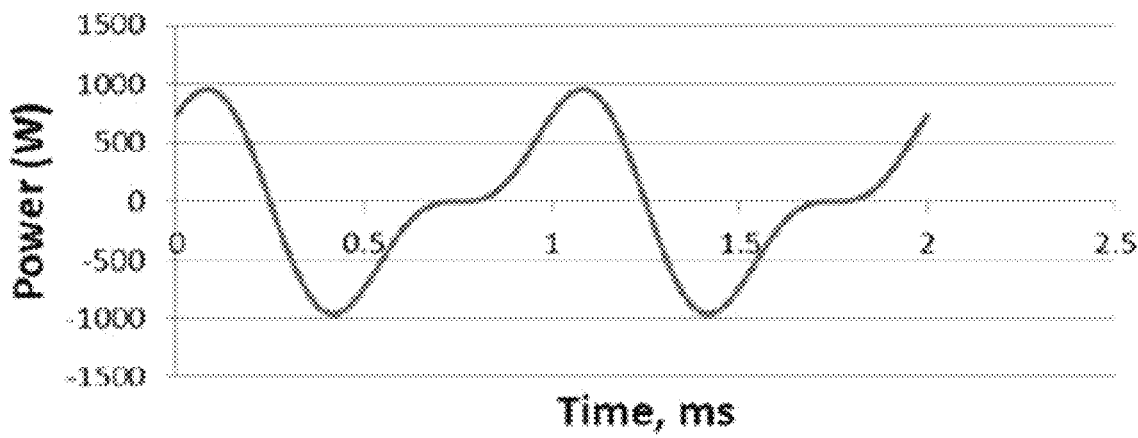
FIG. 29C shows the power waveform for driving the Kinetic Ceramics A050120 PZT actuator in an embodiment of the invention.

The voltage and current required for sinusoidal displacement are expressed as $$V(t) = \frac{500 D_{peak}}{120} [1 + \sin(2\pi f t)] \quad (8)$$

$$I(t) = \frac{2500 \, C f D_{peak}}{120} \cos(2\pi f t) \quad (9)$$

where $D_{peak}$ is in microns and cannot exceed 120, f is in Hz and should be well below the self-resonant frequency, and C=1.18 uF is the PZT stack capacitance for the Kinetic Ceramics A050120 actuator. The resulting voltage and current waveforms are shown in FIGS. 29A-C. The instantaneous power required is the product of the voltage and current, as shown in FIG. 29C. The average power required is zero because the energy is alternately stored in and then removed from the actuator capacitance. However, a controller capable of sourcing and sinking 1 kW is needed.

In some embodiments of vibrational GOLF systems, steps are taken to prevent the vibration from coupling to other CT system components (the tube, etc.) and/or making offensive audible noise. One method to reduce unwanted coupling is to incorporate a counter-weight in the GOLF module so the net momentum of the GOLF module is zero. In some embodiments, the absorption grating makes an effective counter weight. To maintain the filter-grating character during vibration, one or more of a parallel stiffening plate, captivating travel tracks, and mode dampening methods are used in some embodiments to avoid travelling waves and/or out of plane vibrations within the grating. While some embodiments use linear grating slits and bars, other embodiments use a checkerboard grating to reduce unwanted vibration modes by reducing long unsupported regions of absorbing bars within the grating.

In some embodiments, it is desirable to avoid the relatively rapid grating oscillation required in some vibrational GOLF to achieve a filter change with each view. In some alternative embodiments, a planar filter grating is used that is longer than the x-ray beam footprint in one dimension, and the grating is slid at a constant speed in that one dimension during a scan. In some embodiments, the part of the filter grating that is interacting with the x-ray radiation is moved in substantially only one direction during operation of the source. In some embodiments, the only one direction is a linear dimension. In other embodiments, such as some described below, the only one direction is rotation about an axis.

FIG. 22 shows a schematic representation of an embodiment in which a constant-velocity sliding filter grating is employed and a source that is constantly on. The gratings in this embodiment shown in FIG. 22B are the same as those employed in the embodiment shown in FIG. 21B, but the constant velocity yields the triangular flux output function shown in FIG. 22A. As shown, the filter grating is moved toward the top of the page of FIG. 22 (increasing Z). The sliding motion is synchronized with the detector view rate so that filtration alternates view by view. The filter grating is both periodic and focused at infinity so that, from the source point of view, all integer period translations are indistinguishable. The grating filter is slid in the Z (cone angle) direction because, with CT, this direction has the least angle change across the beam footprint. The maximum flux efficiency for this embodiment is 12.5% with a source that is constantly on.

Figure 23B:
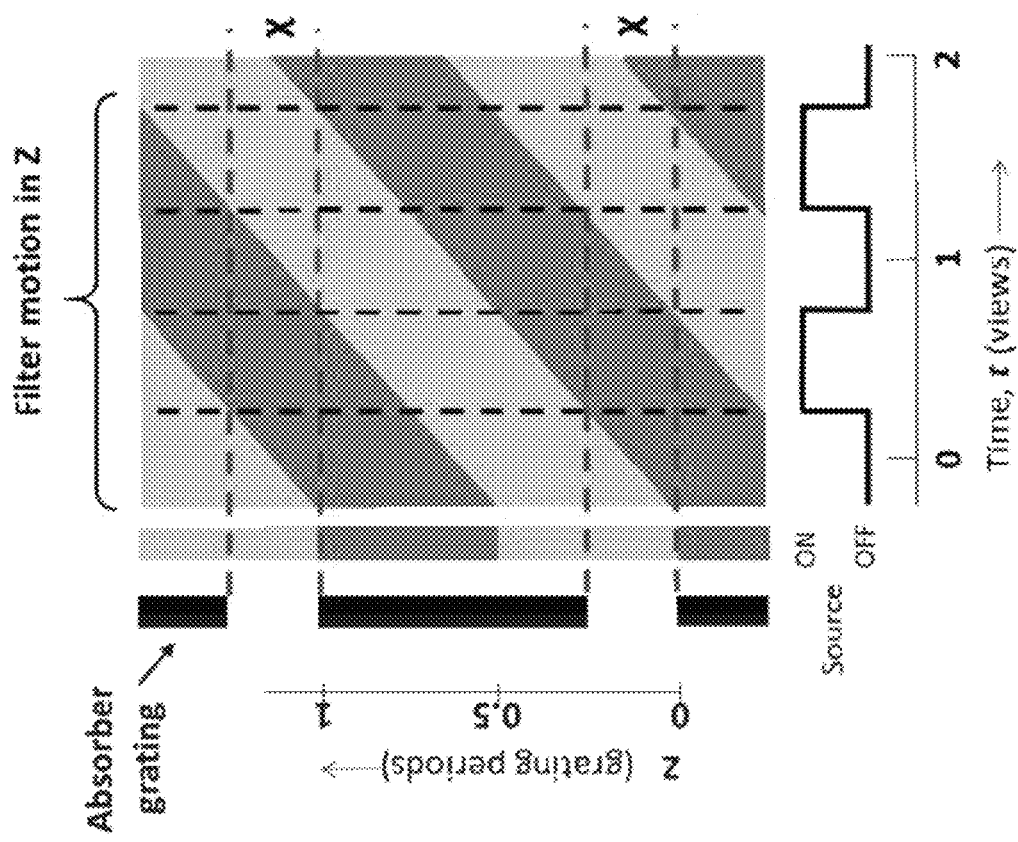
FIG. 23B shows a schematic view of a filter grating with constant-velocity movement along the Z-axis and source that is pulsed.
Figure 23A:
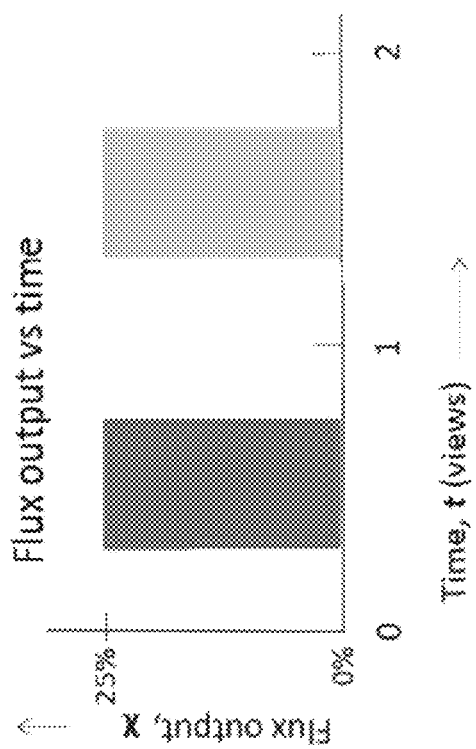
FIG. 23A shows a plot of the flux output and filter type vs time for the arrangement shown in FIG. 23B

FIG. 23 shows a schematic view of a constant motion grating used with a pulsed source. In embodiments that include this arrangement, half of the flux waste associated with the triangle slopes in FIG. 22A can be eliminated as shown in FIG. 23. In some embodiments with the arrangement shown in FIG. 23, the source is enabled only while a single filter type spans all absorber-grating slits. This helps maintain spectral purity even in the absence of interstitial filter absorbers present in other embodiments. Flux efficiency for this embodiment is 25%.

For embodiments in which the filter grating is moved relative to the absorption grating in only a single direction such as those shown in FIGS. 22 and 23, long scans require the filter to either be long or to reverse its direction during a scan. In embodiments in which the direction of movement of the grating is reversed, suitable motors and actuators are included in the system. Similarly, embodiments that include a rigid scan-length filter grating require accommodating room inside the CT machine.

In other embodiments, however, a flexible filter grating "tape" is used. The filter grating is moved relative to, and in some cases across, the absorption grating and is collected on reels, similar to traditional flexible film used for movies. In some such embodiments, therefore, the flexible filter grating is attached to a reel, which is driven by an actuator or motor to take up the flexible filter grating at the desired speed. The portion of the grating that interacts with the x-ray radiation will thereby move in a single direction relative to the absorption grating while the source is in operation.

In other embodiments, the absorption grating is moved relative to the filter grating. Similarly, the absorption grating is moved in only a single direction in some embodiments, in ways similar to those discussed above with respect to the filter grating.

Figure 24:
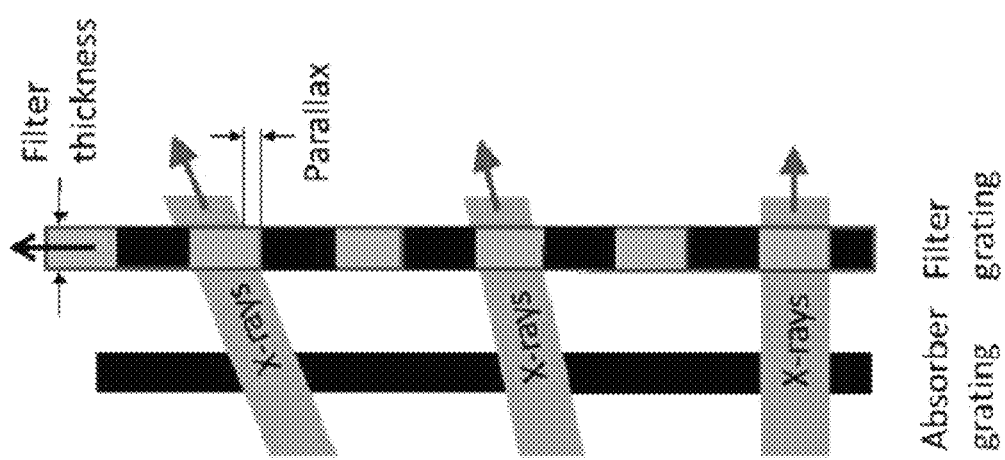
FIG. 24 shows a schematic view of the effect of parallax on an embodiment of the present invention in which planar gratings are employed.

FIG. 24 shows a schematic view illustrating the effect of parallax encountered at large cone angles with embodiments of the invention that utilize "planar" gratings, including single direction sliding GOLF systems. Parallax causes extra flux loss that can be accounted in CT calibration, but large parallax could completely block all x-rays. The flux loss can be reduced by increasing the grating period while holding the filter thickness constant. The parallax Z-width at a cone angle θ is given by $$W_m = abs(T_F \tan \theta) \quad (10)$$

For an exemplary 64-slice CT with SDD=900 mm, SGD=75 mm, Fs=0.8 mm, $T_F$=0.5 mm, r=25%, and a cone beam of +/−2°, the parallax Z-width $W_m$=0.0175 mm. For x-rays at the edge of the cone, this is about ¼ of the absorber grating slit width if the grating period $\rho_A$ is 0.244 mm. The resulting non-uniform cone illumination can be accounted as part of the system calibration. For a 1000-view scan, the filter length would have to be 122 mm.

Figure 25:
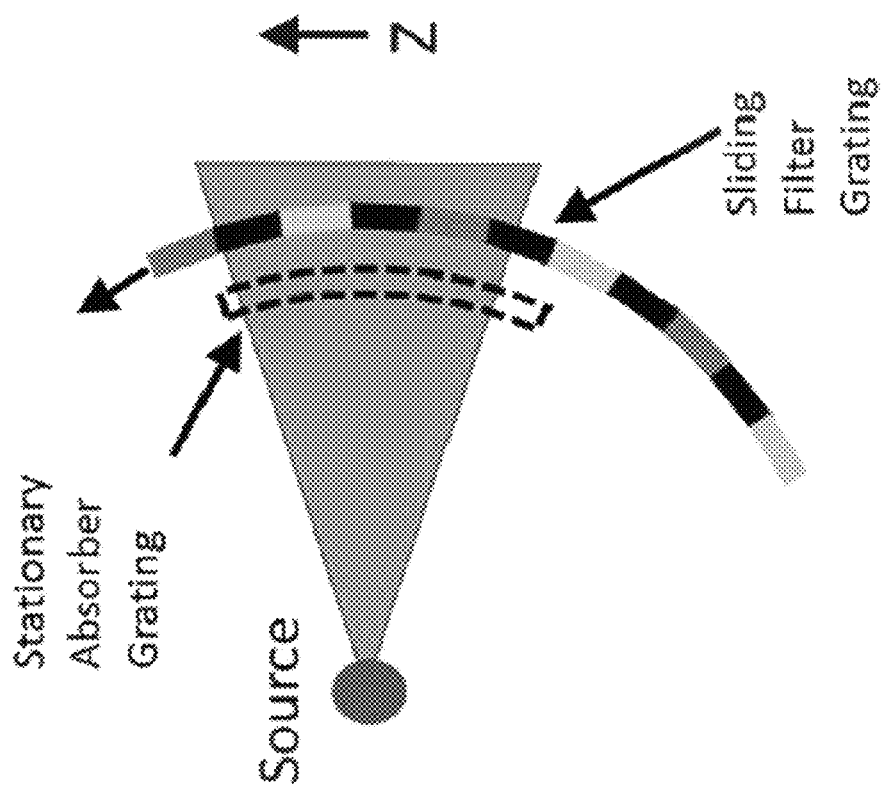
FIG. 25 shows a schematic cross-section view of cylindrically curved gratings in a system according to an embodiment of the invention.

In another alternative embodiment, curved gratings are used. In one such embodiment, cylindrically curved absorption and filter gratings are used, as shown in FIG. 25. In the embodiment depicted, the axis of the cylinder is a line containing the source point and is parallel to the fan (x) direction, which extends into and out of the page. In this embodiment, the absorption-grating and filter-grating edges are axially oriented, such that the gratings are in focus across the entire beam footprint. In this embodiment, the curvature of the absorption grating and the curvature of the filter grating are concentric to each other with respect to the x-ray source.

In some embodiments utilizing curved gratings, the filter grating is rigid and slid around the curved movement path. In other embodiments, the filter grating is flexible and uses reels in a manner similar to the manner described above. In some such embodiments, the flexible filter grading is slid against the curved stationary absorber grating. Some embodiments using curved gratings use a pulsed source to improve the flux efficiency, as shown in FIG. 23. Embodiments with curved gratings help address the issue of the effect of parallax. As a result, the grating period can be made smaller to allow for shorter sliding travel in such embodiments. FIG. 25 also shows the use of interstitial absorber regions in the curved filter grating, which function in a manner similar to that described above with respect to interstitial absorbers in planar gratings.

Figure 26:
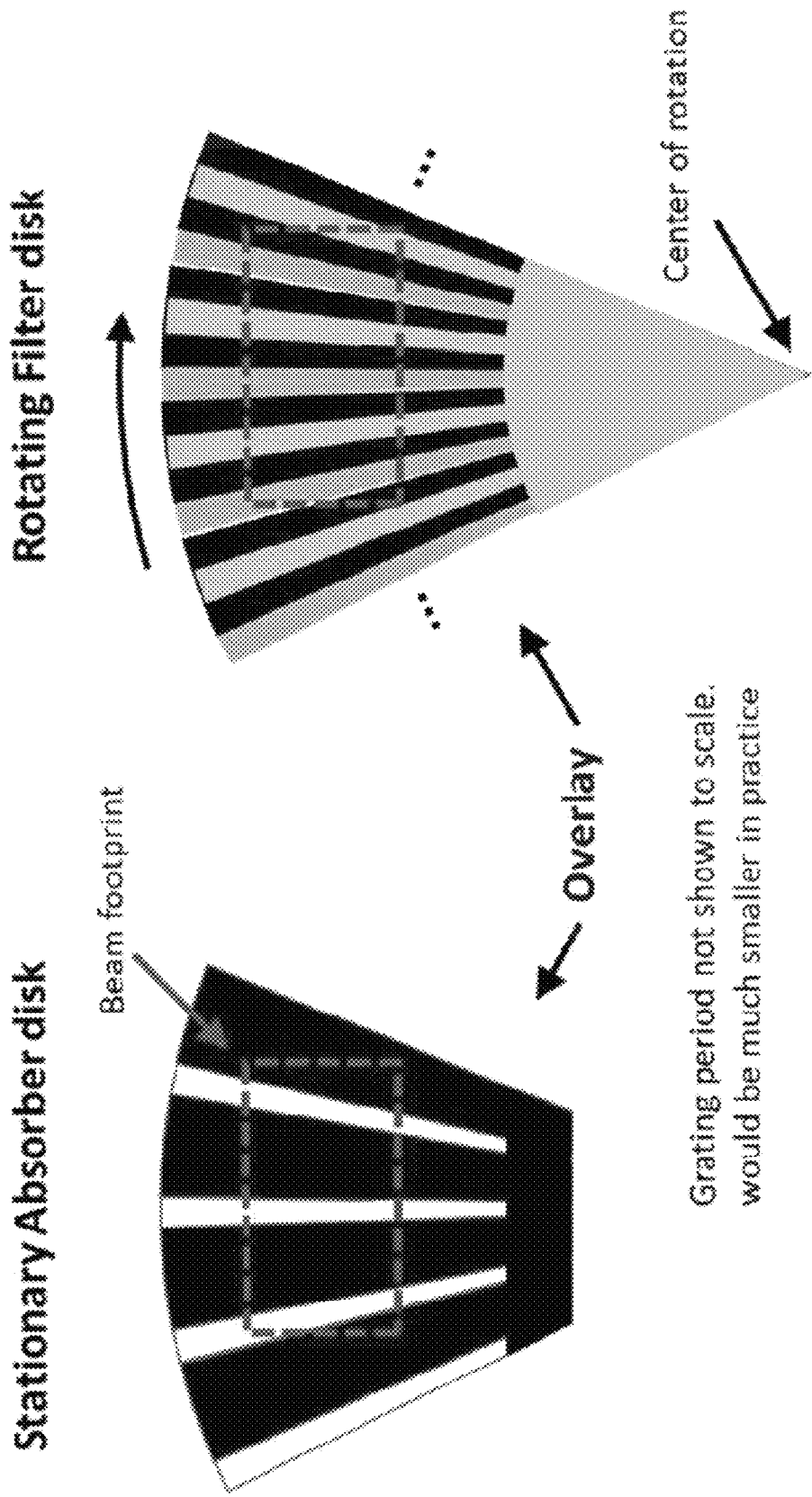
FIG. 26 shows a schematic view of spherical grating sections flattened to a plane.
Figure 27:
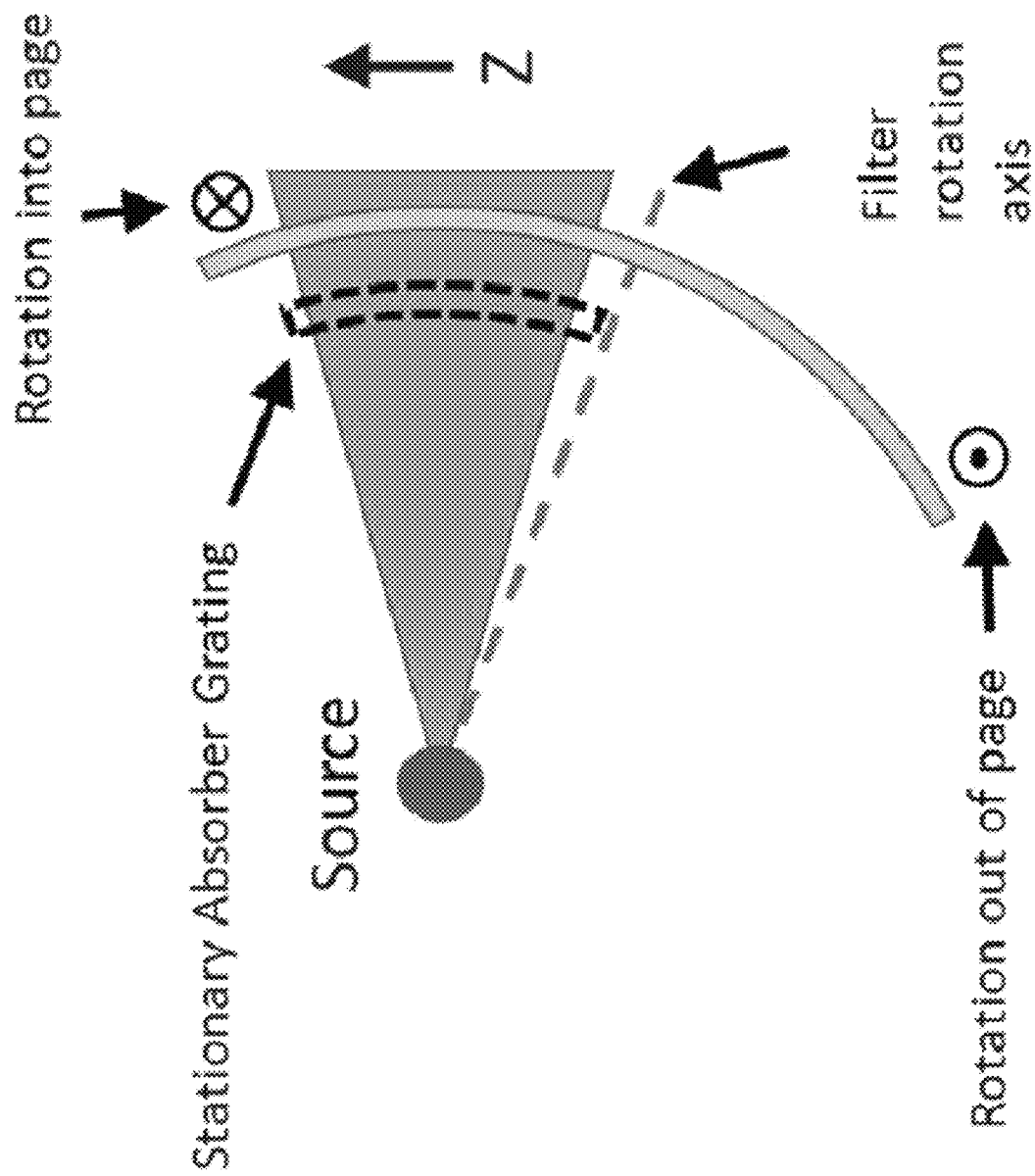
FIG. 27 shows a schematic cross-section view of spherically curved gratings in a system according to an embodiment of the invention.

Another alternative embodiment utilizes spherically curved gratings. In some such embodiments, a spherically shaped stationary absorber-grating section and a relatively slowly rotating spherically shaped filter-grating section are used, as shown in FIGS. 26 and 27. FIG. 26 shows a surface view of the two grating sections flattened to disks for illustration. FIG. 27 shows a side view of how the spherical sections are positioned relative to the source in this embodiment. The two gratings are radially oriented with a constant angular grating period and overlaid with their radial centers aligned. Only the filter section is rotated, and its center of rotation is placed outside the beam footprint, in this embodiment. In this embodiment, long CT scans are possible with no aberrated views in embodiments in which the entire filter grating has an integer number of grating periods. The grating patterns in this embodiment are relatively simple and permit the entire beam footprint to experience the same filtration at any time. Some embodiments that utilize spherically curved gratings benefit from significant performance improvements: issues associated with vibrations, linear translations, parallax, and limited scan times are significantly reduced or avoided.

In other embodiments that utilize spherically curved gratings, the absorber and filter spherical sections use a radial checkerboard pattern, where the absorber and filter grating patterns in FIG. 26 are divided into separate rings, and the rings are phase-shifted relative to each other.

FIG. 26 shows a filter grating with interstitial absorbers for improved spectral purity, but, in other embodiments, the interstitial absorbers are not used so as to increase the flux efficiency where a pulsed source is used. The description above in connection with FIGS. 22 and 23 are also applicable to embodiments in which grating rotation is used. One key advantage for spherical, rotating gratings, however, is that all points on the absorber and filter gratings are in focus (no parallax) in some embodiments. However, in embodiments with conventional CT system detectors, there is no source-to-grating distance (SGD) that will satisfy Eq. (3) for the entire beam footprint because the (Cartesian) grating period grows with radius. The angular grating period should then be chosen small enough for acceptably low grating image visibility from any part of the grating in the x-ray beam.

The size of the rotating filter is described by the spherical angle it spans, and it is desirable to choose a size that has acceptable grating slit widths. As an example, let λ be the chosen Z-direction offset of the filter rotation axis from the beam footprint center and, from Eq. (3), choose a filter grating period of $\rho_{Fmax}$=0.244 mm at the corner of the beam footprint furthest from the filter rotation center. Furthermore, to seek the filter spherical span angle and offset λ that insure the minimum grating period over the beam footprint, $\rho_{Fmin}$, is no smaller than $\rho_{Fmax}/2$=0.122 mm. Using spherical trigonometry it can be shown that if b=7° is the half-cone span, d=29° is the half-fan span, and the filter surface is placed 75 mm from the source spot, then a spherical filter section with a half-span of 45° and surface radial length of 59 mm will yield $\rho_{Fmin}$=0.122 at the edge of the footprint closest to the filter rotation center. These values are then subtly adjusted to make an integer number of periods in one filter rotation. With an outer-edge grating period of 0.244 mm and 2 views per grating period, a 1000 view scan requires 122 mm of rotation at the filter outer edge, or 149 degrees per 1000 views. A CT view rate of 3000 views per second would require this filter to spin at only 1.25 revolutions per second. By maintaining contact between the absorber and rotating filter gratings, susceptibility to gantry or tube vibrations would be minimized.

In some embodiments of the present invention, the spherical gratings are portions of hemispheres—that is, less than half a sphere. The size of the sections is chosen to work with the particular system or CT machine at issue. In some embodiments, the rotating grating rotates about an axis that runs from approximately the location of the x-ray source to the approximate center of the spherical grating section.

In some embodiments, the use of spherically curved gratings is another embodiment in which one of the gratings is moved in only a single direction relative to the other grating (i.e., one of clockwise or counterclockwise rotation of a grating). In some embodiments, the filter grating is rotated. In other embodiments, the absorber grating is rotated. In other embodiments, a grating is rotated back and forth between two rotational directions.

Figure 6A:
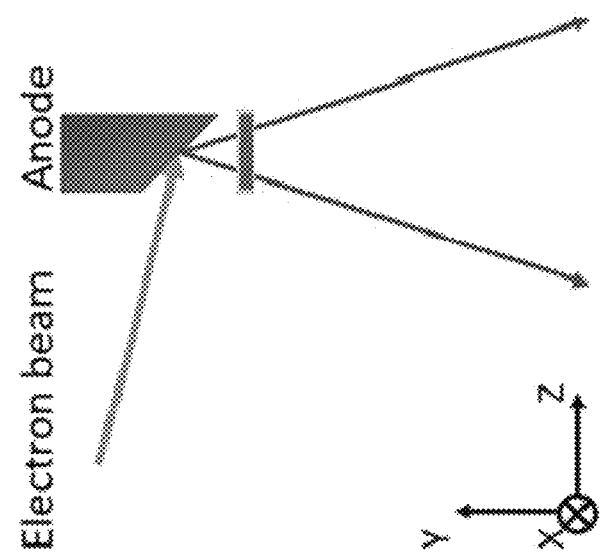
FIG. 6A shows a top schematic view of a setup according to an embodiment of the subject invention.
Figure 6B:
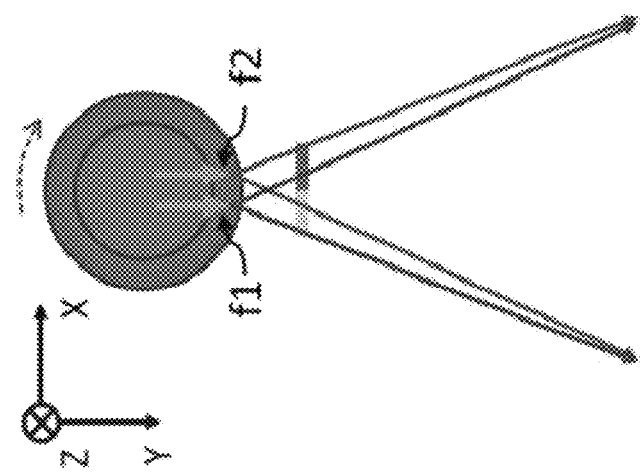
FIG. 6B shows a top schematic view of a setup according to an embodiment of the subject invention.
Figure 6C:
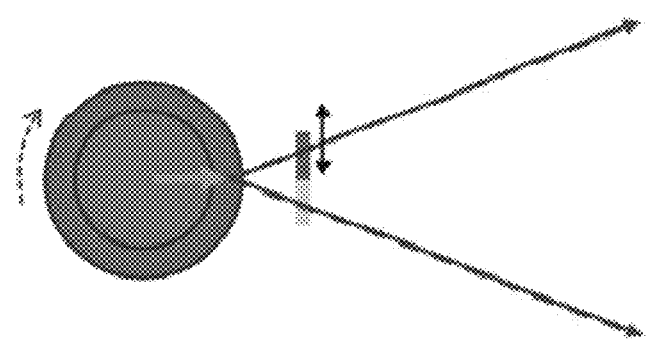
FIG. 6C shows a top schematic view of a setup according to an embodiment of the subject invention.
Figure 6E:
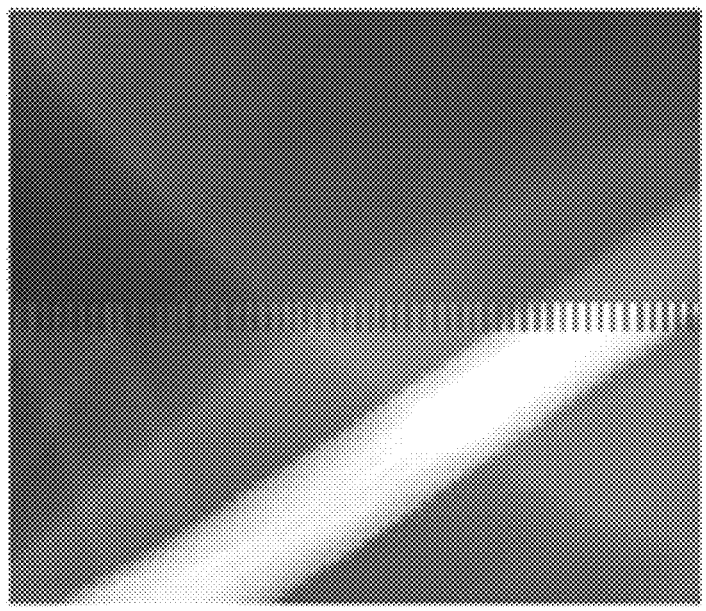
FIG. 6E shows an image of collected data for a CT scan.
Figure 6D:
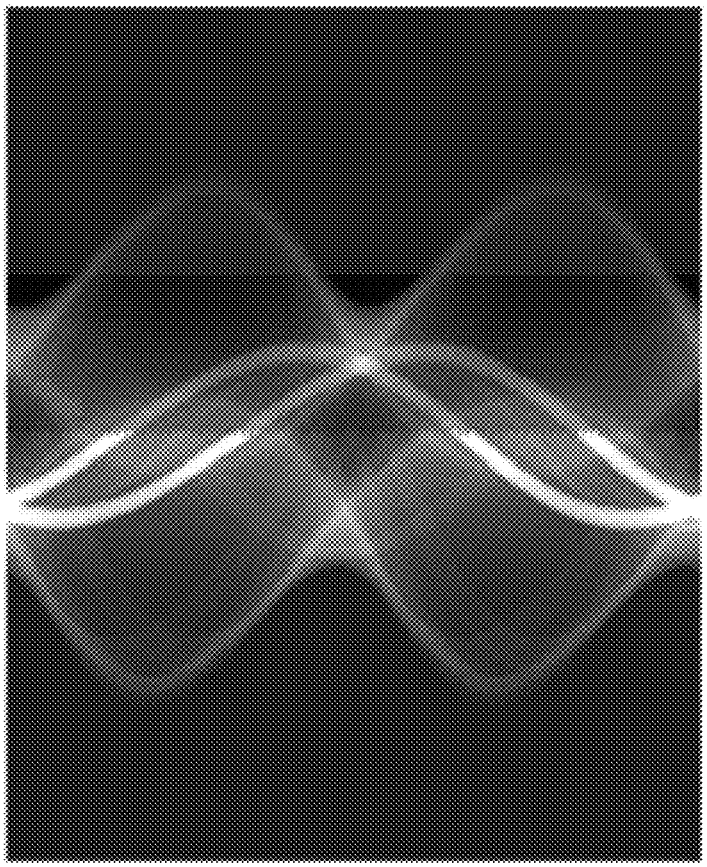
FIG. 6D shows a collected CT sinogram.

$GOLF_c$ and $GOLF_s$ systems and methods as described herein can be used with an X-ray source with no kVp-switching (and, optionally, without any other advanced features). FIGS. 6A-6C show top schematic views of a $GOLF_c$ setup according to various embodiments of the subject invention. The X-ray sources shown in FIGS. 6A-6C are for exemplary purposes only and should not be construed as limiting. In an embodiment, a degraded grating filter can include only two filter strips, one of which is low-absorption material (e.g., air or aluminum) and the other is a high-absorption material (e.g., tin). The low-absorption material can keep the original X-ray beam while the high-absorption material can harden the X-ray beam (see also FIGS. 6A-6C). With this $GOLF_c$ setup, two mean-energy parts can be formed in one full X-ray beam. FIG. 6D shows the collected CT sinogram, in which the left side is low mean-energy data, and the other side high mean-energy data, which are for low-energy and high-energy image reconstruction, respectively. Given the size of the X-ray focal spot, a penumbra can be seen along the middle line of the sinogram, as marked by the (red) arrow in FIG. 6D, which will influence the image reconstruction. To address this effect, relative displacement between the X-ray focal spot and filter grating can be introduced. It can be implemented, for example, via e-beam control in the X-ray tube (the flying focal spot method) or filter oscillation outside the X-ray source; these two methods are equivalent in principle.

In a specific embodiment of $GOLF_c$, the low- and high-absorption materials can be 0.1-mm and 1.0-mm tin materials, respectively, and the size of the X-ray focal spot can be 1 mm. In this case, the penumbra in the detector plane is about 8 mm in width under the imaging geometry of a system in which the filter is 10 cm away from the X-ray focal spot. By controlling the X-ray focal spot flying in 1 mm along the X-axis or oscillating the filter with 1 mm peak shift, the collected data are shown in FIG. 6E, which can remove the penumbra effect although the amount of effective central data are reduced by half. As a result, the middle strip in FIG. 6D can become usable after longitudinal data interpolation for dual-energy image reconstruction via filtered back projection (see, e.g., references [20] and [21] in the References section, both of which are hereby incorporated herein by reference in their entireties).

Figure 7A:
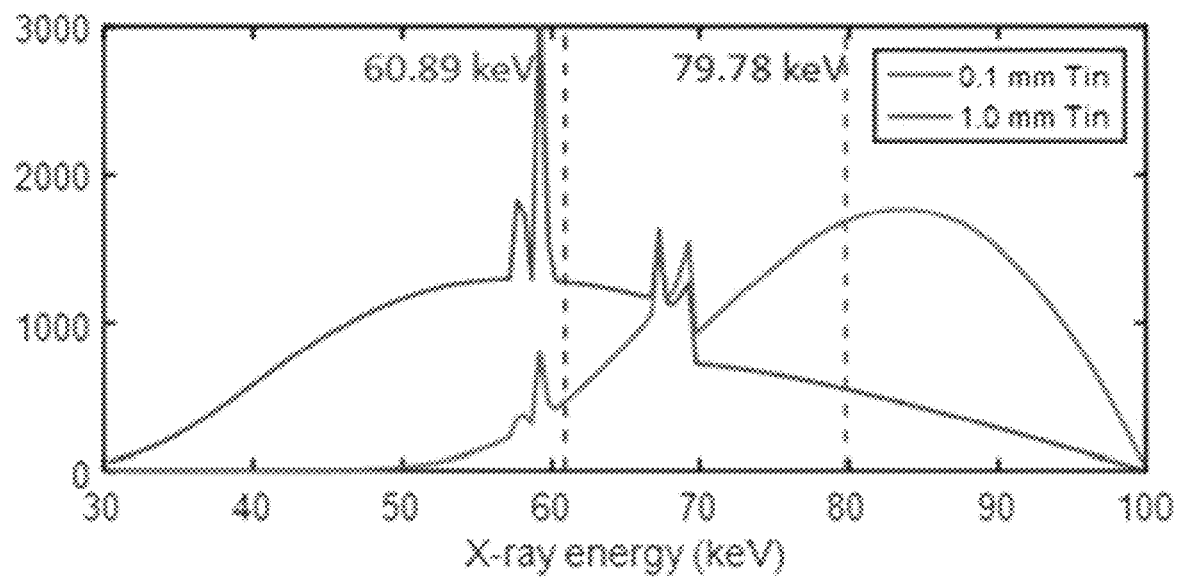
FIG. 7A shows a plot of spectral distributions for a two-strip grating.
Figure 7B:
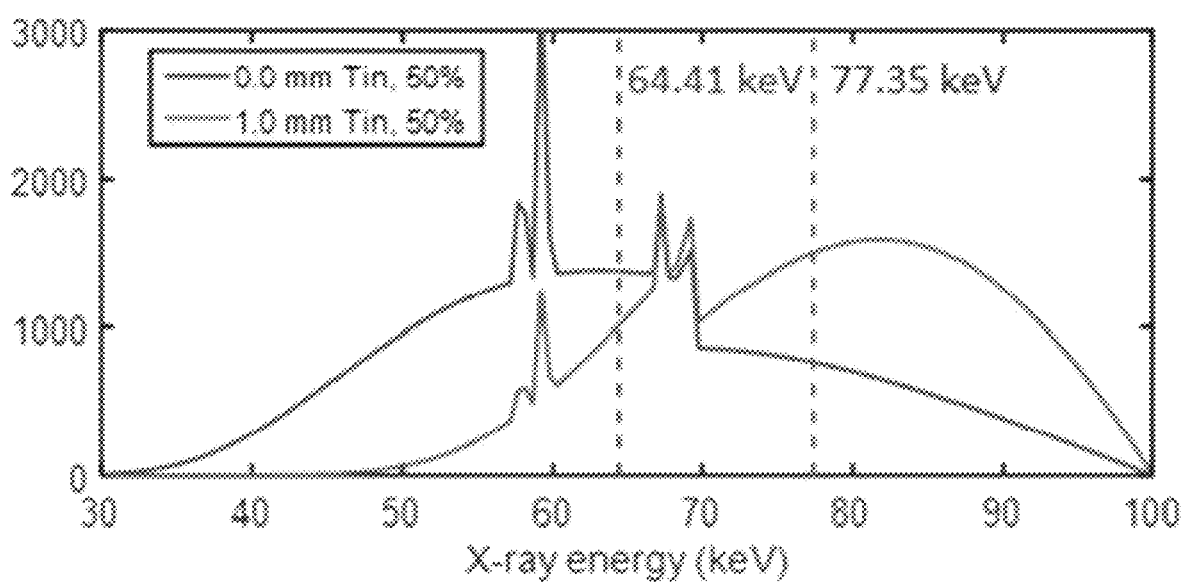
FIG. 7B shows a plot of spectral distributions for a multi-strip grating.

FIGS. 7A and 7B show plots of spectral distribution for a $GOLF_c$ setup for a two-strip grating and a multi-strip (more than two-strip) grating, respectively, according to an embodiment of the subject invention. To obtain the plots in FIGS. 7A and 7B, the two types of filtering materials were 0-mm titanium (air) and 1.0-mm titanium materials. In FIGS. 7A and 7B, vertical dotted lines indicate corresponding mean energies (also labeled on the plots), and in each of these plots, the right-most plotted line is for 1.0 mm tin (50% duty cycle in FIG. 7B). In FIG. 7A, the left-most plotted line is for 0.1 mm tin, and in FIG. 7B, the left-most plotted line is for 0.0 mm tin at 50% duty cycle. More generally, in $GOLF_c$ the two-strip filter can be replaced by a grating comprising alternating strips, coupled with an absorption grating as described with reference to $GOLF_k$. With this grating method, the relative displacement between the X-ray focal spot and the filter grating is not needed because the motion of the absorption grating defines the filtration for the X-ray beam. However, the drawback of the grating method is its low X-ray flux efficiency. FIG. 7B is based on a multi-strip grating including 0-mm titanium (air) and 1.0-mm titanium materials with a duty cycle of 50%.

The $GOLF_c$ systems and methods described herein can be used with a conventional X-ray source that does not include kVp-switching, thereby relaxing the need for a kVp-switching X-ray source. However, dynamic relative grating displacement can still be used to select X-ray filtration effects. The dual-energy imaging system can be further simplified with a stationary filtering grating alone or just a stationary two-strip filter where an X-ray imaging model is necessary to separate mixed spectra for hybrid imaging reconstruction (see also, e.g., reference [22] in the References section, which is hereby incorporated herein by reference in its entirety). The stationary filtering grating methods can be referred to as "$GOLF_s$".

A monochromatic image can be reconstructed in both the projection and image domains (see, e.g., references [8] and [23] in the References section, both of which are hereby incorporated herein by reference in their entireties). This is based on the assumption that any material can be represented as a linear combination of two basis materials:

$$\mu^i = \left(\frac{\mu}{\rho}\right)_1^i \rho_1 + \left(\frac{\mu}{\rho}\right)_2^i \rho_2, i = L, H \tag{11}$$

where "L" and "H" indicate low- and high-energy, respectively, and "1" and "2" indicate the two basis materials, respectively. Mass densities ($p_1$, $p2$) of the two basis materials are used to characterize any material. In the projection domain (p) and image domain (μ), there are low- and high-energy datasets and images ($p^L$, $p^H$ and $\mu^L$, $\mu^H$). The monochromatic image CT(E) at any x-ray energy E can be reconstructed from projections.

$$P(E) = w(E) \cdot P^L + (1-w(E)) \cdot P^H \tag{12}$$

Specifically, $$CT(E) = \text{recon}(P(E)) \tag{13}$$

and $$CT(E) = w(E) \cdot CT^L + (1-w(E)) \cdot CT^H \tag{14}$$

where the weighting factor is $$w(E) = \frac{\mu_1(E) \cdot \mu_2^H - \mu_2(E) \cdot \mu_1^H}{\mu_1^L \cdot \mu_2^H - \mu_1^H \cdot \mu_2^L} \cdot \frac{\mu_2^L}{\mu_2(E)}. \tag{15}$$

Systems and method of embodiments of the subject invention, in combination with single-kVp imaging and kVp-switching technology, open new doors to extract dual energy data effectively, with flexibility, and improved costeffectiveness. The key feature of dual-energy CT imaging is the spectral separation that helps avoid spectral mixing and reveals more information regarding material composition and monochromatic imaging. Systems and method of embodiments of the subject invention can take advantage of these attributes of dual-energy CT imaging while also addressing the motion artifact problem with a dual-source scanner and the spectral overlapping problem with kVp-switching and dual-layer detection systems.

Three main types of GOLF systems and method have been described, including $GOLF_k$, $GOLF_c$, and $GOLF_s$. $GOLF_k$ performs the best in terms of spectral separation, and a combination of absorption grating(s) and filter grating(s) can be used with a single-source CT system to achieve dual-source, dual-energy CT performance similar to that in a $GOLF_c$ system/method. When a kVp-switching X-ray source cannot be used, a $GOLF_c$ or $GOLF_s$ system/method can be used to significantly improve spectral separation. $GOLF_s$ can be thought of as the simplest case of $GOLF_c$ with the highest photon utilization. $GOLF_s$ can work in a stationary mode with only one filter grating, for example in a full scan. The image reconstruction algorithm for $GOLF_s$ can be based on a non-linear X-ray data generation model.

Embodiments of the subject invention can include dynamically modulating the filter grating of millimeter-/sub-millimeter-sized filtering strips by a matching absorption grating with a small oscillation amplitude at a high frequency. Due to this micro-technology, the medical CT requirements for full coverage over the field of view and a rapid change in filtration settings can be simultaneously achieved to yield superior spectral filtration. The filter vibration can be driven by, for example, a piezo-electrical device, which is a mature technology compatible with CT scanning. The same is true for embodiments involving translation (in a single direction during source operation) or rotation of the filter and/or absorption grating. The use of an absorption grating does result in the loss of some X-ray flux from the source. The duty cycle of the absorption grating can balance the X-ray spectral separation and the X-ray flux utilization. If the duty cycle of the absorption grating is 100% (r=100%), the system is equivalent to a conventional kVp-switching based dual-energy CT; while as r gets closer to 0, spectral separation gain is increased while more X-rays are blocked (X-ray flux decreases). Better spectral separation (narrower opening slits) leads to better quality of reconstructed monochromatic images without having to increase the radiation dose to which the patient (e.g., a mammal such as a human) or subject is exposed during imaging.

For high-power CT scans such as a 100 kW scan, embodiments that use a pulsed x-ray source are desirable, since this can cut wasted flux in half. The absorption grating does not increase the patient radiation dose. Some embodiments of the invention increase spectral separation and CNR/dose ratio of kVp switching to that of the state of the art dual-source CT system while avoiding dual-source system cost and temporal mismatch issues.

In $GOLF_s$ systems and methods according to embodiments of the subject invention, a filter grating can be used with no absorption grating, thereby not completely blocking the path of any X-rays. The image reconstruction from data collected with $GOLF_s$ can be more complicated, involving non-linear data modeling and compressed sensing (see also reference [22] from the References section, which is hereby incorporated herein by reference in its entirety). Spectral mixing in multiple penumbras could be an issue.

It is emphasized that in addition to the explicitly described designs, many variations are possible in the spirit of the invention. For example, the gratings can be made in 2D instead of 1D (e.g., to fit into cone-beam geometry). Also, more than two filtering material types can be introduced (e.g., for multi-energy x-ray imaging). Also, X-ray path lengths in the patient body can be taken into account so that the final diagnostic performance can be optimized instead of the spectral separation itself, which is an indirect measure anyway.

Embodiments of the subject invention can advantageously be used with existing X-ray CT systems with minimal overhead expense. Piezoelectric devices and narrow grating period allow embodiments of vibrational GOLF systems to be implementable with the high oscillation frequency needed for modern single-source CT scanners. The imaging performance can be improved significantly in terms of monochromatic image quality, material decomposition, and radiation dose reduction. Although the use of an absorption grating can decrease the efficiency of the X-ray source, patient radiation dose is not increased, so this is not a major drawback.

The methods and processes described herein can be embodied as code and/or data. The software code and data described herein can be stored on one or more machine-readable media (e.g., computer-readable media), which may include any device or medium that can store code and/or data for use by a computer system. When a computer system and/or processor reads and executes the code and/or data stored on a computer-readable medium, the computer system and/or processor performs the methods and processes embodied as data structures and code stored within the computer-readable storage medium.

It should be appreciated by those skilled in the art that computer-readable media include removable and non-removable structures/devices that can be used for storage of information, such as computer-readable instructions, data structures, program modules, and other data used by a computing system/environment. A computer-readable medium includes, but is not limited to, volatile memory such as random access memories (RAM, DRAM, SRAM); and non-volatile memory such as flash memory, various read-only-memories (ROM, PROM, EPROM, EEPROM), magnetic and ferromagnetic/ferroelectric memories (MRAM, FeRAM), and magnetic and optical storage devices (hard drives, magnetic tape, CDs, DVDs); network devices; or other media now known or later developed that is capable of storing computer-readable information/data. Computer-readable media should not be construed or interpreted to include any propagating signals. A computer-readable medium of the subject invention can be, for example, a compact disc (CD), digital video disc (DVD), flash memory device, volatile memory, or a hard disk drive (HDD), such as an external HDD or the HDD of a computing device, though embodiments are not limited thereto. A computing device can be, for example, a laptop computer, desktop computer, server, cell phone, or tablet, though embodiments are not limited thereto.

The subject invention includes, but is not limited to, the following exemplified embodiments.

Embodiment 1. A system for performing X-ray computed tomography (CT) imaging, the system comprising:
an X-ray source;
a detector for detecting X-ray radiation from the source;
a filter grating disposed between the source and the detector (to modify the original X-ray energy spectrum of the X-ray radiation of the X-ray source into two or more spectra), wherein the filter grating is positioned closer to the source than the detector is; and an absorption grating aligned with the filter grating (either before the filter grating or after the filter grating, along a path of X-ray radiation from the source to the detector) (to selectively block at least a portion of the X-ray radiation from reaching the filter grating so that a preferred X-ray spectrum can pass through the filter grating and can go through a patient or subject to be imaged at a given time instant), wherein at least one of the absorption grating and the filter grating is configured to move relative to the other during operation of the source.

Embodiment 2. The system according to embodiment 1, wherein the source is a kVp-switching X-ray source.

Embodiment 3. The system according to embodiment 2, wherein the absorption grating and the filter grating oscillate relative one another, and the oscillation is synchronized with a switching frequency of the source, such that each time the source switches its voltage level, at least one of the absorption grating and the filter grating moves relative to the other.

Embodiment 4. The system according to any of embodiments 2-3, wherein an oscillation period of the relative movement between the gratings is equal to half a time interval between two adjacent X-ray projections of the source.

Embodiment 5. The system according to embodiment 1, wherein the source is a single-kVp X-ray source (non-kVp-switching X-ray source).

Embodiment 6. The system according to embodiment 5, wherein the relative movement of the gratings is an oscillation movement (relative to each other) that is optimized for the single-kVp X-ray source.

Embodiment 7. The system according to any of embodiments 1-6, wherein the filter grating comprises at least two different types of filter material.

Embodiment 8. The system according to any of embodiments 1-7, wherein the filter grating comprises exactly two different types of filter material.

Embodiment 9. The system according to any of embodiments 1-8, wherein the absorption grating comprises slit portions and solid portions disposed alternatingly.

Embodiment 10. The system according to embodiment 9, wherein a width of each slit portion of the absorption grating is the same as that of each other slit portion of the absorption grating.

Embodiment 11. The system according to any of embodiments 9-10, wherein a width of each solid portion of the absorption grating is the same as that of each other solid portion of the absorption grating.

Embodiment 12. The system according to any of embodiments 9-11, wherein a width of each slit portion of the absorption grating is the same as that of each solid portion of the absorption grating.

Embodiment 13. The system according to any of embodiments 9-11, wherein a width of at least one slit portion of the absorption grating is different from that of at least one solid portion of the absorption grating.

Embodiment 14. The system according to any of embodiments 9-11, wherein a width of at least one slit portion of the absorption grating is narrower than that of at least one solid portion of the absorption grating.

Embodiment 15. The system according to any of embodiments 9-11, wherein a width of at least one slit portion of the absorption grating is wider than that of at least one solid portion of the absorption grating.

Embodiment 16. The system according to any of embodiments 9-11, wherein a width of each slit portion of the absorption grating is narrower than that of at least one solid portion of the absorption grating.

Embodiment 17. The system according to any of embodiments 9-11, wherein a width of each slit portion of the absorption grating is wider than that of at least one solid portion of the absorption grating.

Embodiment 18. The system according to any of embodiments 9-11, wherein a width of each slit portion of the absorption grating is narrower than that of each solid portion of the absorption grating.

Embodiment 19. The system according to any of embodiments 9-11, wherein a width of each slit portion of the absorption grating is wider than that of each solid portion of the absorption grating.

Embodiment 20. The system according to any of embodiments 9-11, wherein a width of at least one slit portion of the absorption grating is narrower than that of each solid portion of the absorption grating.

Embodiment 21. The system according to any of embodiments 9-11, wherein a width of at least one slit portion of the absorption grating is wider than that of each solid portion of the absorption grating.

Embodiment 22. The system according to any of embodiments 1-21, wherein the relative motion between the absorption grating and the filter grating is in a direction parallel to a front face of the absorption grating facing the source.

Embodiment 23. The system according to any of embodiments 1-22, wherein the absorption grating comprises a metal.

Embodiment 24. The system according to any of embodiments 1-23, wherein the absorption grating comprises gold.

Embodiment 25. The system according to any of embodiments 1-24, wherein a thickness of the absorption grating is 1 mm. Embodiment 26. The system according to any of embodiments 1-24, wherein a thickness of the absorption grating is at least 1 mm.

Embodiment 27. The system according to any of embodiments 1-24, wherein a thickness of the absorption grating is no more than 1 mm.

Embodiment 28. The system according to any of embodiments 1-24, wherein a thickness of the absorption grating is 0.5 mm.

Embodiment 29. The system according to any of embodiments 1-24, wherein a thickness of the absorption grating is at least 0.5 mm.

Embodiment 30. The system according to any of embodiments 1-24, wherein a thickness of the absorption grating is no more than 0.5 mm.

Embodiment 31. The system according to any of embodiments 1-30, wherein the filter grating comprises a first filter material and a second filter material that is less dense than the first filter material.

Embodiment 32. The system according to embodiment 31, wherein the first filter material is a metal air and the second filter material is air.

Embodiment 33. The system according to any of embodiments 31-32, wherein the first filter material is tin.

Embodiment 34. The system according to any of embodiments 31-33, wherein the filter grating comprises a plurality of strips of the second filter material, with the first filter material disposed alternatingly with the plurality of strips of the second filter material.

Embodiment 35. The system according to any of embodiments 1-34, wherein a thickness of the filter grating is 1 mm.

Embodiment 36. The system according to any of embodiments 1-34, wherein a thickness of the filter grating is at least 1 mm.

Embodiment 37. The system according to any of embodiments 1-34, wherein a thickness of the filter grating is no more than 1 mm.

Embodiment 38. The system according to any of embodiments 1-34, wherein a thickness of the filter grating is 0.5 mm.

Embodiment 39. The system according to any of embodiments 1-34, wherein a thickness of the filter grating is at least 0.5 mm.

Embodiment 40. The system according to any of embodiments 1-34, wherein a thickness of the filter grating is no more than 0.5 mm.

Embodiment 41. The system according to any of embodiments 1-40, wherein the filter grating moves while the absorption grating stays stationary during operation of the source.

Embodiment 42. The system according to any of embodiments 1-40, wherein the absorption grating moves while the filter grating stays stationary during operation of the source.

Embodiment 43. The system according to any of embodiments 1-40, wherein both the absorption grating and the filter grating move during operation of the source.

Embodiment 44. The system according to any of embodiments 1-43, further comprising a motor configured to move at least one of the absorption grating and the filter grating relative to the other during operation of the source.

Embodiment 45. The system according to embodiment 44, wherein the motor is a piezo-electrical motor.

Embodiment 46. The system according to any of embodiments 1-45, wherein the absorption grating has a curved geometry.

Embodiment 47. The system according to any of embodiments 1-46, wherein the filter grating has a curved geometry.

Embodiment 48. The system according to any of embodiments 1-47, wherein the filter grating is disposed between the source and a patient to be imaged.

Embodiment 49. The system according to any of embodiments 1-48, wherein a distance between the filter grating and the source is less than 1 meter.

Embodiment 50. The system according to any of embodiments 1-48, wherein a distance between the filter grating and the source is less than 500 mm.

Embodiment 51. The system according to any of embodiments 1-48, wherein a distance between the filter grating and the source is less than 250 mm.

Embodiment 52. The system according to any of embodiments 1-51, wherein the source is an X-ray tube.

Embodiment 53. A method of performing X-ray CT imaging, the method comprising:
providing the system according to any of embodiments 1-52 and 94-96; positioning a patient or sample to be imaged between the filter grating and the detector;
operating the source to provide X-ray radiation; and moving at least one of the filter grating and the absorption grating relative to the other during operation of the source.

Embodiment 54. The method according to embodiment 53, wherein the filter grating moves while the absorption grating stays stationary during operation of the source.

Embodiment 55. The method according to embodiment 53, wherein the absorption grating moves while the filter grating stays stationary during operation of the source.

Embodiment 56. The method according to embodiment 53, wherein both the absorption grating and the filter grating move during operation of the source.

Embodiment 57. The method according to any of embodiments 53-56, wherein the source is a kVp-switching X-ray source, and wherein an oscillation period of the relative movement between the gratings is equal to half a time interval between two adjacent X-ray projections of the source.

Embodiment 58. The method according to any of embodiments 53-56, wherein the source is a single-kVp X-ray source, and wherein the relative movement of the gratings is an oscillation movement (relative to each other) that is optimized for the single-kVp X-ray source.

Embodiment 59. The method according to any of embodiments 53-58, wherein the patient is a mammal.

Embodiment 60. The method according to any of embodiments 53-59, wherein the patient is a human.

Embodiment 61. A system for performing X-ray computed tomography (CT) imaging, the system comprising:
a single-kVp X-ray source (non-kVp-switching X-ray source);
a detector for detecting X-ray radiation from the source; and
a filter grating disposed between the source and the detector (to modify the original X-ray energy spectrum of the X-ray radiation of the X-ray source into two or more spectra), wherein the filter grating is positioned closer to the source than the detector is,
wherein the system excludes an absorption grating, and
wherein the filter grating is configured to be stationary during operation of the source.

Embodiment 62. The system according to embodiment 61, wherein the filter grating comprises at least two different types of filter material.

Embodiment 63. The system according to any of embodiments 61-62, wherein the filter grating comprises exactly two different types of filter material.

Embodiment 64. The system according to any of embodiments 61-63, wherein the filter grating comprises at least two filter strips.

Embodiment 65. The system according to any of embodiments 61-63, wherein the filter grating comprises exactly two filter strips.

Embodiment 66. The system according to embodiment 65, wherein the two filter strips comprise a first filter strip of a first filter material and a second filter strip of a second filter material different from the first filter material.

Embodiment 67. The system according to embodiment 66, wherein the first filter material is a metal air and the second filter material is air.

Embodiment 68. The system according to any of embodiments 66-67, wherein the first filter material is tin.

Embodiment 69. The system according to any of embodiments 61-64, wherein the filter grating comprises a first filter material and a second filter material that is less dense than the first filter material.

Embodiment 70. The system according to embodiment 69, wherein first filter material is a metal and the second filter material is air.

Embodiment 71. The system according to any of embodiments 69-70, wherein the first filter material is tin.

Embodiment 72. The system according to any of embodiments 69-71, wherein the first and second filter materials are disposed alternatingly in the filter grating.

Embodiment 73. The system according to any of embodiments 61-72, wherein a thickness of the filter grating is 1 mm.

Embodiment 74. The system according to any of embodiments 61-72, wherein a thickness of the filter grating is at least 1 mm.

Embodiment 75. The system according to any of embodiments 61-72, wherein a thickness of the filter grating is no more than 1 mm.

Embodiment 76. The system according to any of embodiments 61-72, wherein a thickness of the filter grating is 0.5 mm.

Embodiment 77. The system according to any of embodiments 61-72, wherein a thickness of the filter grating is at least 0.5 mm.

Embodiment 78. The system according to any of embodiments 61-72, wherein a thickness of the filter grating is no more than 0.5 mm.

Embodiment 79. The system according to any of embodiments 61-78, wherein the filter grating has a curved geometry.

Embodiment 80. The system according to any of embodiments 61-79, wherein the filter grating is disposed between the source and a patient to be imaged.

Embodiment 81. The system according to any of embodiments 61-80, wherein a distance between the filter grating and the source is less than 1 meter.

Embodiment 82. The system according to any of embodiments 61-80, wherein a distance between the filter grating and the source is less than 500 mm.

Embodiment 83. The system according to any of embodiments 61-80, wherein a distance between the filter grating and the source is less than 250 mm.

Embodiment 84. The system according to any of embodiments 61-83, wherein the source is an X-ray tube.

Embodiment 85. A method of performing X-ray CT imaging, the method comprising:
providing the system according to any of embodiments 61-84 and 96;
positioning a patient or sample to be imaged between the filter grating and the detector; and
operating the source to provide X-ray radiation.

Embodiment 86. The method according to embodiment 85, wherein the patient is a mammal.

Embodiment 87. The method according to any of embodiments 85-86, wherein the patient is a human.

Embodiment 88. The system according to any of embodiments 1-52 and 61-84, further comprising:
a processor; and
a (non-transitory) machine-readable medium (e.g., a computer-readable medium) in operable communication with both the processor and the detector and having machine-executable (e.g., computer-executable) instructions (stored thereon) for image reconstruction based on data received from the detector.

Embodiment 89. The system according to embodiment 88, wherein the image reconstruction is based on a non-linear X-ray data generation model.

Embodiment 90. The system according to any of embodiments 88-89, wherein the image reconstruction comprises non-linear data modeling and compressed sensing.

Embodiment 91. The method according to any of embodiments 53-60 and 85-87, wherein the system further comprises:
a processor; and
a (non-transitory) machine-readable medium (e.g., a computer-readable medium) in operable communication with both the processor and the detector and having machine-executable (e.g., computer-executable) instructions (stored thereon) for image reconstruction based on data received from the detector, and
wherein the method further comprises performing the image reconstruction.

Embodiment 92. The method according to embodiment 91, wherein the image reconstruction is based on a non-linear X-ray data generation model.

Embodiment 93. The method according to any of embodiments 91-92, wherein the image reconstruction comprises non-linear data modeling and compressed sensing.

Embodiment 94. The system according to any of embodiments 1-52, and 88-90, wherein the absorption grating is disposed between the filter grating and the source.

Embodiment 95. The system according to any of embodiments 1-52, 61-84, and 88-90, wherein the filter grating is disposed between the absorption grating and the source.

Embodiment 96. The system according to any of embodiments 1-52, 61-84, 88-90, 94, and 95, wherein the filter grating is positioned closer to the source than it is to the detector.

According to another embodiment, a system for performing X-ray computed tomography (CT) imaging is provided, the system comprising: an X-ray source; a detector for detecting X-ray radiation from the source; a filter grating disposed between the source and the detector to modify an X-ray energy spectrum of the X-ray radiation into two or more spectra, the filter grating comprising a first curvature; and an absorption grating aligned with the filter grating to selectively block at least a portion of the X-ray radiation, the absorption grating having a second curvature that is concentric with the curvature of the filter grating in relation to the X-ray source; wherein at least one of the absorption grating and the filter grating is configured to move relative to the other during operation of the source.

In some embodiments, the filter grating and the absorption grating each are substantially cylindrical in shape and are positioned such that the X-ray source lies approximately on the axis of each cylinder. In some embodiments, the system further comprises that the filter grating and the absorption grating each are substantially at least a portion of a sphere in shape and are positioned such that the X-ray source lies approximately at the center of each sphere. In some embodiments, the filter grating is at least a portion of a hemisphere.

In some embodiments, the system further comprises that the filter grating comprises: a set of first filter regions; a set of second filter regions; and a set of absorbing regions comprising an X-ray blocking material; wherein the first and second filter regions produce different X-ray spectra from the X-ray radiation; and wherein the first and second filter regions are positioned in an alternating fashion in the filter grating and the absorbing regions are positioned between each neighboring first and second filter regions.

In some embodiments, the movement of the at least one of the absorption grating and the filter grating is along a curved path that is parallel to the curvature of the absorption grating and the filter grating. In some embodiments, the movement of the at least one of the absorption grating and the filter grating is a rotation about an axis running substantially from the X-ray source to an approximate center of the absorption grating or the filter grating. In some embodiments, the X-ray source is pulsed.

According to another embodiment of the present invention, a system for performing X-ray computed tomography (CT) imaging is provided, the system comprising: an X-ray source; a detector for detecting X-ray radiation from the source; a filter grating, comprising: a set of first filter regions, the first filter regions adapted to produce a first X-ray spectrum from the X-ray radiation; a set of second filter regions, the second filter regions adapted to produce a second X-ray spectrum from the X-ray radiation, the second X-ray spectrum being different from the first X-ray spectrum; and a set of absorbing regions comprising an X-ray blocking material; and an absorption grating aligned with the filter grating to selectively block at least a portion of the X-ray radiation; wherein the first and second filter regions are positioned in an alternating fashion in the filter grating and the absorbing regions are positioned between each neighboring first and second filter regions; and wherein at least one of the absorption grating and the filter grating is configured to move relative to the other during operation of the source.

In some embodiments, the filter grating and the absorption grating are substantially planar. In some embodiments, the filter grating comprises a first curvature and the absorption grating comprises a second curvature that is concentric to the first curvature in relation to the X-ray source. In some embodiments, the filter grating and the absorption grating are substantially at least a portion of a sphere. In some embodiments, the filter grating is moved relative to the absorption grating in substantially only one direction during operation of the source. In some embodiments, the filter grating is rotated about an axis running substantially from the X-ray source to an approximate center of the absorption grating or the filter grating. In some embodiments, the filter grating is moved by at least one reel.

According to another embodiment of the present invention, a system for performing X-ray computed tomography (CT) imaging, the system comprising: an X-ray source; a detector for detecting X-ray radiation from the source; a filter grating disposed between the source and the detector to modify an X-ray energy spectrum of the X-ray radiation into two or more spectra; and an absorption grating aligned with the filter grating to selectively block at least a portion of the X-ray radiation; wherein at least one of the absorption grating and the filter grating is configured to move in substantially only one direction relative to the other during operation of the source.

In some embodiments, the filter grating is rotated relative to the absorption grating about an axis running substantially from the X-ray source to an approximate center of the absorption grating or the filter grating. In some embodiments, the filter grating is moved relative to the absorption grating by at least one reel. In some embodiments, the system further comprises that the filter grating and the absorption grating each are each substantially at least a portion of a sphere in shape and are positioned such that the X-ray source lies approximately at the center of each sphere; and wherein the axis of rotation of the filter grating runs substantially from the X-ray source to an approximate center of the filter grating.

In some embodiments, the system further comprises: a set of first filter regions; a set of second filter regions; and a set of absorbing regions comprising an X-ray blocking material; wherein the first and second filter regions produce different X-ray spectra from the X-ray radiation; and wherein the first and second filter regions are positioned in an alternating fashion in the filter grating and the absorbing regions are positioned between each neighboring first and second filter regions. In some embodiments, the filter grating comprises a first curvature and the absorption grating comprises a second curvature that is concentric to the first curvature in relation to the X-ray source.

A greater understanding of the present invention and of its many advantages may be had from the following examples, given by way of illustration. The following examples are illustrative of some of the methods, applications, embodiments and variants of the present invention. They are, of course, not to be considered as limiting the invention. Numerous changes and modifications can be made with respect to the invention.

Simulation Parameters

Numerical simulations were carried out to evaluate GOLF systems and methods of embodiments of the subject invention, both for kVp-switching and non-kVp-switching dual-energy CT systems. Water and bone were selected as basis materials, and images were reconstructed via conventional filtered-back-projection without pre- and post-processing steps.

A CT imaging simulation platform was implemented to evaluate the performance of the proposed filtration methods. In the simulation, 140 kVp was set for single-kVp (non-kVp-switching) dual-energy CT, and 80 kVp and 140 kVp X-rays were used for kVp-switching dual-energy CT scanning. For both kVp settings, 100,000 photons were generated, and Poisson noise was added into the projections. In the CT geometry, the distance between the X-ray focal spot and the rotation center was set to 500 mm, and the distance between the X-ray focal spot and the flat-panel detector was set to 900 mm. There were 888 channels in the detector array with cell size of 1 mm. The field-of view was set to 320 mm with 512×512 pixels and 0.625 mm pixel size. The chest phantom depicted in FIG. 8 was used, in which titanium-material rods were inserted, as indicated by the large (white) dots near the bottom middle of the phantom.

Figure 8:
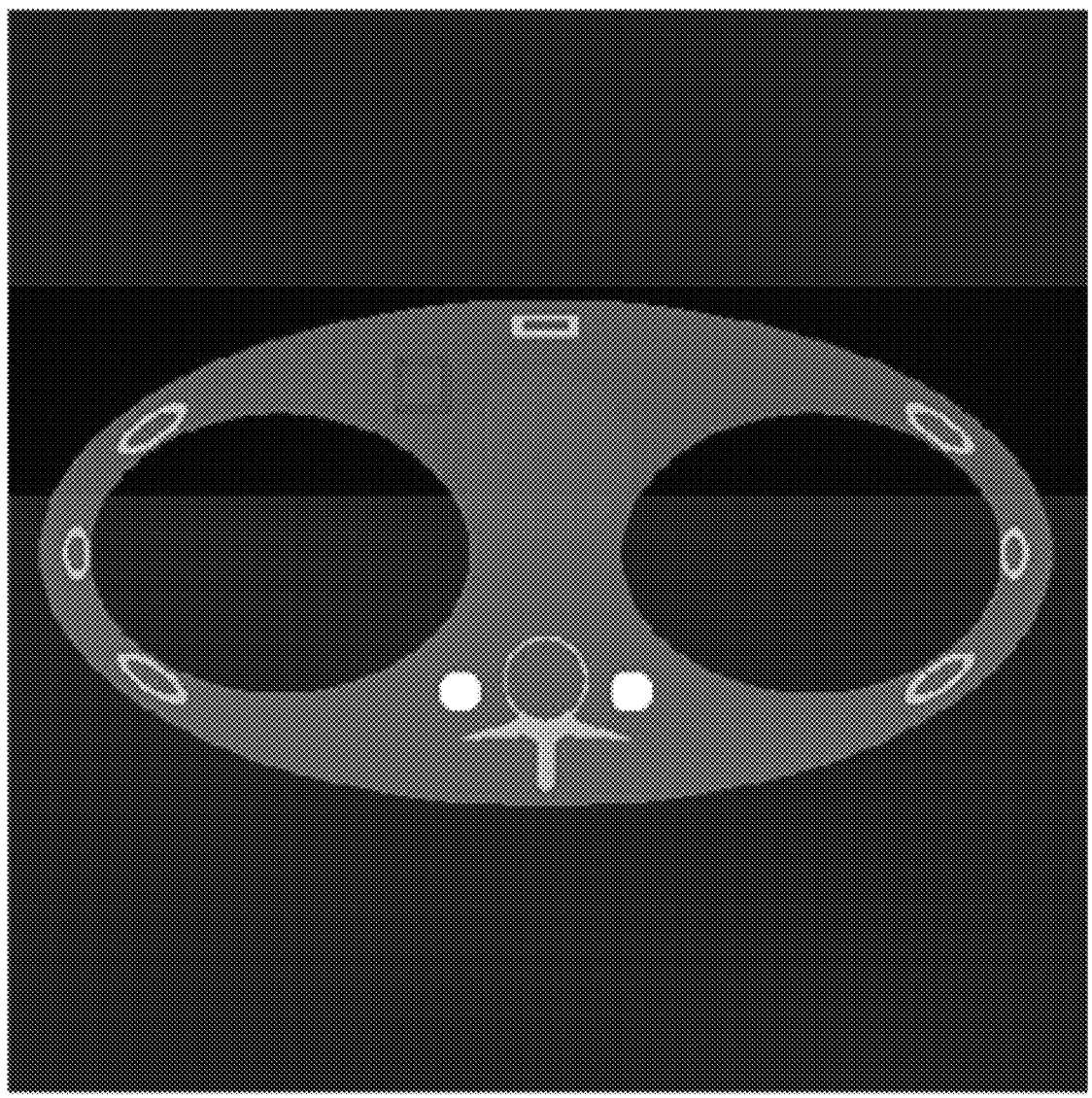
FIG. 8 shows a chest phantom.

The signal-to-noise ratio (SNR) is defined as $$\frac{(\bar{A}_{blue} - \bar{A}_{red})}{\sqrt{\sigma^2_{Ablue} + \sigma^2_{Ared}}}, \quad (16)$$

where $\bar{A}$ is the average over a region of interest (ROI), and σ is the standard variation in the ROI, to quantify a monochromatic image. In FIG. 8, two squares are included in the upper-middle area of the phantom; these boxes are ROIs of 30×30 pixels. In some analyses of embodiments of the present invention, the SNR is equivalent to and/or interchangeable with the contrast-to-noise ratio (CNR).

These conditions and parameters were for all numerical simulation examples.

EXAMPLE 1

A GOLF$_k$ system/method was simulated for kVp-switching based dual-energy CT. In a CT scan, 1,440 projections were collected where half of the data were at 80 kVp and the other half were at 140 kVp. The filter grating used 0.0 mm (air) and 1.0 mm thick tin with a duty cycle of 50%. The thickness of the X-ray absorption grating was 1 mm gold material allowing 99.995% absorption of X-rays at 100 keV. The duty cycle was changed from 10% to 100%, with a duty cycle of 100% being equivalent to conventional kVp-switching imaging. The monochromatic images were reconstructed according to Equation 14.

Figure 9:
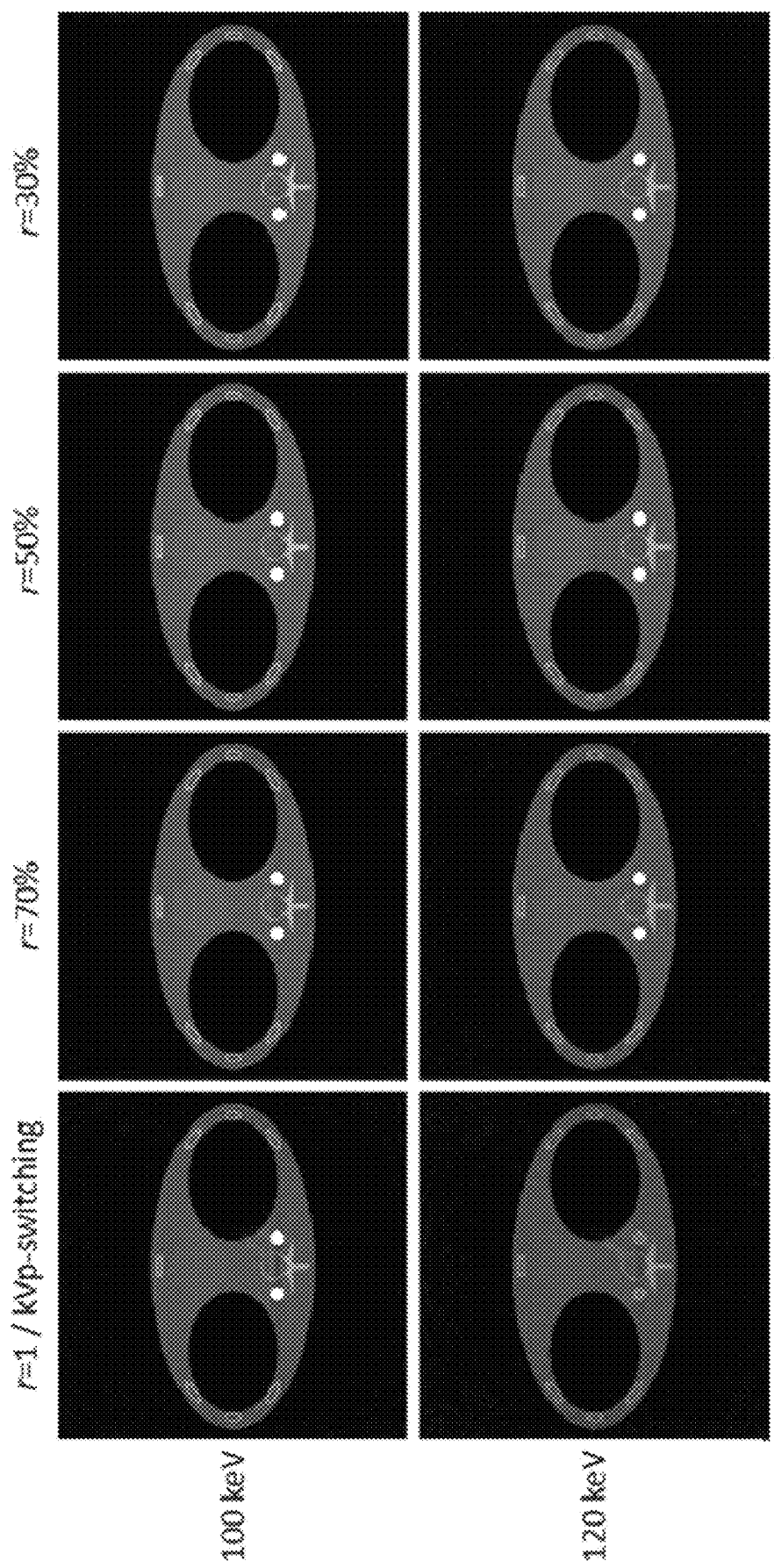
FIG. 9 shows eight reconstructed monochromatic images from a numerical simulation of CT scans.
Figure 10:
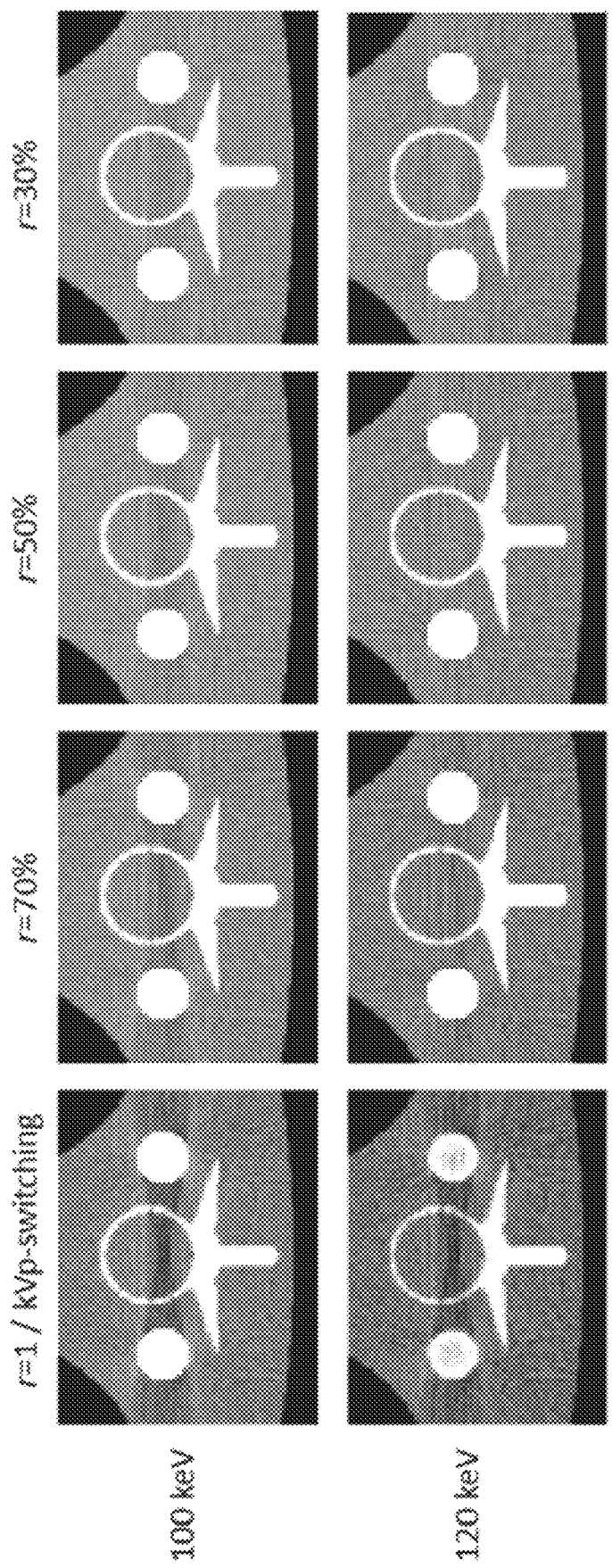
FIG. 10 shows eight enlarged images of the local metal areas (the areas around the rods represented by the dots near the lower-middle section of the phantom) of the corresponding images from FIG. 9.

FIG. 9 shows the reconstructed monochromatic images for this example. In FIG. 9, the first row presents images at 100 keV at different absorption grating duty cycles, as listed above each column. The first column is for a duty cycle of 100% (equivalent to conventional kVp-switching imaging). The second row shows results at 120 keV at different absorption grating duty cycles. FIG. 10 shows the local metal areas (the areas around the rods represented by the dots near the lower-middle section of the phantom) of the images from FIG. 9. The rows and columns in FIG. 10 are for the same energy/duty cycle combinations as in FIG. 9. FIG. 13A shows the SNR values for the images of FIG. 9. In FIG. 13A, the cross data points are for an energy of 100 keV, the circle data points are for an energy of 120 keV, the y-axis shows the SNR, and the x-axis shows the different duty cycles investigated.

Referring to FIGS. 9 and 10, the first column for each shows the performance that is equivalent to conventional kVp-switching dual-energy CT. There are clear beam hardening artifacts indicated by the (red) arrow present in each image in the first column of FIG. 9, and this can be seen more clearly in the enlarged views in the first column of FIG. 10. At the same location in the images in the second, third, and fourth columns of these Figures, significantly less artifacts are present, and the best performance was for r=30%. Referring to FIG. 13A, with a smaller absorption grating opening, the low- and high-energy X-ray spectra have better separation, leading to better image quality, in particular in terms of beam-hardening reduction.

EXAMPLE 2

A GOLF$_c$ system/method was simulated for single-kVp-based (non-kVp-switching) dual-energy CT. In a CT scan, 1,440 projections were collected at 140 kVp. The filter grating used 0.1-mm tin and 1.0-mm tin in the two strip filter, and 0.0-mm tin (air) and 1.0-mm tin with 50% duty cycle in the multi-strip grating. The monochromatic images were reconstructed according to Equation 14.

Figure 11:
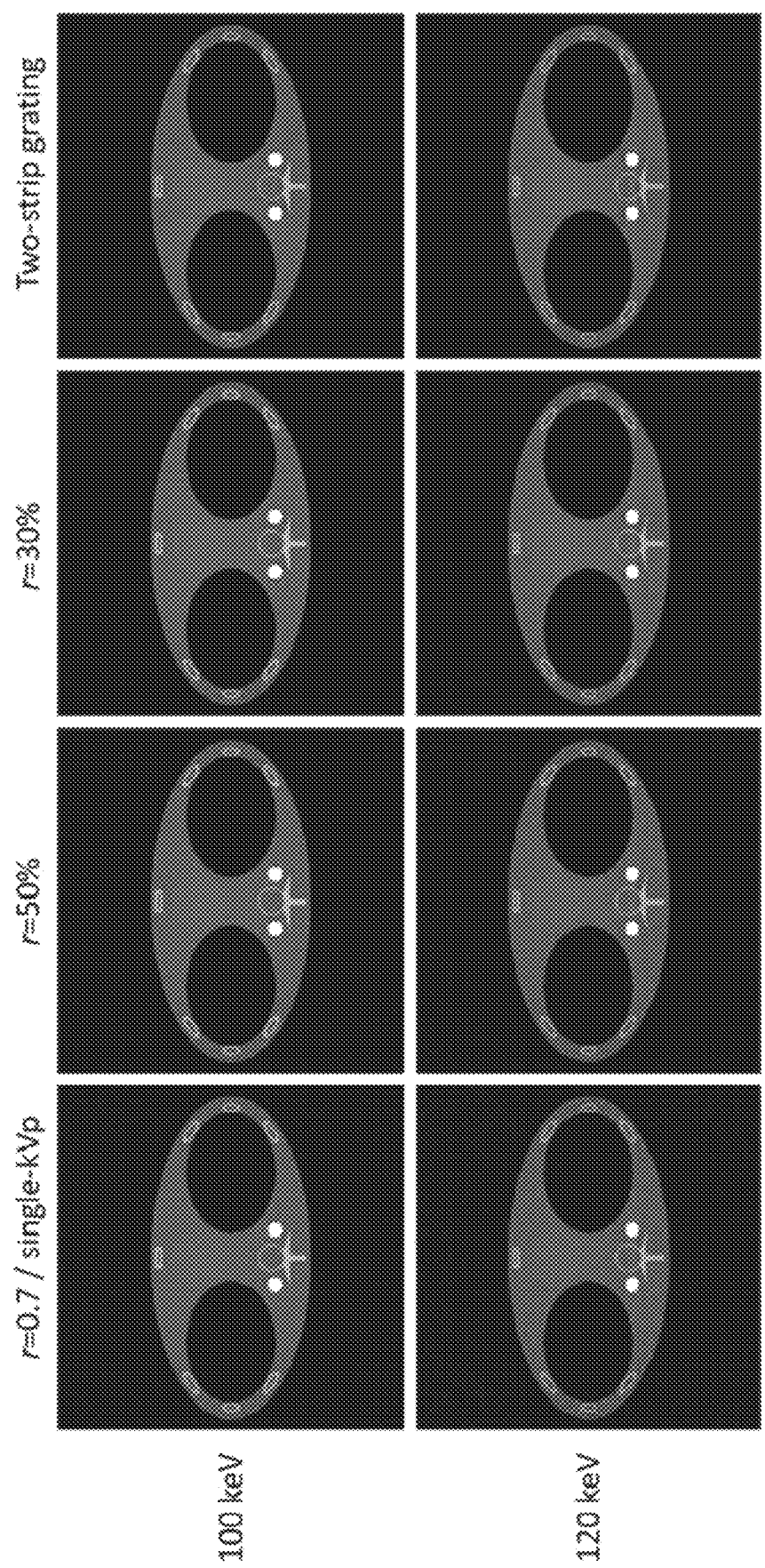
FIG. 11 shows eight reconstructed monochromatic images from a numerical simulation of CT scans.
Figure 12:
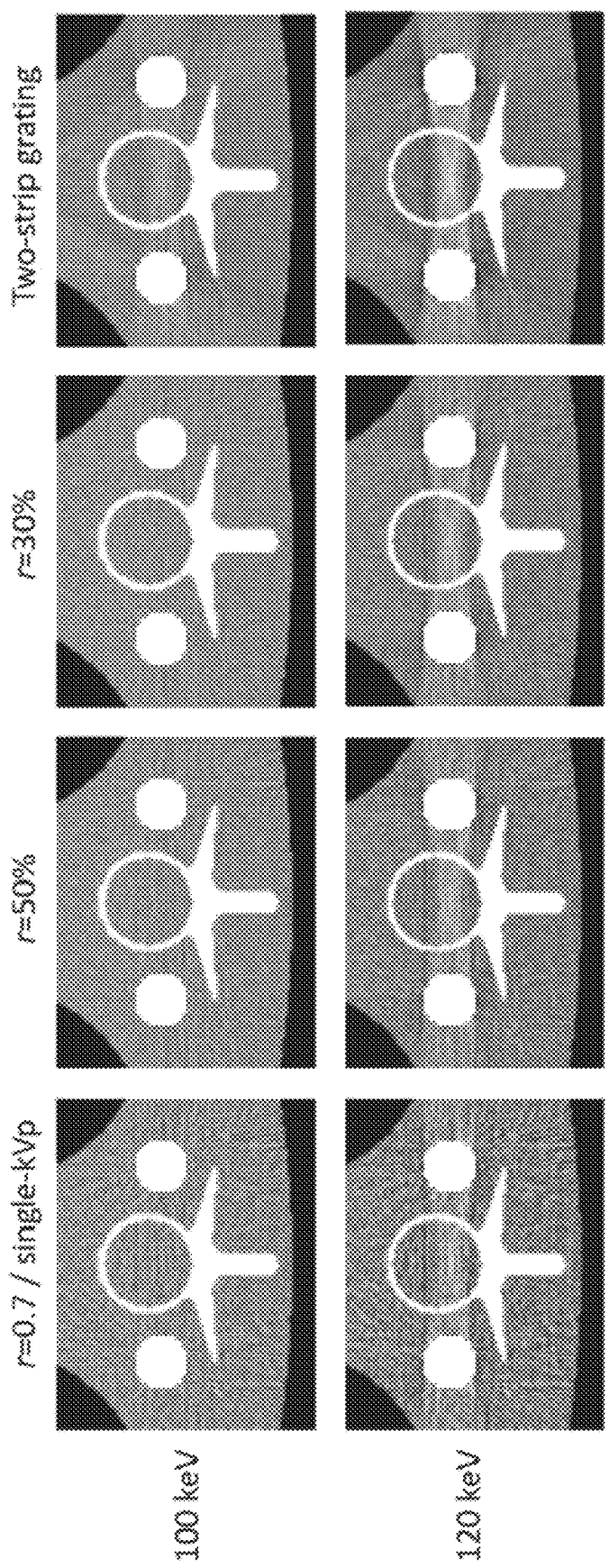
FIG. 12 shows eight enlarged images of the local metal areas (the areas around the rods represented by the dots near the lower-middle section of the phantom) of the corresponding images from FIG. 11.

FIG. 11 shows the reconstructed monochromatic images for this example. In FIG. 11, the first row presents images at 100 keV at different absorption grating duty cycles for multi-strip gratings (in the first three columns) and for a two-strip grating (in the fourth column), as listed above each column. The second row shows results at 120 keV. FIG. 12 shows the local metal areas (the areas around the rods represented by the dots near the lower-middle section of the phantom) of the images from FIG. 11. The rows and columns in FIG. 12 are for the same energy/duty cycle combinations as in FIG. 11. FIG. 13B shows the SNR values for the images of FIG. 11. In FIG. 13B, the cross data points are for an energy of 100 keV, the circle data points are for an energy of 120 keV, the y-axis shows the SNR, and the x-axis shows the different duty cycles investigated for the multi-strip gratings (first three marks on x-axis) and the two-strip grating (right-most mark on x-axis).

Referring to FIGS. 11 and 12, there are some artifacts in the central area of the images with the two-strip grating method (far right column in each of FIGS. 11 and 12). They were caused by the data interpolation in the sinogram, which can be avoided by advanced algorithms, such as iterative reconstruction schemes (see also reference [24] in the References section, which is hereby incorporated herein by reference in its entirety). Overall, the two-strip grating approach has a similar performance to that of the 50% duty cycle multi-strip grating approach.

Comparing the GOLF$_c$ method/system of this example to the GOLF$_k$ method/system of Example 1, the kVp-switching method results in better performance across the board in terms of beam-hardening reduction and SNR, which is consistent with its improved spectrum separation demonstrated by comparing FIGS. 5A-5C with FIGS. 7A-7B. Also, with the GOLF$_k$ system/method, a smaller absorption grating opening (smaller duty cycle) leads to SNR performance for a given radiation dose to the patient, but at the same time reduces the X-ray source efficacy.

EXAMPLE 3

A GOLF$_k$ system/method was simulated for kVp-switching based dual-energy CT, including collecting 360, 720, 1080 projections of each energy X-rays in turn. The thickness of the X-ray absorption grating was 1 mm gold materials having 99.995% absorption of X-rays at 100 keV. In the filter grating, the two filtration materials for 80 kVp and 140 kVp X-rays were air and tin, respectively. The thickness of tin material was set to 0 mm, 0.25 mm, and 0.5 mm in different experiments. The vibration frequency of the filter grating was set to match the switching frequency of X-ray energies in the X-ray source.

Figure 14:
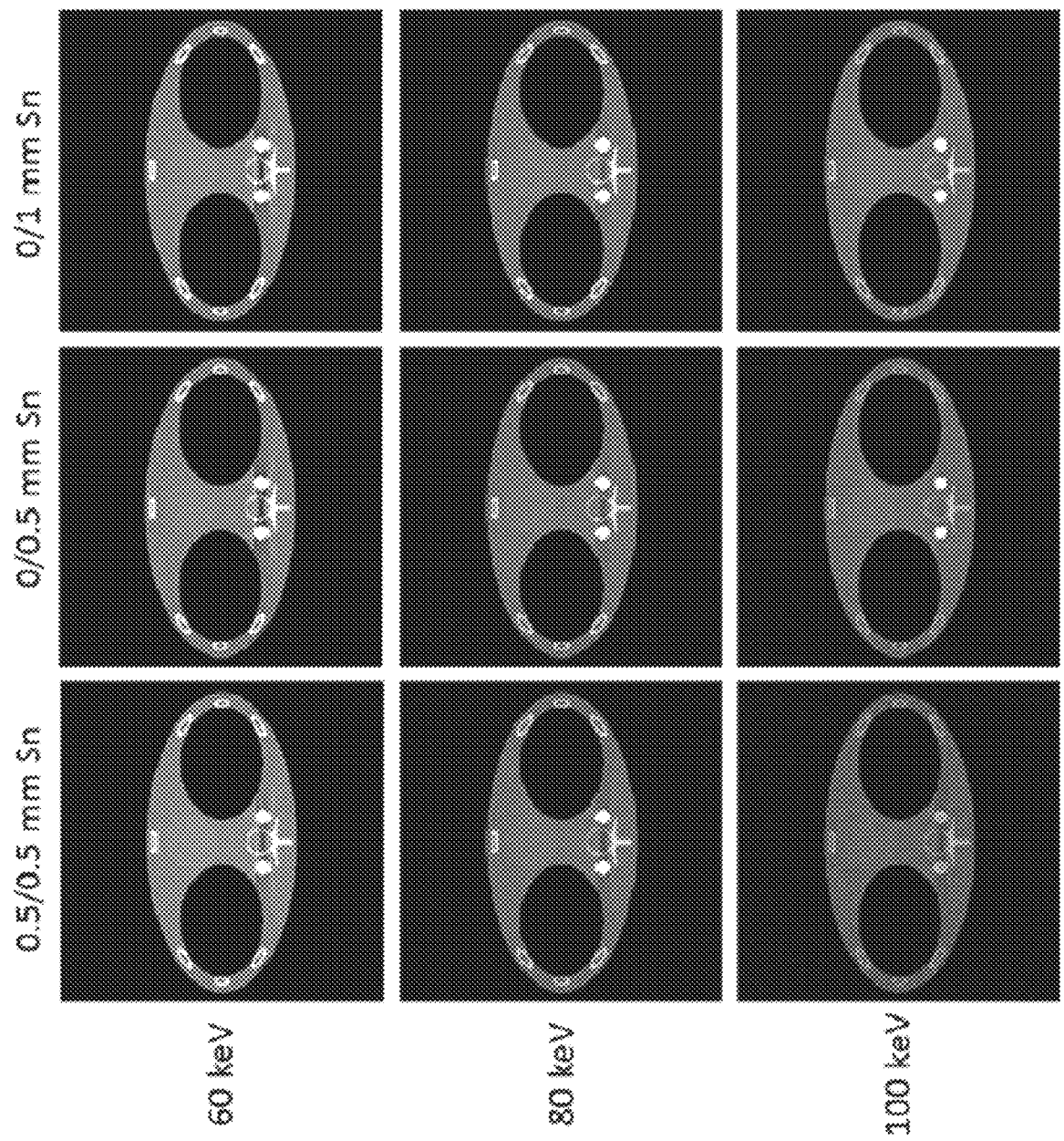
FIG. 14 shows nine reconstructed monochromatic images from a numerical simulation of CT scans.
Figure 15:
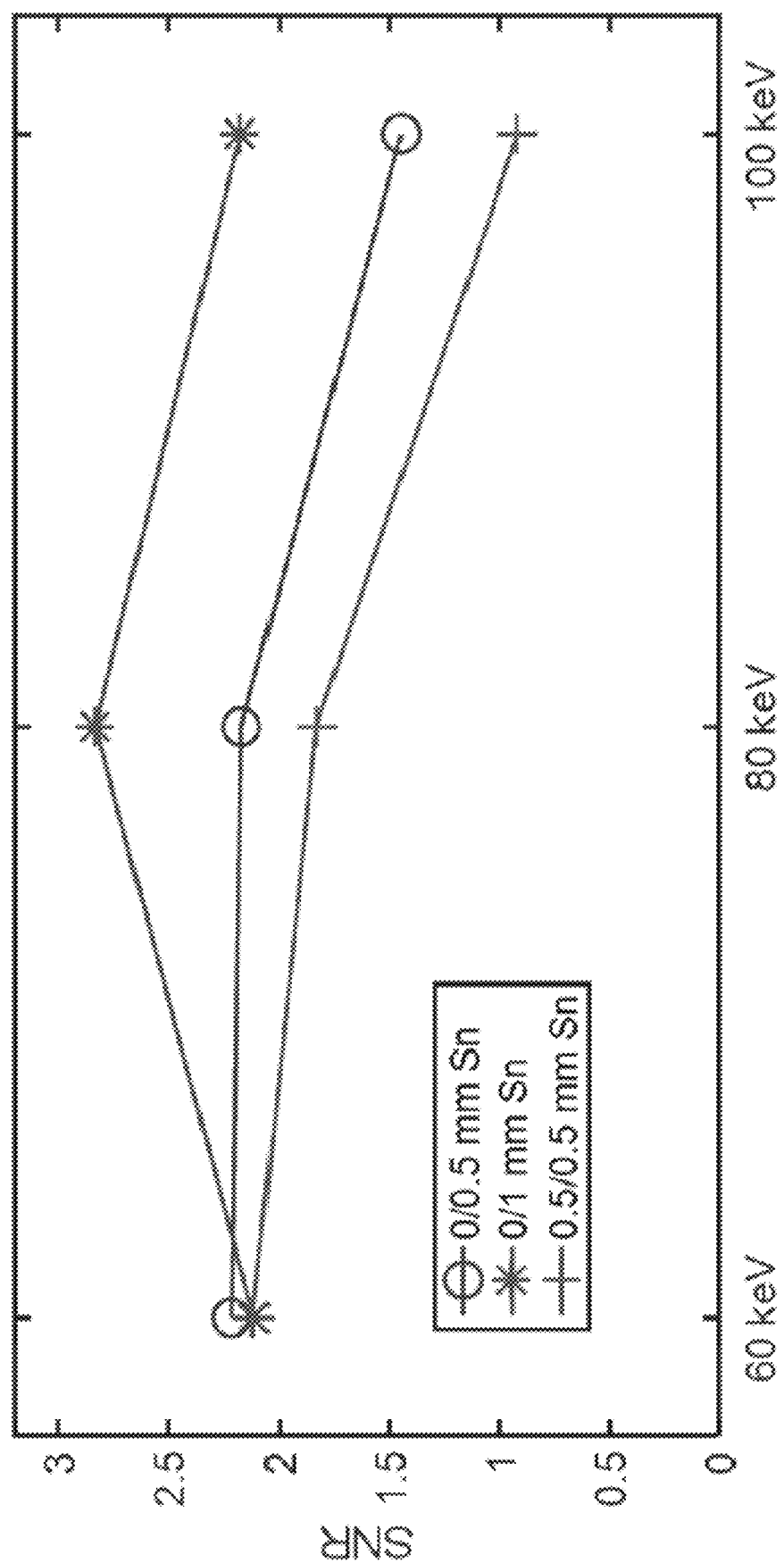
FIG. 15 shows a plot of SNR versus energy for the images of FIG. 14.

FIG. 14 shows the reconstructed monochromatic images. The first column presents images at energies of 60 keV, 80 keV and 100 keV (in the first, second, and third rows, respectively) with 0.5 mm tin and 0.5 mm tin (i.e., a conventional kVp-switching method). The right-most columns show the results for air and 0.5 mm tin (middle column) and air and 1 mm tin (right-most column). FIG. 15 shows a plot of SNR for these images. The cross data points are for the conventional kVp-switching method, the circle data points are for the air/1 mm tin GOLF$_k$ system/method, and the star data points are for the air/0.5 mm tin GOLF$_k$ system/method. The upper-most (green) line shows connects the star data points, the middle-most (red) line connects the circle data points, and the lower-most (blue) line connects the cross data points.

Referring to FIGS. 14 and 15, it can be plainly seen that the GOLF$_k$ system/method leads to much clearer monochromatic images, both visually and quantitatively. The air/0.5 mm tin GOLF$_k$ system/method provides better results than the air/1 mm tin GOLF$_k$ system/method.

EXAMPLE 4

A GOLF$_k$ system/method was simulated for kVp-switching based dual-energy CT, including collecting 360, 720, 1080 projections of each energy X-rays in turn. The fixed filtration materials were air for 80 kVp X-rays and 0.5 mm tin for 140 kVp X-rays. The distance between focal spots was determined by the geometry of the CT scanner and the angular difference between neighboring projections. In the 360 projection setting, a uniform angular sampling around the circular trajectory was assumed, and the distance between neighboring 80 kVp and 140 kVp X-rays was 4.36 mm. In the X-ray source, the X-ray focal spots and corresponding filters were set to a distance of 4.36 mm accordingly to have the collected neighboring 80 kVp and 140 kVp projection pairs with the same projection angles. Results were obtained using the X-flying focal spot method.

Figure 16:
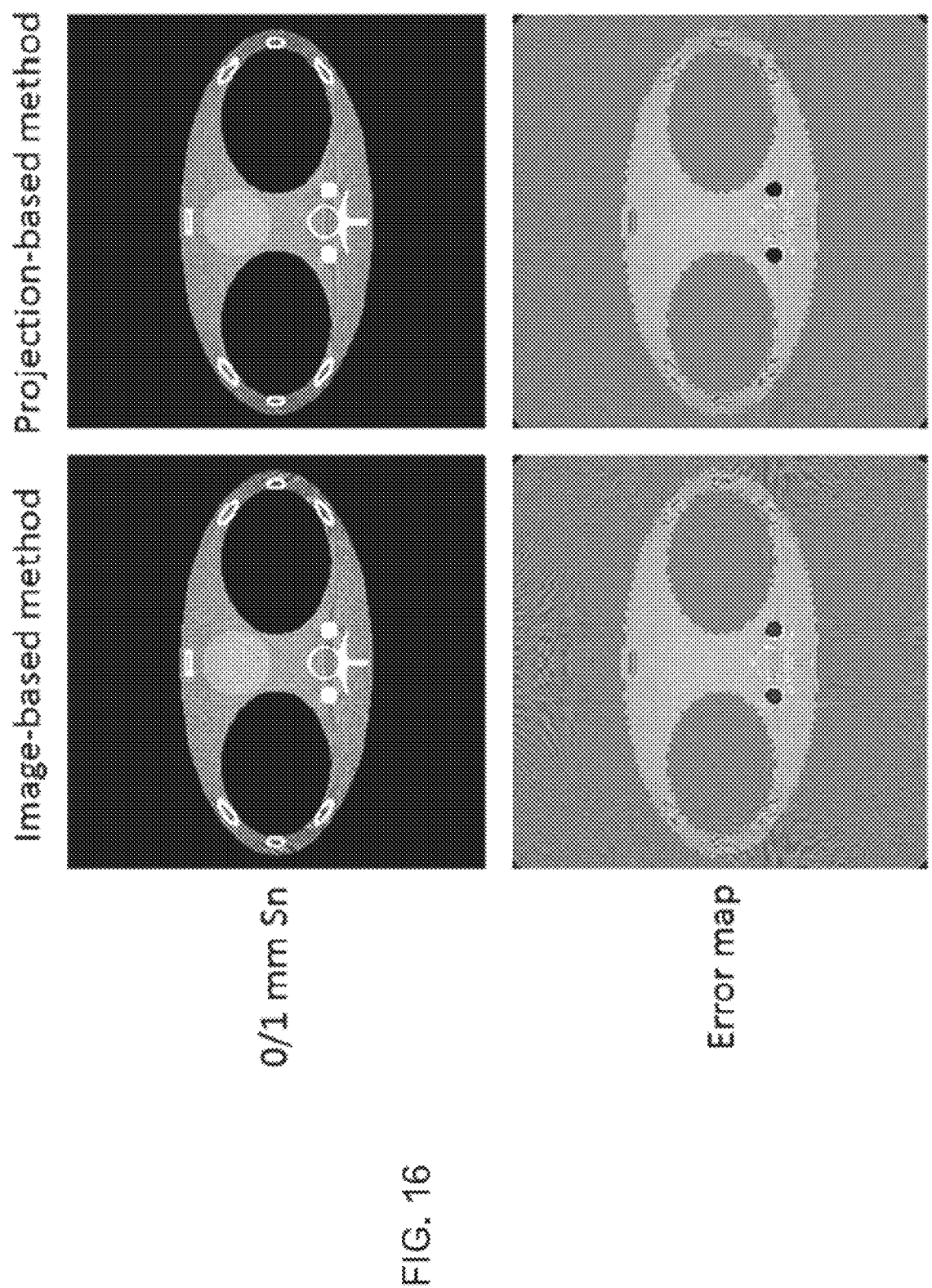
FIG. 16 shows reconstructed monochromatic images from a numerical simulation of CT scans.
Figure 17:
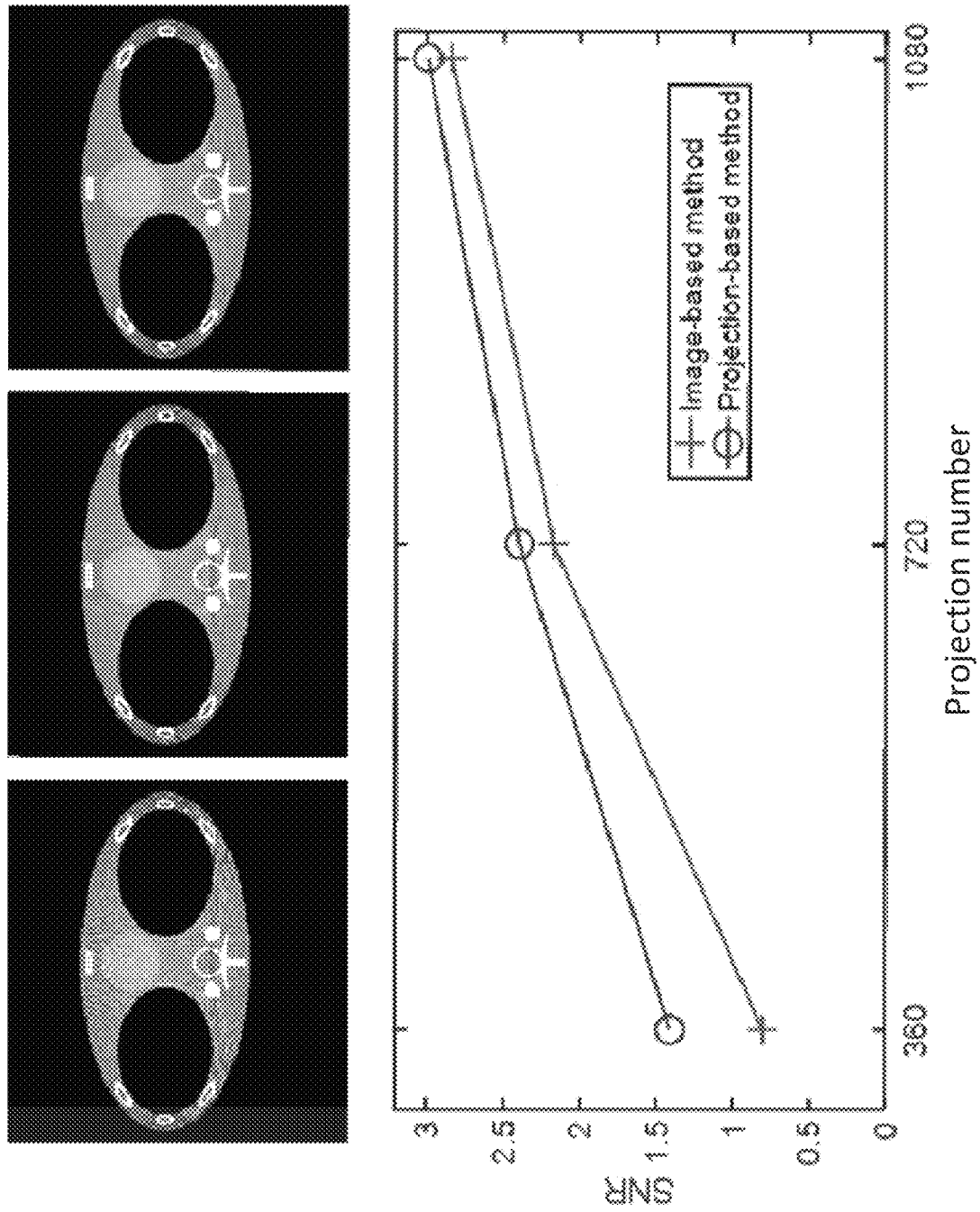
FIG. 17 shows reconstructed monochromatic images from a numerical simulation of CT scans (top portion) and a plot of SNR versus number of projections.

FIG. 16 shows a comparison of the 100 keV, 720-projection 0/0.5 mm Sn image from FIG. 14 for Example 3 (the bottom-middle image in FIG. 14) with the image obtained in this example at 100 keV, 720-projection. The first row shows the images, and the second row shows the error map; the first column is the image from Example 3, and the second column is the image from this example. FIG. 17 shows the images from this example across the top; images left to right are for 360, 720, and 1080 projections (100 keV, 0/0.5 mm Sn), respectively, and the plot at the lower portion of FIG. 17 shows a plot of the SNR vs. projection number. The circle data points are for this example (the three images at the top portion of FIG. 17) and are connected by the upper (red) line, and the cross data points are for Example 3 and are connected by the lower (blue) line. The cross data points are for 100 keV, 0/0.5 Sn at the three different numbers of projections. Referring to FIGS. 16 and 17, it can be seen that a higher number of projections gives a better monochromatic image, and the X-flying focal spot method improves the results slightly.

EXAMPLE 5

Figure 18:
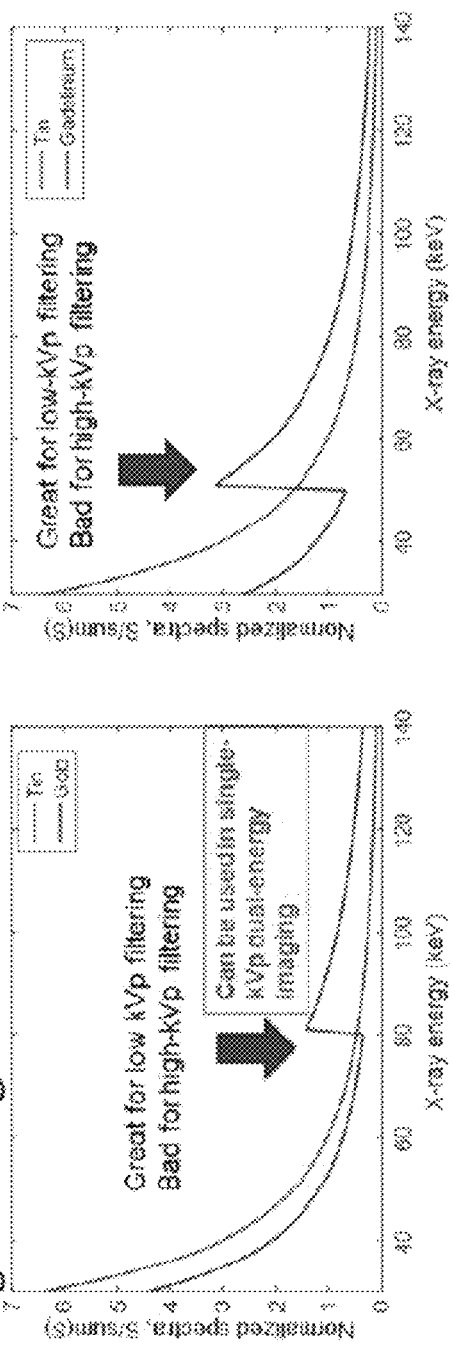
FIG. 18 shows four plots for K-edge filtering, with two plots of normalized spectra versus X-ray energy (top portion) and two plots of spectra versus X-ray energy (lower portion).
Figure 18:
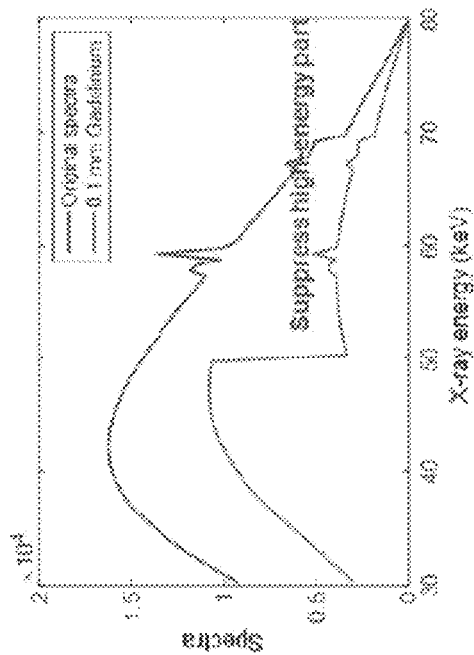
Figure 18:
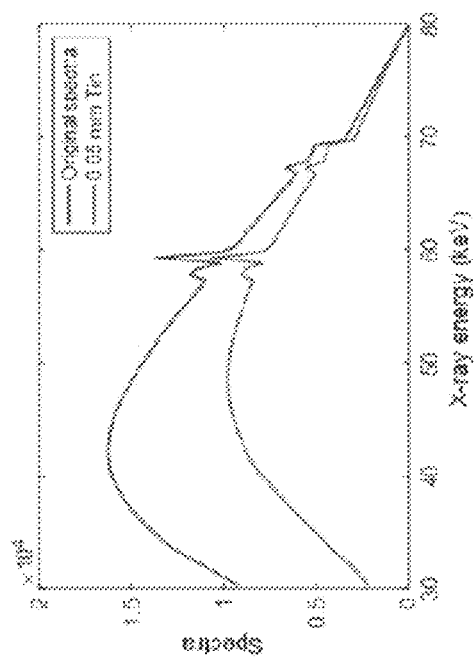

A GOLF system/method was simulated for K-edge filtering. The top portion of FIG. 18 shows plots of normalized spectra versus X-ray energy for tin and gold (top left, with the (blue) line that is higher at the left of the plot being for tin and the (red) line that is higher at the right of the plot being for gold) and for tin and gadolinium (top right, with the (blue) line that is higher at the left of the plot being for tin and the (red) line that is higher at the right of the plot being for gadolinium). The bottom portion of FIG. 18 shows plots of spectra versus X-ray energy for without GOLF ("original") and then using a 0.05 mm tin absorption grating (bottom left, with the (blue) line that is higher at the left of the plot being for the original and the (red) line that is lower at the left of the plot being for 0.5 mm tin) and for original and 0.1 mm gadolinium (bottom right, with the (blue) line that is higher at the left of the plot being for the original and the (red) line that is lower at the left of the plot being for 0.1 mm gadolinium). It should be understood that the examples and embodiments described herein are for illustrative purposes only and that various modifications or changes in light thereof will be suggested to persons skilled in the art and are to be included within the spirit and purview of this application.

EXAMPLE 6

Eq. (4) above shows that there is little diffraction of x-rays using gratings according to embodiments of the present invention. This means that all x-ray propagation can be modeled by geometric optics. The grating bars will block x-rays, and for the source focal spot size larger than the grating bars each point on the detector will simply receive an equal amount of flux from those parts of the focal spot that are not blocked. There is no blurring of the source spot.

Figure 28B:
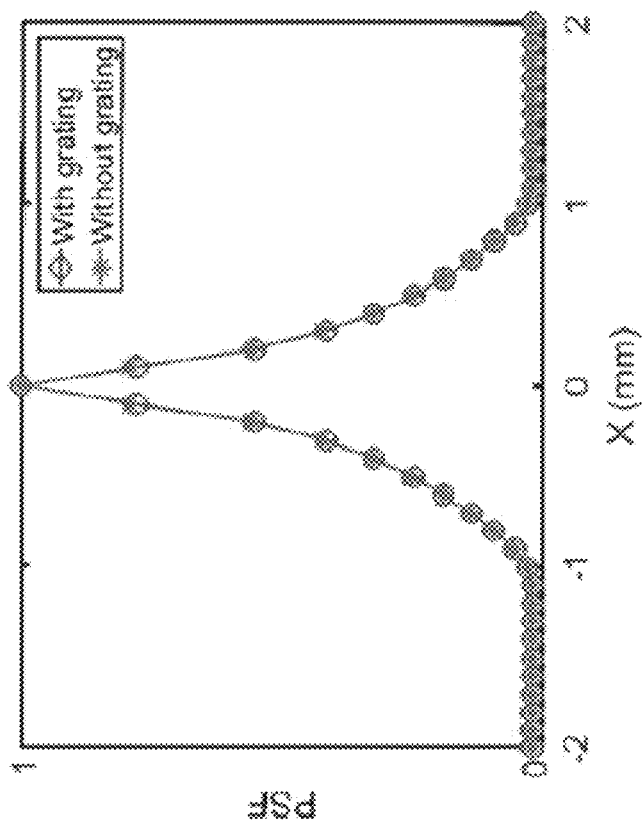
FIG. 28B shows simulated experimental data for the projection seen at the detector with and without the absorption grating for the point spread function (PSF) measured by placing an ideal high-absorption 0.5 mm rod at the center of the imaging field of view.
Figure 28A:
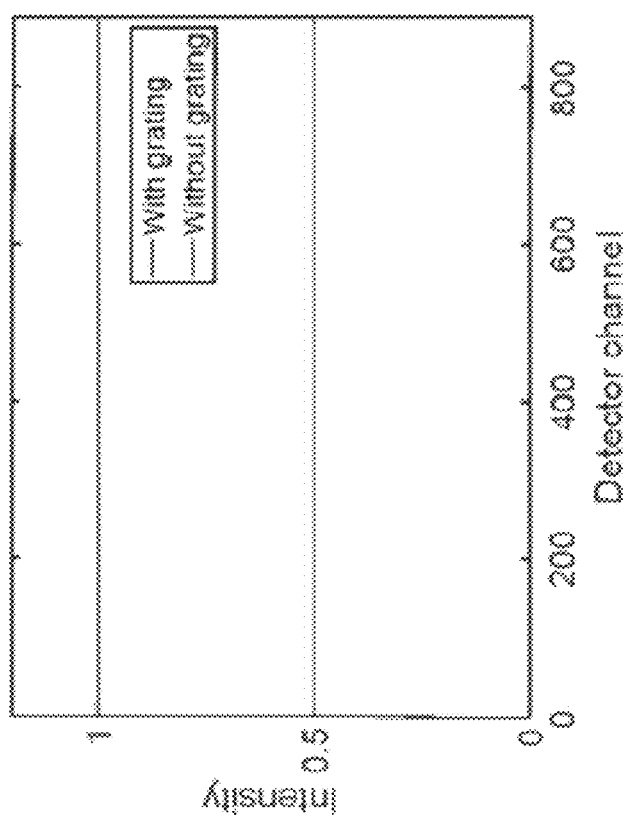
FIG. 28A shows simulated experimental data for the detected (distance normalized) x-ray intensity profile across a detector array with and without absorption grating as discussed herein.

A simulation experiment was performed to verify no increment in the apparent spot size or loss of the image resolution. The simulation setup is the same as shown in FIG. 20. The focal spot size was set to 1 mm, and SGD and SDD were set to 100 mm and 1000 mm respectively. According to Eq. (3) with n=4, an absorption grating period of 0.225 mm will give a uniform illumination on the detector array (after normalization for intensity fall-off due to source-to-pixel distance). An ideal zero-thickness absorption grating with a period of 0.225 mm and 50% duty cycle was used. X-rays were collected using an ideal 888-pixel detector array of 1 mm pixels. FIG. 28A shows the detected (distance normalized) x-ray intensity profile across the detector array with and without the absorption grating. The intensity profiles are uniform in both the cases, except that the profile with the grating is just half of that without the grating. That is, the x-ray intensity with grating is 0.5 compared to the intensity without grating of 1.

The system point spread function (PSF) was measured by placing an ideal high-absorption 0.5 mm rod at the center of the imaging field of view. FIG. 28B shows the projection seen at the detector with and without the absorption grating. The PSF convolved profiles account for the focal spot distribution, the absorption grating, and the 0.5 mm-diameter rod.

The PSF with the grating is virtually identical to the PSF without the grating, without any observable effect of the GOLF gratings on the image resolution.

EXAMPLE 7

The simulated CNR performance of two different embodiments of the present invention (referred to as GOLF1 and GOLF2), normal kVp-switching, and dual-source CT were all compared in FIG. 30 using the thorax phantom and the system parameters as described above. CNR is calculated using the following equation:

$$\frac{(\overline{A}_{blue} - \overline{A}_{red})}{\sqrt{\sigma_{Ablue}^2 + \sigma_{Ared}^2}} \qquad (17)$$

where $\overline{A}$ is the average over a region of interest (ROI), and σ is the standard deviation within the ROI.

Figure 30B:
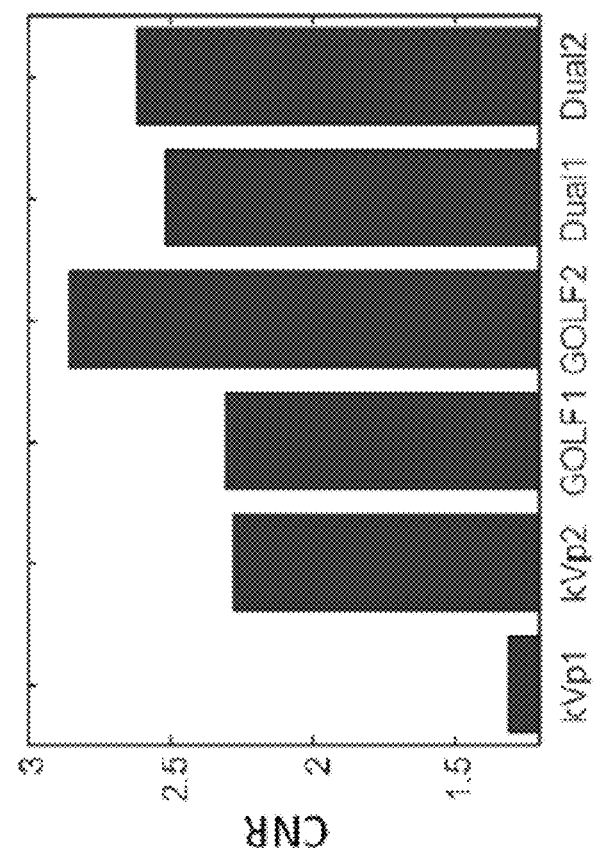
FIG. 30B shows the contrast-to-noise ratios for the six systems in the simulation referred to in FIG. 30A.
Figure 30A:
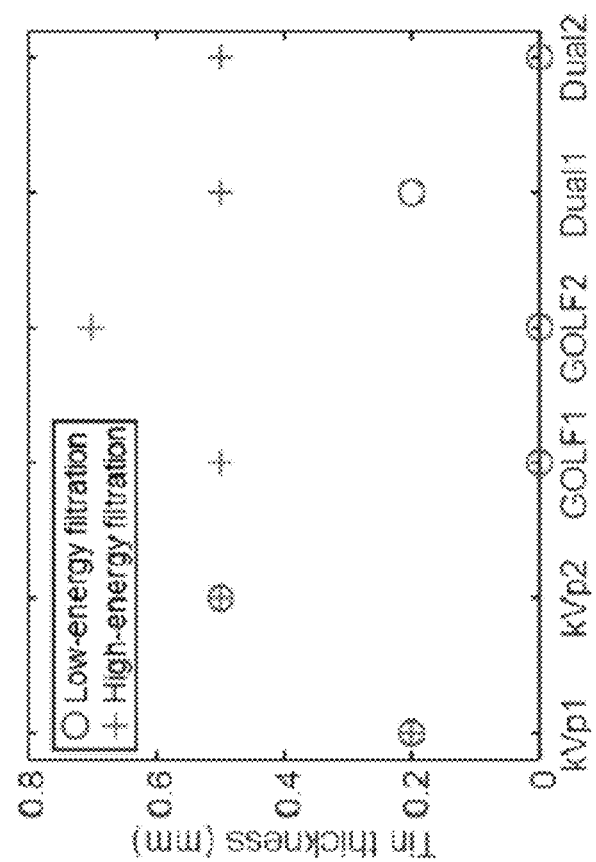
FIG. 30A shows filter thicknesses for six systems subjected to experimental simulation.

Six different simulations were performed, two for each system type. For both GOLF simulations, the duty cycle is r=50%. FIG. 30A shows the filter thicknesses and system type for each simulation. FIG. 30B shows the resulting CNR values. For example, GOLF2 used Air as the low-pass filter for the 80 kVp views, and 0.7 mm Tin as the high-pass filter for the 140 kVp views. The resulting water-blood CNR was 2.8, the best of the simulation results. GOLF2 has produced significantly higher CNR than either kVp1 or kVp2, and kVp2 had a dramatic low-kVp flux inefficiency due to attenuation by the 0.5 mm Tin filter.

Figure 31:
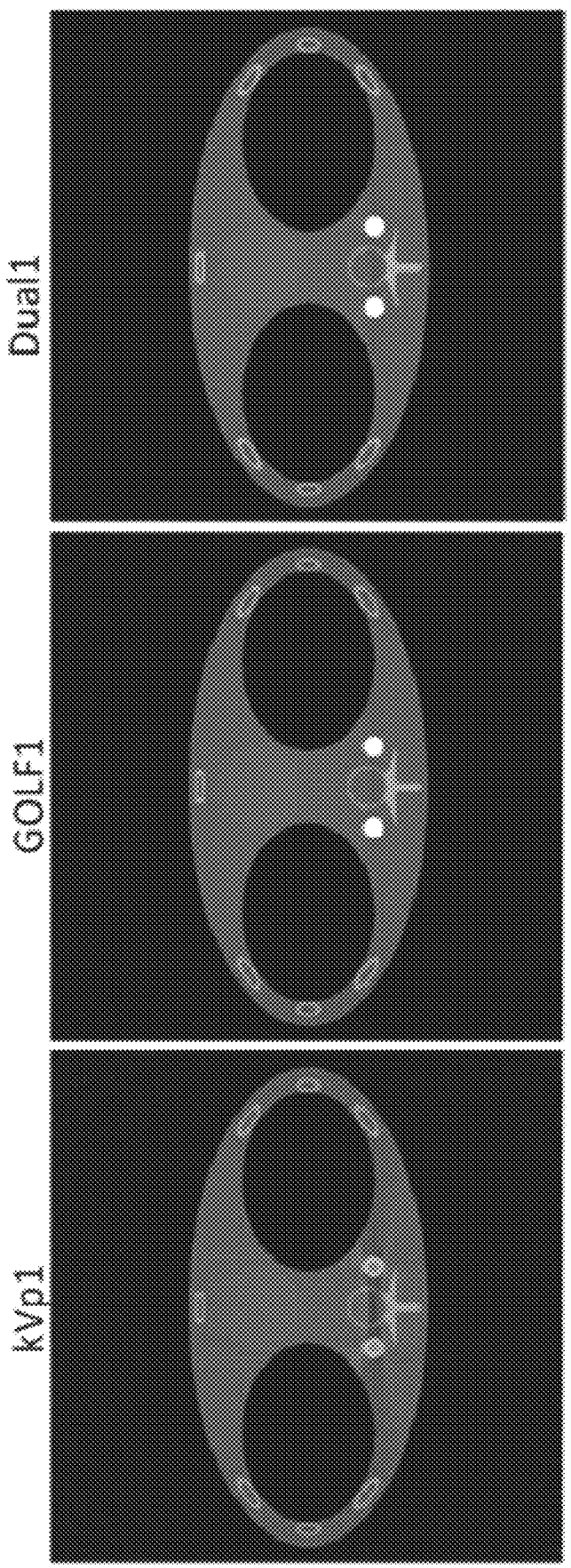
FIG. 31 shows monochromatic reconstructions for three of the simulations referred to in FIG. 30A.
Figure 32:
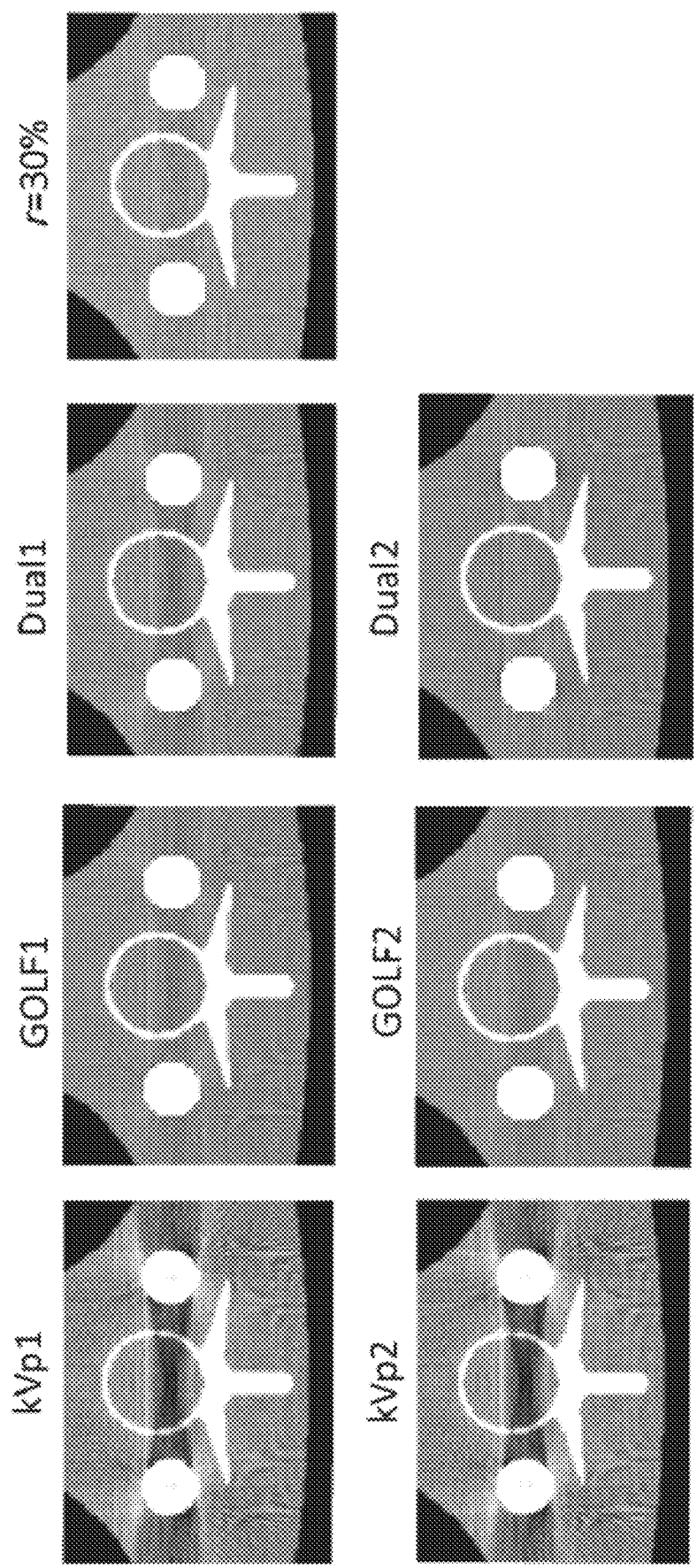
FIG. 32 shows reconstruction images around the metal rods from the six simulations plus GOLF 1 with r=30% referred to in FIG. 30A.

FIG. 31 shows 100 keV monochromatic reconstructions for the kVp 1, GOLF1 and Dual1 simulations in FIG. 30. The reconstruction images for the other 3 simulations look very similar except for residual beam hardening near the metal rods. FIG. 32 shows reconstructions around the metal rods from all 6 simulations in FIG. 30 and also for GOLF1 with r=30% (from FIG. 19). Images are displayed with win-lev=[0.01, 0.03]. Beam hardening with GOLF seems much less than that with kVp switching, and nearly equals that of dual-source CT.

All patents, patent applications, provisional applications, and publications referred to or cited herein (including those in the "References" section) are incorporated by reference in their entirety, including all figures and tables, to the extent they are not inconsistent with the explicit teachings of this specification.

REFERENCES

[1] W. A. Kalender, "X-ray computed tomography," *Physics in medicine and biology*, vol. 51, p. R29, 2006.

[2] G. Wang, H. Yu, and B. De Man, "An outlook on x-ray CT research and development," *Medical physics*, vol. 35, pp. 1051-1064, 2008.

[3] G. Wang, T.-H. Lin, P.-c. Cheng, and D. M. Shinozaki, "A general cone-beam reconstruction algorithm," *Medical Imaging, IEEE Transactions on*, vol. 12, pp. 486-496, 1993.

[4] K. Taguchi and H. Aradate, "Algorithm for image reconstruction in multi-slice helical CT," *Medical Physics*, vol. 25, pp. 550-561, 1998.

[5] G. Wang, C. R. Crawford, and W. A. Kalender, "Guest editorial-Multirow detector and cone-beam spiral/helical CT," *Medical Imaging, IEEE Transactions on*, vol. 19, pp. 817-821, 2000.

[6] T. R. Johnson, B. Krauss, M. Sedlmair, M. Grasruck, H. Bruder, D. Morhard, et al., "Material differentiation by dual energy CT: initial experience," *European radiology*, vol. 17, pp. 1510-1517, 2007.

[7] A. Graser, T. R. Johnson, H. Chandarana, and M. Macari, "Dual energy CT: preliminary observations and potential clinical applications in the abdomen," *European radiology*, vol. 19, pp. 13-23, 2009.

[8] L. Yu, S. Leng, and C. H. Mccollough, "Dual-energy CT-based monochromatic imaging," *Ajr American Journal of Roentgenology*, vol. 199, pp. S9-S15, 2012.

[9] M. Karcaaltincaba and A. Aktas, "Dual-energy CT revisited with multidetector CT: review of principles and clinical applications," *Diagnostic & Interventional Radiology*, vol. 17, pp. 181-94, 2010.

[10] J. Schlomka, E. Roessl, R. Dorscheid, S. Dill, G. Martens, T. Istel, et al., "Experimental feasibility of multi-energy photon-counting K-edge imaging in pre-clinical computed tomography," *Physics in medicine and biology*, vol. 53, p. 4031, 2008.

[11] W. C. Barber, E. Nygard, J. S. Iwanczyk, M. Zhang, E. C. Frey, B. M. Tsui, et al., "Characterization of a novel photon counting detector for clinical CT: count rate, energy resolution, and noise performance," in *SPIE Medical Imaging*, 2009, pp. 725824-725824-9.

[12] H. Gao, H. Yu, S. Osher, and G. Wang, "Multi-energy CT based on a prior rank, intensity and sparsity model (PRISM)," *Inverse problems*, vol. 27, p. 115012, 2011.

[13] J. Fornaro, S. Leschka, D. Hibbeln, A. Butler, N. Anderson, G. Pache, et al., "Dual- and multienergy CT: approach to functional imaging," *Insights Into Imaging*, vol. 2, pp. 149-159, 2011

[14] B. Li, G. Yadava, and J. Hsieh, "Quantification of head and body CTDIVOL of dual-energy x-ray CT with fast-kVp switching," *Medical Physics*, vol. 38, pp. 2595-601, 2011.

[15] R. Carmi, G. Naveh, and A. Altman, "Material separation with dual-layer CT," *IEEE Nuclear Science Symposium Conference Record Nuclear Science Symposium*, vol. 4, 2005.

[16] T. G. Flohr, C. H. Mccollough, H. Bruder, M. Petersilka, K. Gruber, C. Suß, et al., "et al. First performance evaluation of a dualsource CT (DSCT) system," *European Radiology*, vol. 16, pp. 256-68, 2006.

[17] M. Petersilka, H. Bruder, B. Krauss, K. Stierstorfer, and T. G. Flohr, "Technical principles of dual source CT," *European Journal of Radiology*, vol. 68, pp. 362-368, 2008.

[18] M. Grasruck, S. Kappler, M. Reinwand, and K. Stierstorfer, "Dual energy with dual source CT and kVp switching with single source CT: A comparison of dual energy performance," *Proceedings of SPIE—The International Society for Optical Engineering*, vol. 7258, 2009.

[19] T. G. Flohr, K. Stierstorfer, S. Ulzheimer, H. Bruder, A. N. Primak, and C. H. Mccollough, "Image reconstruction and image quality evaluation for a 64-slice CT scanner with z-flying focal spot," *Medical Physics*, vol. 32, pp. 2536-47, 2005.

[20] G. Wang, "X-ray micro-CT with a displaced detector array," *Medical Physics*, vol. 29, pp. 1634-6, 2002.

[21] V. Liu, N. R. Lariviere, and G. Wang, "X-ray micro-CT with a displaced detector array: application to helical cone-beam reconstruction," *Medical Physics*, vol. 30, pp. 2758-61, 2003.

[22] Q. Yang, W. Cong, Y. Xi, and G. Wang, "Spectral X-ray CT Reconstruction with Combination of Energy-integrating and Photon-counting Modules," *Plos ONE*, 2016.

[23] L. Yu, J. A. Christner, S. Leng, J. Wang, J. G. Fletcher, and C. H. Mccollough, "Virtual monochromatic imaging in dual-source dual-energy CT: Radiation dose and image quality," *Medical Physics*, vol. 38, pp. 6371-9, 2011.

[24] M. Beister, D. Kolditz, and W. A. Kalender, "Iterative reconstruction methods in X-ray CT," *Physica Medica*, vol. 28, pp. 94-108, 2012.

[25] M. J. Kang, C. M. Park, C. H. Lee, J. M. Goo, and H. J. Lee, "Dual-energy CT: clinical applications in various pulmonary diseases," *Radiographics*, vol. 30, pp. 685-98, 2010.

[26] Wang et al., International Patent Application Publication No. WO2016/106348.

[27] Wang et al., U.S. Patent Application Publication No. 2015/0157286.

[28] Wang et al., U.S. Patent Application Publication No. 2015/0170361.

[29] Wang et al., U.S. Patent Application Publication No. 2015/0193927.

[30] Wang et al., International Patent Application Publication No. WO2015/164405.

[31] Wang et al., U.S. Patent Application Publication No. 2016/0113602.

[32] Wang et al., U.S. Patent Application Publication No. 2016/0135769.

[33] Wang et al., U.S. Patent Application Publication No. 2016/0166852.

[34] Wang et al., International Patent Application Publication No. WO2016/106348.

[35] Wang et al., International Patent Application Publication No. WO2016/118960.

[36] Wang et al., International Patent Application Publication No. WO2016/154136.

[37] Wang et al., International Patent Application Publication No. WO2016/197127.

[38] Wang et al., International Patent Application Publication No. WO2017/015381.

[39] Wang et al., International Patent Application Publication No. WO2017/019782.

[40] Wang et al., International Patent Application No. PCT/US2016/051755.

[41] Wang et al., International Patent Application NO. PCT/US2016/061890.

[42] Wang et al., International Patent Application NO. PCT/US2017/018456.

What is claimed is:

1. A method of performing X-ray computed tomography (CT) imaging, the method comprising:
   providing an X-ray source;
   providing a detector for detecting X-ray radiation from the X-ray source;
   positioning a filter grating between the X-ray source and the detector to modify an X-ray energy spectrum of the X-ray radiation into two or more spectra, the filter grating comprising a first curvature;
   positioning an absorption grating in alignment with the filter grating to selectively block at least a portion of the X-ray radiation, the absorption grating comprising a second curvature that is concentric with the first curvature of the filter grating in relation to the X-ray source;
positioning a patient to be imaged between the filter grating and the detector;
operating the X-ray source to provide X-ray radiation; and
moving at least one of the absorption grating and the filter grating relative to the other during operation of the X-ray source.

2. The method of claim 1, wherein the filter grating and the absorption grating each are substantially cylindrical in shape and are positioned such that the X-ray source lies approximately on the axis of each cylinder.

3. The method of claim 1, wherein the filter grating and the absorption grating each are substantially at least a portion of a sphere in shape and are positioned such that the X-ray source lies approximately at the center of each sphere.

4. The method of claim 3, wherein the filter grating is at least a portion of a hemisphere.

5. The method of claim 4, wherein the movement of the at least one of the absorption grating and the filter grating is a rotation about an axis running substantially from the X-ray source to an approximate center of the absorption grating or the filter grating.

6. The method of claim 1, wherein the filter grating further comprises:
a set of first filter regions;
a set of second filter regions; and
a set of absorbing regions comprising an X-ray blocking material;
wherein the first and second filter regions produce different X-ray spectra from the X-ray radiation; and
wherein the first and second filter regions are positioned in an alternating fashion in the filter grating and the absorbing regions are positioned between each neighboring first and second filter regions.

7. The method of claim 1, wherein the movement of the at least one of the absorption grating and the filter grating is along a curved path that is parallel to the curvature of the absorption grating and the filter grating.

8. A method of performing X-ray computed tomography (CT) imaging, the method comprising:
providing an X-ray source;
providing a detector for detecting X-ray radiation from the X-ray source;
positioning a filter grating between the X-ray source and the detector to modify an X-ray energy spectrum of the X-ray radiation into two or more spectra, the filter grating being substantially at least a portion of a sphere in shape and comprising:
a set of first filter regions;
a set of second filter regions; and
a set of absorbing regions comprising an X-ray blocking material;
wherein the first and second filter regions are positioned in an alternating fashion in the filter grating and the absorbing regions are positioned between each neighboring first and second filter regions;
positioning an absorption grating in alignment with the filter grating to selectively block at least a portion of the X-ray radiation, the absorption grating being substantially at least a portion of a sphere in shape;
positioning a patient to be imaged between the filter grating and the detector;
operating the X-ray source to provide X-ray radiation;
producing, via the set of first filter regions, a first X-ray spectrum from the X-ray radiation;
producing, via the set of second filter regions, a second X-ray spectrum from the X-ray radiation, the second X-ray spectrum being different from the first X-ray spectrum; and
moving at least one of the absorption grating and the filter grating relative to the other during operation of the X-ray source.

9. The method of claim 8, wherein the filter grating comprises a first curvature and the absorption grating comprises a second curvature that is concentric to the first curvature in relation to the X-ray source.

10. The method of claim 9, wherein the movement of the at least one of the absorption grating and the filter grating is along a curved path that is parallel to the curvature of the absorption grating and the filter grating.

11. The method of claim 8, wherein the filter grating is moved relative to the absorption grating in substantially only one direction during operation of the X-ray source.

12. The method of claim 11, wherein the filter grating is rotated about an axis running substantially from the X-ray source to an approximate center of the absorption grating of the filter grating.

13. The method of claim 11, wherein the filter grating is moved by at least one reel.

14. A method of performing X-ray computed tomography (CT) imaging, the method comprising:
providing an X-ray source;
providing a detector for detecting X-ray radiation from the X-ray source;
positioning a filter grating between the X-ray source and the detector to modify an X-ray energy spectrum of the X-ray radiation into two or more spectra;
positioning an absorption grating in alignment with the filter grating to selectively block at least a portion of the X-ray radiation;
positioning a patient to be imaged between the filter grating and the detector;
operating the X-ray source to provide X-ray radiation; and
moving at least one of the absorption grating and the filter grating in substantially only one direction relative to the other during operation of the X-ray source.

15. The method of claim 14, wherein the filter grating is rotated relative to the absorption grating about an axis running substantially from the X-ray source to an approximate center of the absorption grating or the filter grating.

16. The method of claim 14, wherein the filter grating is moved relative to the absorption grating by at least one reel.

17. The method of claim 15, further comprising that the filter grating and the absorption grating each are substantially at least a portion of a sphere in shape and are positioned such that the X-ray source lies approximately at the center of each sphere; and
wherein the axis of rotation of the filter grating runs substantially from the X-ray source to an approximate center of the filter grating.

18. The method of claim 14, wherein the filter grating further comprises:
a set of first filter regions;
a set of second filter regions; and
a set of absorbing regions comprising an X-ray blocking material;
wherein the first and second filter regions produce different X-ray spectra from the X-ray radiation; and
wherein the first and second filter regions are positioned in an alternating fashion in the filter grating and the absorbing regions are positioned between each neighboring first and second filter regions.

19. The method of claim 14, wherein the filter grating comprises a first curvature and the absorption grating comprises a second curvature that is concentric to the first curvature in relation to the X-ray source.

20. The method of claim 19, wherein the movement of the at least one of the absorption grating and the filter grating is along a curved path that is parallel to the curvature of the absorption grating and the filter grating.

* * * * *